(12) United States Patent
Yoshimura et al.

(10) Patent No.: US 11,340,229 B2
(45) Date of Patent: May 24, 2022

(54) METHODS OF DIAGNOSING HEPATOCELLULAR CARCINOMA AND PANCREATIC CANCER

(71) Applicants: Abbott Japan LLC, Tokyo (JP); The University of Tokyo, Tokyo (JP)

(72) Inventors: Toru Yoshimura, Tokyo (JP); Eisaku Yoshida, Tokyo (JP); Naohiko Koshikawa, Tokyo (JP); Motoharu Seiki, Tokyo (JP)

(73) Assignees: Abbott Japan LLC, Tokyo (JP); The University of Tokyo, Tokyo (JP)

( * ) Notice: Subject to any disclaimer, the term of this patent is extended or adjusted under 35 U.S.C. 154(b) by 142 days.

(21) Appl. No.: 16/388,251

(22) Filed: Apr. 18, 2019

(65) Prior Publication Data
US 2019/0242899 A1 Aug. 8, 2019

Related U.S. Application Data

(62) Division of application No. 15/277,871, filed on Sep. 27, 2016, now abandoned.

(60) Provisional application No. 62/295,607, filed on Feb. 16, 2016, provisional application No. 62/233,745, filed on Sep. 28, 2015.

(51) Int. Cl.
*G01N 33/574* (2006.01)

(52) U.S. Cl.
CPC ... *G01N 33/57438* (2013.01); *G01N 2333/78* (2013.01); *G01N 2800/50* (2013.01); *G01N 2800/56* (2013.01)

(58) Field of Classification Search
CPC ......... G01N 33/57438; G01N 2333/78; G01N 2800/50; G01N 2800/56
USPC ....................................................... 435/7.23
See application file for complete search history.

(56) References Cited

U.S. PATENT DOCUMENTS

| | | | |
|---|---|---|---|
| 4,554,101 A | 11/1985 | Hopp | |
| 5,006,309 A | 4/1991 | Khalil et al. | |
| 5,063,081 A | 11/1991 | Cozzette et al. | |
| 5,089,424 A | 2/1992 | Khalil et al. | |
| 5,241,070 A | 8/1993 | Law et al. | |
| 5,294,404 A | 3/1994 | Grandone et al. | |
| 5,352,803 A | 10/1994 | Mattingly | |
| 5,359,093 A | 10/1994 | Adamczyk et al. | |
| 5,468,646 A | 11/1995 | Mattingly et al. | |
| 5,496,925 A | 3/1996 | Mattingly et al. | |
| 5,543,524 A | 8/1996 | Mattingly et al. | |
| 5,573,904 A | 11/1996 | Mattingly | |
| 5,593,896 A | 1/1997 | Adamczyk et al. | |
| 8,283,162 B2 | 10/2012 | Yoshimura | |
| 9,120,862 B2 | 9/2015 | Yoshimura | |
| 10,107,826 B2 * | 10/2018 | Yoshimura | G01N 33/86 |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2006/0160164 A1 | 7/2006 | Miller et al. | |
| 2008/0248493 A1 | 10/2008 | Mattingly et al. | |
| 2011/0306513 A1 | 12/2011 | Song | |
| 2012/0020972 A1 | 1/2012 | Yoshimura | |
| 2014/0045196 A1 | 2/2014 | Koshikawa et al. | |
| 2015/0072349 A1 | 3/2015 | Diamandis et al. | |
| 2017/0089905 A1 | 3/2017 | Koshikawa et al. | |

FOREIGN PATENT DOCUMENTS

| | | |
|---|---|---|
| WO | WO 2013/033609 | 7/2013 |
| WO | WO 2014/027701 | 2/2014 |

OTHER PUBLICATIONS

Adamczyk et al., "Chemiluminescence quenching of pteroic acid-N-sulf onyl acridinium-9-carboxamide conjugates by f olate binding protein," Bioorg. Med. Chem. Lett. 4:2313-2317 (2004).
Adamczyk et al., "Chemiluminescent acridinium-9-carboxamide boronic acid probes: Application to a homogeneous glycated hemoglobin assay," Bioorg. Med. Chem. Lett. 16: 1324-1328 (2006).
Adamczyk et al., "Intrinsic factor-mediated modulation of cyanocobalamin N-sulf onyl-acridinium-9-carboxamide chemiluminescence," Biorg. Med. Chem. Lett. 14: 3917-3921 (2004).
Adamczyk et al., "Linker-Mediated Modulation of the Chemiluminescent Signal from N10-(3-Sulfopropyl)-N-sulfonylacridinium-9-carboxamide Tracers," Bioconjugate Chem. 11: 714-724 (2000).
Adamczyk et al., "Modulation of the Chemiluminescent Signal from $N^{10}$-(3-Sulfopropyl)-NSulfonylacridinium-9-carboxamides," Tetrahedron 55: 10899-10914 (1999).
Adamczyk et al., "Neopentyl 3-Triflyloxypropanesulfonate. A Reactive Sulfopropylation Reagent for the Preparation of Chemiluminescent Labels," J. Org. Chem. 63: 5636-5639 (1998).
Adamczyk et al., "Regiodependent Luminescence Quenching of Biotinylated N-Sulf onylacridinium-9-carboxamides by Avidin," Org. Lett. 5: 3779-3782 (2003).
Adamczyk et al., "Synthesis of a Chemiluminescent Acridinium Hydroxylamine (AHA) for the Direct Detection of Abasic Sites in DNA," Org. Lett. 1: 779-781 (1999).
Aishima et al., "Aberrant expression of laminin gamma 2 chain and its prognostic significance in intrahepatic cholangiocarcinoma according to grown morphology," Modern Pathology, 2004, 17, 938-945.
Akobeng AK, "Understanding diagnostic tests 3: Receiver operating characteristic curves," Acta Paediatr 2007; 96: 644-647.
Arii S, Sata M, Sakamoto M, Shimada M, Kumada T, Shiina S, Yamashita T, Kokudo N, Tanaka M, Takayama T, Kudo M, "Management of hepatocellular carcinoma: Report of Consensus Meeting in the 45th Annual Meeting of the Japan Society of Hepatology (2009)," Hepatol Res 2010; 40: 667-685.

(Continued)

*Primary Examiner* — Yan Xiao
(74) *Attorney, Agent, or Firm* — Casimir Jones S.C.; Lisa Mueller

(57) ABSTRACT

Disclosed herein are biomarkers for hepatocellular carcinoma and pancreatic cancer. The biomarkers may be laminin gamma 2 monomer, PIVKA-II, AFP, CEA, CA19-9, or combinations thereof. Also disclosed herein are methods of diagnosing, prognosing, classifying risk, and monitoring progression of hepatocellular carcinoma or pancreatic cancer by the detecting the level of laminin gamma 2 monomer, PIVKA-II, AFP, CEA, CA19-9, or combinations thereof.

8 Claims, 23 Drawing Sheets

(56) References Cited

OTHER PUBLICATIONS

Baron RL, Oliver Jh III, Dodd GD III, Nalesnik M, Holbert BL, Carr B, et al., "Hepatocellular carcinoma: Evaluation with biphasic, contrast-enhanced helical CT," Radiology 1996; 199:505-511.
Bruixj, Sherman M, "Management of hepatocellular carcinoma: an update," Hepatology 2011; 53: 1020-1022.
Chan A. et al., "Validation of Biomarkers That Complement CA19.9 in Detecting Early Pancreatic Cancer", Clinical Cancer Research, 2014, vol. 20, No. 22, pp. 5787-5995.
Chen JG, Parkin DM, Chen QG, Lu JH, Shen QJ, Zhang BC, Zhu YR, "Screening for liver cancer: results of a randomized controlled trial in Qidong, China," J Med Screen 2003; 10: 204-209.
Domogatskaya A, Rodin S, Tryggvason K, "Functional diversity of laminins," Annu Rev Cell Dev Biol. 2012; 28: 523-53.
El-Serag HB, "Hepatocellular carcinoma," N Engl J Med 2011; 365: 1118-1127.
Giannelli G, Fransvea E, Bergamini C, Marinosci F, Antonaci S, "Laminin-5 chains are expressed differentially in metastatic and nonmetastatic hepatocellular carcinoma," Clin Cancer Res 2003; 9: 3684-3691.
Govaere et al., "Keratin 19: a key role player in the invasion of human hepatocellular carcinomas," Gut, 2014, 63:674-685.
Hashimoto E, Tokushige K, "Hepatocellular carcinoma in non-alcoholic steatohepatitis: Growing evidence of an epidemic?," Hepatology Res 2012; 42: 1-14.
Hashimoto et al., "Analysis of DNA copy number aberrations in hepatitis C virus-associated hepatocellular carcinomas by conventional CGH and array CGH," Modern Pathology, 2004, 17, 617-622.
Heagerty et al., "Time-dependent ROC curves for censored survival data and a diagnostic marker," Biometrics 56:337-44 (2000).
International Search Report and Written Opinion for Application No. PCT/JP2016/079711 dated Mar. 24, 2017 (19 pages).
Invitation to Pay Additional Fees for Application No. PCT/JP2016/079711 dated Jan. 17, 2017 (8 pages).
Ishii M, Gama H, Chida N, Ueno Y, Shinzawa H, Takagi T, Toyota T, Takahashi T, Kasukawa R, "Simultaneous measurements of serum alpha-fetoprotein and protein induced by vitamin K absence for detecting hepatocellular carcinoma. South Tohoku District Study Group," Am J Gastroenterol. 2000; 95: 1036-40.
Kasahara A, Hayashi N, Fusamoto H, Kawada Y, Imai Y, Yamamoto H, Hayashi E, et al., "Clinical evaluation of plasma des-gamma-carboxy prothrombin as a marker protein of hepatocellular carcinoma in patients with tumors of various sizes," Dig Dis Sci 1993; 38: 2170-2176.
Katayama M. et al., "Laminin @c2-chain fragment circulating level increases in patients with metastatic pancreatic ductal cell adenocarcinomas," Cancer Letters, 2005, vol. 225, No. 1, pp. 167-176.
Kosanam H, Prassas I, Chrystoja CC, Soleas I, Chan A, Dimitromanolakis A, Blasutig IM, Rückert F, Gruetzmann R, Pilarsky C Maekawa M, Brand R, Diamandis EP, "Laminin, gamma 2 (LAMC2): a promising new putative pancreatic cancer biomarker identified by proteomic analysis of pancreatic adenocarcinoma tissues," Mol Cell Proteomics 2013; 12: 2820-2832.
Koshikawa N, Minegishi T, Nabeshima K, Seiki M, "Development of a new tracking tool for the human monomeric laminin-γ2 chain in vitro and in vivo," Cancer Res 2008; 68: 530-536.
Koshikawa N, Minegishi T, Sharabi A, Quaranta V, Seiki M, "Membrane-type matrix metalloproteinase-1 (MT1-MMP) is a processing enzyme for human lamininγ2 chain," J Biol Chem 2005; 280: 88-93.
Koshikawa N, Moriyama K, Takamura H, et al., "Overexpression of laminin γ2 chain monomer in invading gastric carcinoma cells," Cancer Res 1999; 59: 5596-5601.
Kyte et al., "A Simple Method for Displaying the Hydropathic Character of a Protein," J. Mol. Biol. 157:105-132 (1982).
Lok AS, Sterling RK, Everhart JE, Wright EC, Hoefs JC, Di Bisceglie AM, Morgan TR, Kim HY, Lee WM, Bonkovsky HL, Dienstag JL, "HALT-C Trial Group. Des-gamma-carboxy prothrombin and alpha-fetoprotein as biomarkers for the early detection of hepatocellular carcinoma," Gastroenterology 2010; 138: 493-502.
Marrero JA, Su GL, Wei W, Emick D, Conjeevaram HS, Fontana RJ, Lok AS, "Desgamma carboxyprothrombin can differentiate hepatocellular carcinoma from nonmalignant chronic liver disease in American patients," Hepatology 2003; 37: 1114-1121.
Masanori II, Yamamoto H, Taniguchi H, Adachi Y, Nakazawa M, Ohashi H, Tanuma T, Sukawa Y, Suzuki H, Sasaki S, Imai K, Shinomura Y, "Co-expression of laminin β3 and γ2 chains and epigenetic inactivation of laminin α3 chain in gastric cancer," Int J Oncol 2011; 39: 593-599.
Mattingly et al., In Luminescence Biotechnology: Instruments and Applications; Dyke, K. V. Ed.; CRC Press: Boca Raton, pp. 77-105 (2002).
Mattingly, J. "Chemiluminescent 1 O-Methyl-Acridinium-9-(N-Sulphonylcarboxamide) Salts. Synthesis and Kinetics of Light Emission," Biolumin. Chemilumin. 6: 107-114 (1991).
McCapra et al., "Chemiluminescence Involving Peroxide Decompositions," Photochem. Photobiol. 4: 1111-21 (1965).
Mita Y, Aoyagi Y, Yanagi M, Suda T, Suzuki Y, Asakura H, "The usefulness of determining des- gamma-carboxy prothrombin by sensitive enzyme immunoassay in the early diagnosis of patients with hepatocellular carcinoma," Cancer 1998; 82: 1643-1648.
Miyazaki K, "Laminin-5 (laminin-332): Unique biological activity and role in tumor growth and invasion," Cancer Sci 2006; 97: 91-98.
Mizushima H, Koshikawa N, Moriyama K, Takamura H, Nagashima Y, Hirahara F, Miyazaki K, "Wide distribution of laminin-5 γ2 chain in basement membranes of various human tissues," Hor Res 1998; 50 (Suppl. 2): 7-14.
Nagaoki Y, Hyogo H, Aikata H, Tanaka M, Naeshiro N, Nakahara T, Honda Y, Miyaki D, Kawaoka K, Takak S, Hiramatsu A, Waki K, Imamura M, Kawakami Y, Takahash S, Chayama K, "Recent trend of clinical features in patients with hepatocellular carcinoma," Hepatology Res 2012; 42: 368-375.
Oka T, Yamamoto H, Sasaki S, Ii M, Hizaki K, Taniguchi H, Adachi Y, Imai K, Shinomura Y, "Overexpression of α3/β2 chains of laminin-5 and MMP7 in biliary cancer," World J Gastroenterol 2009; 15: 3865-3873.
Omata M, Lesmana LA, Tateishi R, Chen PJ, Lin SM, Yoshida H, Kudo M, Lee JM, Choi BI, Poon RT, Shiina S, Cheng AL, Jia JD, Obi S, Han KH, Jafri W, Chow P, Lim SG, Chawla YK, Budihusodo U, Gani RA, Lesmana CR, Putranto TA, Liaw YF, Sarin SK, "Asian Pacific Association for the Study of the Liver consensus recommendations on hepatocellular carcinoma," Hepatol Int 2010; 4: 439-474.
Razavi et al., "Stable and versatile active acridinium esters I," Luminescence 15: 239-244 (2000).
Razavi et al., "Stable and versatile active acridinium esters II," Luminescence 15: 245-249 (2000).
Sherman M., "Surveillance for hepatocellular carcinoma," Best Practice Res Clin Gastroenterol 2014; 28: 783-793.
Soini Y, Määttä M, Salo S, Tryggvason K, Autio-Harmainens H, "Expression of the laminin γ2 chain in pancreatic adenocarcinoma," J Pathol 1996; 180: 290-294.
Sordat I, Bosman FT, Dorta G, Rousselle P, Aberdam D, Blum AL, Sordat B, "Differential expression of laminin-5 subunits and integrin receptors in human colorectal neoplasia," J Pathol 1998; 185: 44-52.
Sterling RK, Wright EC, Morgan TR, Seeff LB, Hoefs JC, Di Bisceglie AM, Dienstag JL, Lok AS, "Frequency of elevated hepatocellular carcinoma (HCC) biomarkers in patients with advanced hepatitis C," Am J Gastroenterol 2012; 107: 64-74.
Tateishi R, Yoshida H, Matsuyama Y, Mine N, Kondo Y, Omata M, "Diagnostic accuracy of tumor markers for hepatocellular carcinoma: a systematic review," Hepatol Int 2008; 2: 17-30.
Tempero et al., "Pancreatic Adenocarcinoma," National Comprehensive Cancer Network (NCCN) Guidelines Version 2.2012, 2012, vol. 10, No. 6, 703-713.
Van Meer S, de Man RA, Siersema PD, van Erpecum KJ., "Surveillance for hepatocellular carcinoma in chronic liver disease: evidence and controversies," World J Gastroenterol 2013; 19: 6744-6756.
World Health Organization, International Agency for Research on Cancer. GLOBOCAN 2012. (http://globocan.iarc.fr).

(56) References Cited

OTHER PUBLICATIONS

Yachida et al., "Distant metastasis occurs late during the genetic evolution of pancreatic cancer," (2010) Nature 467:1114-1117.

Yamamoto H, Itoh F, Iku S, Hosokawa M, Imai K, "Expression of the γ2 chain of laminin-5 at the invasive front is associated with recurrence and poor prognosis in human esophageal squamous cell carcinoma," Clin Cancer Res 2001; 7: 896-900.

Yoon YJ, Han KH, Kim DY, "Role of serum prothrombin induced by vitamin K absence or antagonist-II in the early detection of hepatocellular carcinoma in patients with chronic hepatitis B virus infection," Scandinavian J Gastroenterology 2009; 44: 861-866.

Zhang et al., "ROCK is involved in Vasculogenic Mimicry Formation in Hepatocellular Carcinoma Cell Line," PLoS ONE, 2014, 9:9, p. e107661.

Yu et al., "Study on the significance of serum PIVKA—II in diagnosis of hepatocellular carcinoma." Journal of Clinical and Experimental Medicine, Apr. 2014, 13(7): 513-516.

\* cited by examiner

METHODS OF DIAGNOSING HEPATOCELLULAR CARCINOMA AND PANCREATIC CANCER

CROSS-REFERENCE TO RELATED APPLICATION(S)

This application is a divisional of copending U.S. application Ser. No. 15/277,871, filed Sep. 27, 2016, which claims the benefit of U.S. Provisional Patent Application No. 62/233,745, filed Sep. 28, 2015, and U.S. Provisional Patent Application No. 62/295,607, filed Feb. 16, 2016, all of which are incorporated by reference herein.

TECHNICAL FIELD

This disclosure relates to methods and immunoassay platforms for determining a prognosis, diagnosis, or risk identification of hepatocellular carcinoma or pancreatic cancer in a patient by detecting one or more biomarkers in the patient as well as determining amounts thereof. The one or more biomarkers may be used to identify a patient with hepatocellular carcinoma or pancreatic cancer, to identify a patient as a candidate for hepatocellular carcinoma therapy or pancreatic cancer therapy, to classify a patient's risk of developing hepatocellular carcinoma or pancreatic cancer, or to classify a patient's stage or risk of progression of hepatocellular carcinoma or pancreatic cancer, as well as to determine a diagnosis, prognosis, or a treatment regimen.

BACKGROUND

Cancer is a disease that occurs in many forms, for example, hepatocellular carcinoma and pancreatic cancer. Hepatocellular carcinoma is the most common form of liver cancer and often is secondary to viral hepatitis infection and/or liver cirrhosis. Detection of hepatocellular carcinoma can be difficult as many symptoms overlap with symptoms associated with liver disease. In some instances, hepatocellular carcinoma may be detected by abdominal imaging and/or needle biopsy.

Pancreatic cancer is a leading cause of death due to cancer because it is difficult to detect in early stages and it spreads rapidly. Accordingly, detection of pancreatic cancer does not typically occur until the appearance of symptoms in the advanced stages of the cancer.

Accordingly, a need exists in the art for the identification of methods that provide earlier and/or more accurate detection of hepatocellular carcinoma and pancreatic cancer.

SUMMARY

In one aspect, the present invention relates to a method of diagnosing hepatocellular carcinoma (HCC) in a subject in need thereof, the method comprising: (a) obtaining a biological sample from the subject; (b) determining a level of laminin gamma 2 monomer in the biological sample; (c) comparing the level of laminin gamma 2 monomer to a reference level of laminin gamma 2 monomer; and (d) identifying the subject as having HCC when the level of laminin gamma 2 monomer is greater than the reference level of laminin gamma 2 monomer.

In another aspect, the present invention relates to a method of determining if a subject has or is at risk of developing hepatocellular carcinoma (HCC), the method comprising: (a) obtaining a biological sample from the subject; (b) measuring a level of laminin gamma 2 monomer in the biological sample; (c) comparing the level of laminin gamma 2 monomer to a reference level of laminin gamma 2 monomer; and (d) determining the subject has or is at risk of developing HCC when the level of laminin gamma 2 monomer is greater than the reference level of laminin gamma 2 monomer.

In another aspect, the present invention relates to a method of monitoring progression of hepatocellular carcinoma (HCC) in a subject in need thereof, the method comprising: (a) obtaining first and second biological samples from the subject; (b) measuring a first level of laminin gamma 2 monomer in the first biological sample and a second level of laminin gamma 2 monomer in the second biological sample; (c) comparing the first and second levels of laminin gamma 2 monomer; and (d) determining (i) HCC has progressed in the subject when the second level of laminin gamma 2 monomer is greater than the first level of laminin gamma 2 monomer or (ii) HCC has not progressed in the subject when the second level of laminin gamma 2 monomer is equivalent to or less than the first level of laminin gamma 2 monomer.

In another aspect, the present invention relates to a kit for detecting HCC in a subject in need thereof, the kit comprising one or more reagents for detecting laminin gamma 2 monomer.

In another aspect, the present invention relates to a method of diagnosing hepatocellular carcinoma (HCC) in a subject in need thereof, the method comprising: (a) obtaining a biological sample from the subject; (b) determining (i) a level of laminin gamma 2 monomer and a level of protein induced vitamin K antagonist-II (PIVKA-II) in the biological sample; (ii) the level of laminin gamma 2 monomer and a level of alpha fetal protein (AFP) in the biological sample; or (iii) the level of laminin gamma 2 monomer, the level of PIVKA-II, and the level of AFP in the biological sample; (c) comparing (i) the level of laminin gamma 2 monomer to a reference level of laminin gamma 2 monomer and the level of PIVKA-II to a reference level of PIVKA-II; (ii) the level of laminin gamma 2 monomer to the reference level of laminin gamma 2 monomer and the level of AFP to a reference level of AFP; or (iii) the level of laminin gamma 2 monomer to the reference level of laminin gamma 2 monomer, the level of PIVKA-II to the reference level of PIVKA-II, and the level of AFP to the reference level of AFP; and (d) identifying the subject as having HCC when (i) the level of laminin gamma 2 monomer is greater than the reference level of laminin gamma 2 monomer and the level of PIVKA-II is greater than the reference level of PIVKA-II; (ii) the level of laminin gamma 2 monomer is greater than the reference level of laminin gamma 2 monomer and the level of AFP is greater than the reference level of AFP; or (iii) the level of laminin gamma 2 monomer is greater than the reference level of laminin gamma 2 monomer, the level of PIVKA-II is greater than the reference level of PIVKA-II, and the level of AFP is greater than the reference level of AFP.

In another aspect, the present invention relates to a method of determining if a subject has or is at risk of developing hepatocellular carcinoma (HCC), the method comprising: (a) obtaining a biological sample from the subject; (b) measuring (i) a level of laminin gamma 2 monomer and a level of PIVKA-II in the biological sample; (ii) the level of laminin gamma 2 monomer and a level of AFP in the biological sample; or (iii) the level of laminin gamma 2 monomer, the level of PIVKA-II, and the level of AFP in the biological sample; (c) comparing (i) the level of laminin gamma 2 monomer to a reference level of laminin gamma 2 monomer and the level of PIVKA-II to a reference level of PIVKA-II; (ii) the level of laminin gamma 2 monomer to the reference level of laminin gamma 2 monomer and the level of AFP to a reference level of AFP; or (iii) the level of laminin gamma 2 monomer to the reference level of laminin gamma 2 monomer, the level of PIVKA-II to the reference level of PIVKA-II, and the level of AFP to the reference level of AFP; and (d) determining the subject has or is at risk of developing HCC when (i) the level of laminin gamma 2 monomer is greater than the reference level of laminin gamma 2 monomer and the level of PIVKA-II is greater than the reference level of PIVKA-II; (ii) the level of laminin gamma 2 monomer is greater than the reference level of laminin gamma 2 monomer and the level of AFP is greater than the reference level of AFP; or (iii) the level of laminin gamma 2 monomer is greater than the reference level of laminin gamma 2 monomer, the level of PIVKA-II is greater than the reference level of PIVKA-II, and the level of AFP is greater than the reference level of AFP.

In another aspect, the present invention relates to a method of monitoring progression of hepatocellular carcinoma (HCC) in a subject in need thereof, the method comprising: (a) obtaining first and second biological samples from the subject; (b) measuring (i) a first level of laminin gamma 2 monomer and a first level of PIVKA-II in the first biological sample and a second level of laminin gamma 2 monomer and a second level of PIVKA-II in the second biological sample; (ii) the first level of laminin gamma 2 monomer and a first level of AFP in the first biological sample and the second level of laminin gamma 2 monomer and a second level of AFP in the second biological sample; or (iii) the first level of laminin gamma 2 monomer, the first level of PIVKA-II, and the first level of AFP in the first biological sample and the second level of laminin gamma 2 monomer, the second level of PIVKA-II, and the second level of AFP in the second biological sample; (c) comparing (i) the first and second levels of laminin gamma 2 monomer and the first and second levels of PIVKA-II; (ii) the first and second levels of laminin gamma 2 monomer and the first and second levels of AFP; or (iii) the first and second levels of laminin gamma 2 monomer, the first and second levels of PIVKA-II, and the first and second levels of AFP; and (d) determining (1) HCC has progressed in the subject when (i) the second level of laminin gamma 2 monomer is greater than the first level of laminin gamma 2 monomer and the second level of PIVKA-II is greater than the first level of PIVKA-II; (ii) the second level of laminin gamma 2 monomer is greater than the first level of laminin gamma 2 monomer and the second level of AFP is greater than the first level of AFP; or (iii) the second level of laminin gamma 2 monomer is greater than the first level of laminin gamma 2 monomer, the second level of PIVKA-II is greater than the first level of PIVKA-II, and the second level of AFP is greater than the first level of AFP; or (2) HCC has not progressed in the subject when (i) the second level of laminin gamma 2 monomer is equivalent to or less than the first level of laminin gamma 2 monomer and the second level of PIVKA-II is equivalent to or less than the first level of PIVKA-II; (ii) the second level of laminin gamma 2 monomer is equivalent to or less than the first level of laminin gamma 2 monomer and the second level of AFP is equivalent to or less than the first level of AFP; or (iii) the second level of laminin gamma 2 monomer is equivalent to or less than the first level of laminin gamma 2 monomer, the second level of PIVKA-II is equivalent to or less than the first level of PIVKA-II, and the second level of AFP is equivalent to or less than the first level of AFP.

In another aspect, the present invention relates to a kit for detecting HCC in a subject in need thereof, the kit comprising (i) one or more reagents for detecting laminin gamma 2 monomer and one or more reagents for detecting PIVKA-II; (ii) one or more reagents for detecting laminin gamma 2 monomer and one or more reagents for detecting AFP; or (iii) one or more reagents for detecting laminin gamma 2 monomer, one or more reagents for detecting PIVKA-II, and one or more reagents for detecting AFP.

In another aspect, the present invention relates to a method for diagnosing pancreatic cancer in a subject in need thereof, the method comprising: (a) obtaining a biological sample from the subject; (b) determining a level of laminin gamma 2 monomer in the biological sample; (c) determining a level of at least one additional biomarker in the biological sample, wherein the at least one additional biomarker is selected from the group consisting of: carcinoembryonic antigen (CEA) and carbohydrate antigen 19-9 (CA19-9); (d) comparing the level of laminin gamma 2 monomer to a reference level of laminin gamma 2 monomer and the level of the at least one additional biomarker to a reference level of the at least one additional biomarker; and (e) identifying the subject has having pancreatic cancer when the levels of laminin gamma 2 monomer and the at least one additional biomarker are greater than the reference levels of laminin gamma 2 monomer and the at least one additional biomarker.

In another aspect, the present invention relates to a method of determining if a subject has or is at risk of developing pancreatic cancer, the method comprising: (a) obtaining a biological sample from the subject; (b) measuring a level of laminin gamma 2 monomer in the biological sample; (c) measuring a level of at least one additional biomarker in the biological sample, wherein the at least one additional biomarker is selected from the group consisting of: carcinoembryonic antigen (CEA) and carbohydrate antigen 19-9 (CA19-9); (d) comparing the level of laminin gamma 2 monomer to a reference level of laminin gamma 2 monomer and the level of the at least one additional biomarker to a reference level of the at least one additional biomarker; and (e) determining the subject has or is at risk of developing pancreatic cancer when the levels of laminin gamma 2 monomer and the at least one additional biomarker are greater than the reference levels of laminin gamma 2 monomer and the at least one additional biomarker.

In another aspect, the present invention relates to a method of monitoring progression of pancreatic cancer in a subject in need thereof, the method comprising: (a) obtaining first and second biological samples from the subject; (b) measuring a first level of laminin gamma 2 monomer in the first biological sample and a second level of laminin gamma 2 monomer in the second biological sample; (c) measuring a first level of at least one additional biomarker in the first biological sample and a second level of the at least one additional biomarker in the second biological sample, wherein the at least one additional biomarker is selected from the group consisting of: carcinoembryonic antigen (CEA) and carbohydrate antigen 19-9 (CA19-9); (d) comparing the first and second levels of laminin gamma 2 monomer; (e) comparing the first and second levels of the at least one additional biomarker; and (f) determining (i) the pancreatic cancer has progressed in the subject when the second levels of laminin gamma 2 monomer and the at least one additional biomarker are greater than the first levels of laminin gamma 2 monomer and the at least one additional biomarker or (ii) the pancreatic cancer has not progressed in the subject when the second levels of laminin gamma 2 monomer and the at least one additional biomarker are equivalent to or less than the first levels of laminin gamma 2 monomer and the at least one additional biomarker.

In another aspect, the present invention relates to a kit for detecting pancreatic cancer in a subject in need thereof, the kit comprising: (a) one or more reagents for detecting laminin gamma 2 monomer; and (b) one or more reagents for detecting at least one additional biomarker, wherein the at least one additional biomarker is selected from the group consisting of: carcinoembryonic antigen (CEA) and carbohydrate antigen 19-9 (CA19-9).

DETAILED DESCRIPTION

Figure 1:
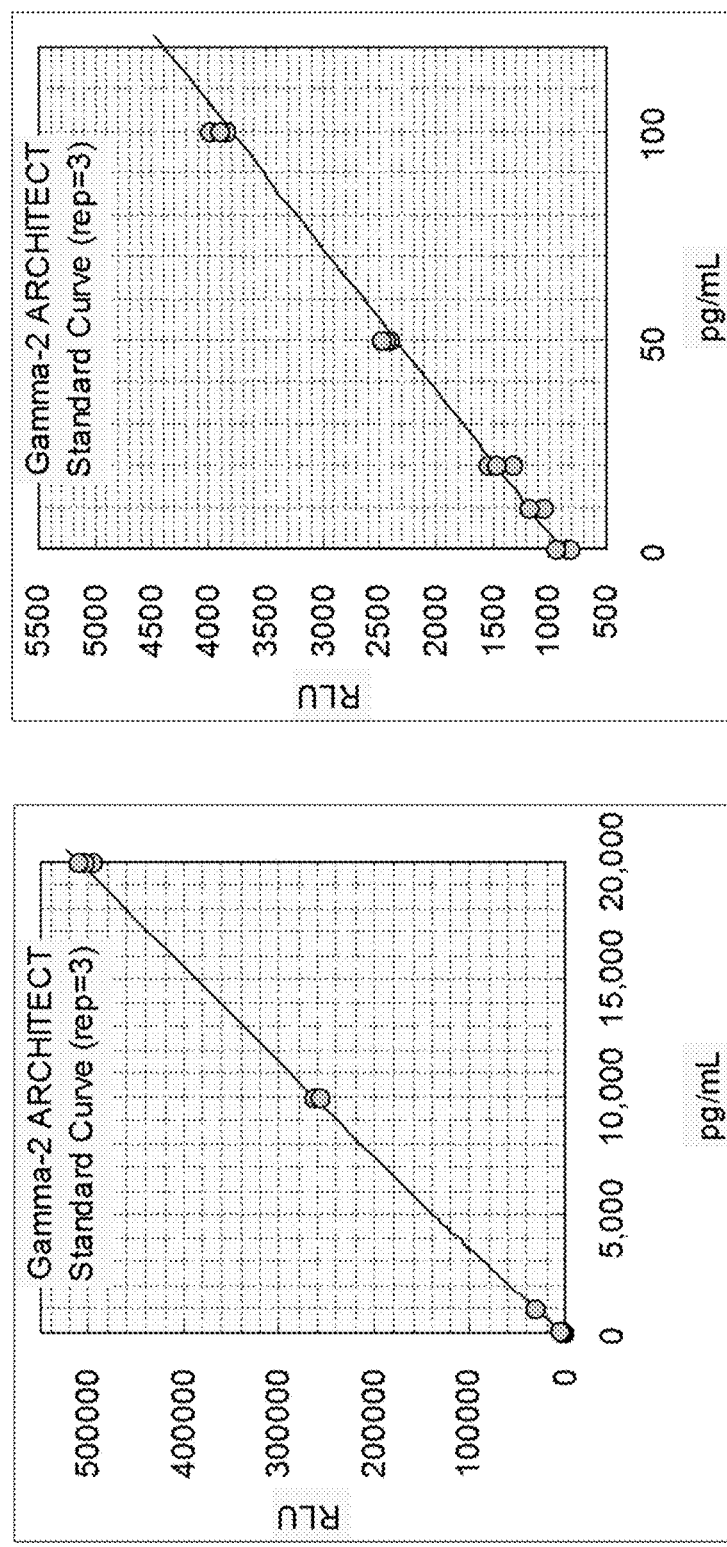
FIG. 1 shows graphs plotting laminin gamma 2 monomer concentration (pg/mL) against relative light units (RLU). Specifically, each graph depicts a representative calibration curve for the immunoassay described in Example 2. For the graph on the left, the laminin gamma 2 monomer concentration was 0 pg/mL to 20,000 pg/mL. For the graph on the right, the laminin gamma 2 monomer concentration was 0 pg/mL to 100 pg/mL. Each calibration curve was derived from three replicates.

The present disclosure relates to biomarkers for detecting hepatocellular carcinoma and/or pancreatic cancer. The present disclosure is directed to analyzing or quantifying the levels of laminin gamma 2 monomer, PIVKA-II, AFP, CEA, CA19-9, or combinations thereof, for diagnosing, prognosing, classifying risk, and monitoring progression of hepatocellular carcinoma or pancreatic cancer in a subject. The biomarkers for detecting hepatocellular carcinoma may be laminin gamma 2 monomer, PIVKA-II, AFP, or combinations thereof. The biomarkers for detecting pancreatic cancer may be laminin gamma 2 monomer, CEA, CA19-9, or combinations thereof.

The present disclosure discloses methods in which the biomarker laminin gamma 2 monomer may be used to identify or diagnose, which includes aiding in identifying or diagnosing, a patient with hepatocellular carcinoma and/or pancreatic cancer, to identify or aid in identifying whether a patient is suffering from hepatocellular carcinoma and/or pancreatic cancer, to classify a patient's risk of developing hepatocellular carcinoma and/or pancreatic cancer, as well as to determine or aid in determining a diagnosis, prognosis or treatment regimen. The level of laminin gamma 2 monomer is higher in a subject suffering from or at risk of suffering from hepatocellular carcinoma or pancreatic cancer as compared to a subject not suffering from or at risk of suffering from hepatocellular carcinoma or pancreatic cancer. The level of laminin gamma 2 monomer may increase with advanced stages of hepatocellular carcinoma or pancreatic cancer. The methods described herein may be used in conjunction with other biomarkers, such as PIVKA-II, AFP, CEA, CA19-9, or combinations thereof, to identify and diagnose, which includes aiding in identifying or diagnosing, patients suffering from hepatocellular carcinoma and/or pancreatic cancer.

Section headings as used in this section and the entire disclosure herein are merely for organization purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The "area under curve" or "AUC" refers to area under a ROC curve. AUC under a ROC curve is a measure of accuracy. An area of 1 represents a perfect test, whereas an area of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers may include, but are not limited to, Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer (including hepatocellular carcinoma), Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

"Control subject" as used herein refers to a healthy subject, i.e., a subject having no clinical signs or symptoms of hepatocellular carcinoma, pancreatic cancer, or cancer other than hepatocellular carcinoma or pancreatic cancer. The control subject is clinically evaluated for otherwise undetected signs or symptoms of hepatocellular carcinoma, pancreatic cancer, or cancer other than hepatocellular carcinoma or pancreatic cancer, which evaluation may include routine physical examination and/or laboratory testing.

"Control group" as used herein refers to a group of control subjects or healthy subjects, i.e. a group of subjects who have no clinical signs or symptoms of hepatocellular carcinoma, pancreatic cancer, or cancer other than hepatocellular carcinoma or pancreatic cancer.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"TNM system for staging hepatocellular carcinoma" or "TNM system for staging HCC" as used interchangeably herein refers to a system for staging hepatocellular carcinoma (HCC). "T" describes the number and size of the primary tumor(s), measured in centimeters (cm), and whether the cancer has grown into nearby blood vessels or organs. "N" describes the extent of spread to nearby (regional) lymph nodes. "M" indicates whether the cancer has metastasized (spread) to distant parts of the body. Numbers or letters may appear after "T," "N," and "M" to provide more details for each of these factors. Specifically, the numbers 0-4 indicate increasing severity. The letter "X" indicates "cannot be assessed" because information was not available.

The "T" groups may be "TX," "T0," "T1," "T2,", "T3a," "T3b," and "T4." "TX" indicates the primary tumor cannot be assessed. "T0" indicates no evidence of primary tumor. "T1" indicates a single tumor (any size) that has not grown into blood vessels. "T2" indicates either a single tumor (any size) that has grown into blood vessels or more than one tumor, but no tumor is larger than 5 cm (about 2 inches) across. "T3a" indicates more than one tumor, with at least one tumor larger than 5 cm across. "T3b" indicates at least one tumor (any size) that has grown into a major branch of a large vein of the liver (the portal or hepatic vein). "T4" indicates the tumor (any size) has grown into a nearby organ (other than the gallbladder) or the tumor is growing into the thin layer of tissue covering the liver (called visceral peritoneum).

The "N" groups may be "NX," "N0," and "N1." "NX" indicates regional (nearby) lymph nodes cannot be assessed. "N0" indicates the cancer has not spread to the regional lymph nodes. "N1" indicates the cancer has spread to the regional lymph nodes.

The "M" groups may be "M0" and "M1." "M0" indicates the cancer has not spread to distant lymph nodes or other organs. "M1" indicates the cancer has spread to distant lymph nodes or organs. Liver cancer, including hepatocellular carcinoma, may spread to the lining of the belly (peritoneum), the lungs, and to bones.

"Stage I hepatocellular carcinoma" and "stage I HCC" as used interchangeably herein refer to a TNM classification of T1, N0, and M0. There is a single tumor (any size) that has not grown into any blood vessels. The cancer has not spread to nearby lymph nodes or distant sites.

"Stage II hepatocellular carcinoma" and "stage II HCC" as used interchangeably herein refer to a TNM classification of T2, N0, and M0. Either there is a single tumor (any size) that has grown into blood vessels or there are several tumors, and all are 5 cm (2 inches) or less across. The cancer has not spread to nearby lymph nodes or distant sites.

"Stage IIIA hepatocellular carcinoma" and "stage IIIA HCC" as used interchangeably herein refer to a TNM classification of T3a, N0, and M0. There is more than one tumor, and at least one tumor is larger than 5 cm (2 inches) across. The cancer has not spread to nearby lymph nodes or distant sites.

"Stage IIIB hepatocellular carcinoma" and "stage IIIA HCC" as used interchangeably herein refer to a TNM classification of T3b, N0, and M0. At least one tumor is growing into a branch of a major vein of the liver (portal vein or hepatic vein). The cancer has not spread to nearby lymph nodes or distant sites.

"Stage IIIC hepatocellular carcinoma" and "stage IIIC HCC" as used interchangeably herein refer to a TNM classification of T4, N0, and M0. A tumor is growing into a nearby organ (other than the gallbladder) or a tumor has grown into the outer covering of the liver. The cancer has not spread to nearby lymph nodes or distant sites.

"Stage IVA hepatocellular carcinoma" and "stage IVA HCC" as used interchangeably herein refer to a TNM classification of any T, N1, and M0. Tumors in the liver can be any size or number and the tumors may have grown into blood vessels or nearby organs. The cancer has spread to nearby lymph nodes. The cancer has not spread to distant sites.

"Stage IVB hepatocellular carcinoma" and "stage IVB HCC" as used interchangeably herein refer to a TNM classification of any T, any N, and M1. The cancer has spread to other parts of the body. Tumors can be any size or number, and nearby lymph nodes may or may not be involved.

"Liver cancer" as used herein refers to cancer that originates in the liver. Liver cancer may include hepatocellular carcinoma (HCC) and fibrolamellar carcinoma. In most cases, the cause of liver cancer is usually scarring of the liver (i.e., liver cirrhosis).

"Liver cirrhosis" as used herein refers to the consequence of chronic liver disease characterized by replacement of liver tissue by fibrosis, scar tissue, and regenerative nodules (i.e., lumps that occur because of a process in which damaged tissue is regenerated, leading to loss of liver function). The architectural organization of the functional units of the liver become so disrupted that blood flow through the liver and liver function become disrupted. Cirrhosis is most commonly caused by alcoholism, hepatitis B and C, and fatty liver disease, but has many other possible causes. Some cases are idiopathic (i.e., of unknown cause). Once liver cirrhosis has developed, the serious complications of liver disease may occur including portal hypertension, liver failure, and liver cancer. The risk of liver cancer is greatly increased once cirrhosis develops and cirrhosis should be considered to be a pre-malignant condition. Cirrhosis may be caused by alcohol abuse, autoimmune diseases of the liver, Hepatitis B or C virus infection, inflammation of the liver that is long-term (chronic), and iron overload in the body (hemochromatosis). Patients with hepatitis B or C are at risk for liver cancer, even if they have not developed cirrhosis.

"Liver disease" as used herein refers to damage to or disease of the liver. Symptoms of liver dysfunction include both physical signs and a variety of symptoms related to digestive problems, blood sugar problems, immune disorders, abnormal absorption of fats, and metabolism problems. Liver disease includes liver fibrosis, liver cirrhosis, and liver cancer. All chronic liver diseases can lead to liver fibrosis. Chronic liver disease may be caused by chronic viral hepatitis B and alcoholic liver disease.

"Liver fibrosis" as used herein refers to an excessive accumulation of extracellular matrix proteins including collagen that occurs in most types of chronic liver diseases. Liver fibrosis is the scarring process that represents the liver's response to injury or illness. Liver fibrosis may be caused by infections due hepatitis B and C, parasites, excessive alcohol use and exposure to toxic chemicals, including pharmaceutical drugs and blocked bile ducts. Advanced liver fibrosis results in cirrhosis, liver failure, and portal hypertension and often requires liver transplantation.

"Neoplasia" as used herein refers to an abnormal growth of tissue. Neoplasia is commonly referred to as a tumor. The abnormal growth usually but not always forms a mass.

"Normal control" or "healthy control" as used herein means a sample or specimen taken from a subject, or an actual subject who does not have hepatocellular carcinoma, pancreatic cancer or any cancer, or is not at risk of developing cancer.

"Normal," "healthy," and "control" as used herein interchangeably refer to samples taken from subject or subjects that do not have hepatocellular carcinoma, pancreatic cancer or any cancer, or is not at risk of developing cancer.

"Benign pancreatic disease" and "pancreatic disease" as used herein interchangeably refer to pancreatic disease which is not cancer or has become cancer. Benign pancreatic disease includes pancreatitis, various types of cysts and tumors, pancreatic intraepithelial neoplasia (PanIN) and intraductal papillary mucinous neoplasm (IPMN) lesions, and mucinous cystic neoplasm (MCN).

"Early stage pancreatic cancer" as used herein refers to pancreatic cancer which is limited to the pancreas, outside the pancreas or nearby lymph nodes, but has not expanded into nearby major blood vessels or nerves or distant organs. Early stage pancreatic cancer includes stage 0, stage I and stage II pancreatic cancers. See Yachida et al. (2010) Nature 467:1114-1119; see also National Comprehensive Cancer Network (NCCN) Guidelines Version 2.2012 Pancreatic Adenocarcinoma.

"Late stage pancreatic cancer" as used herein refers to pancreatic cancer which has expanded into nearby major blood vessels, nerves or distant organs. Late stage pancreatic cancer includes stage III or stage IV pancreatic cancer.

"Stage 0 pancreatic cancer" as used herein refers to pancreatic cancer limited to a single layer of cells in the pancreas. The pancreatic cancer is not visible on imaging tests or to the naked eye. The tumor is confined to the top layers of pancreatic duct cells and has not invaded deeper tissues or spread outside of the pancreas. Stage 0 tumors are sometimes referred to as pancreatic carcinoma in situ or pancreatic intraepithelial neoplasia III (PanIn III).

"Stage I pancreatic cancer" as used herein refers to cancer confined or limited to the pancreas and has not spread to nearby lymph nodes. "Stage IA" refers to a tumor confined to the pancreas and is less than 2 cm in size. "Stage IB" refers to a tumor confined to the pancreas and is greater than 2 cm in size.

"Stage II pancreatic cancer" as used herein refers to local spread cancer that has grown outside the pancreas or has spread to nearby lymph nodes. "Stage IIA" refers to a tumor growing outside the pancreas but not into large blood vessels, nearby lymph nodes or distant sites. "Stage IIB" refers to a tumor either confined to the pancreas or growing outside the pancreas but has not spread into nearby large blood vessels or major nerves. Stage IIB may spread to nearby lymph nodes but has not spread to distant sites.

"Stage III pancreatic cancer" as used herein refers to wider spread cancer that has expanded into nearby major blood vessels or nerves but has not metastasized. The tumor is growing outside the pancreas into nearby large blood vessels or major nerves and may or may not have spread to nearby lymph nodes. It has not spread to distant sites.

"Stage IV pancreatic cancer" as used herein refers to confirmed spread cancer that has spread to distant organs or sites. Stage IVA pancreatic cancer is locally confined, but involves adjacent organs or blood vessels, thereby hindering surgical removal. Stage IVA pancreatic cancer is also referred to as localized or locally advanced. Stage IVB pancreatic cancer has spread to distant organs, most commonly the liver. Stage IVB pancreatic cancer is also called metastatic.

"Predetermined cutoff" and "predetermined level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein, is one that lyses any cells and/or solubilizes any analyte that is/are present in a test sample. Pretreatment is not necessary for all samples, as described further herein. Among other things, solubilizing the analyte (i.e., laminin gamma 2 monomer, PIKVA-II, AFP, CEA, and/or CA19-9, fragments of laminin gamma 2 monomer, PIVKA-II, AFP, CEA, and/or CA19-9, variants of laminin gamma 2 monomer, PIVKA-II, AFP, CEA, and/or CA19-9, or any combinations thereof) entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "biological sample," "test sample," "specimen," "sample from a subject," "sample obtained from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

The term "sensitivity" as used herein refers to the number of true positives divided by the number of true positives plus the number of false negatives, where sensitivity ("sens") may be within the range of 0<sens<1. Ideally, method embodiments herein have the number of false negatives equaling zero or close to equaling zero, so that no subject is wrongly identified as not having hepatocellular carcinoma or pancreatic cancer when they indeed have hepatocellular carcinoma or pancreatic cancer. Conversely, an assessment often is made of the ability of a prediction algorithm to classify negatives correctly, a complementary measurement to sensitivity.

The term "specificity" as used herein refers to the number of true negatives divided by the number of true negatives plus the number of false positives, where specificity ("spec") may be within the range of 0<spec<1. Ideally, the methods described herein have the number of false positives equaling zero or close to equaling zero, so that no subject is wrongly identified as having adenoma when they do not in fact have hepatocellular carcinoma or pancreatic cancer. Hence, a method that has both sensitivity and specificity equaling one, or 100%, is preferred.

"Series of calibrating compositions" refers to a plurality of compositions comprising a known concentration of laminin gamma 2 monomer, PIVKA-II, AFP, CEA, and/or CA19-9, wherein each of the compositions differs from the other compositions in the series by the concentration of laminin gamma 2 monomer, PIVKA-II, AFP, CEA, and/or CA19-9.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human. In some embodiments, the subject or subject may be a human or a non-human. In some embodiments, the subject may be a human subject at risk or suspected at being at risk for developing or already having hepatocellular carcinoma and/or pancreatic cancer, or a cancer other than hepatocellular carcinoma or pancreatic cancer.

The terms "treat," "treated," or "treating" as used herein refers to a therapeutic wherein the object is to slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or a fragment thereof that has been differentially processed, such as by proteolysis, phosphorylation, or other post-translational modification, yet retains its antigen reactivity.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Method of Diagnosing a Disease Using Laminin Gamma 2 Monomer

Provided herein is a method of diagnosing a disease, such as hepatocellular carcinoma (HCC) or pancreatic cancer, in a subject in need thereof. The method includes obtaining a sample from the subject, determining a level of laminin gamma 2 monomer in the sample, and comparing the level of laminin gamma 2 monomer in the sample to a reference level of laminin gamma 2 monomer. A change in the level of laminin gamma 2 monomer in the sample obtained from the subject relative to a reference level indicates the subject is suffering from or is at risk of suffering from the disease. In some embodiments, the change in the level of laminin gamma 2 monomer may be an increase in the level of laminin gamma 2 monomer in the sample obtained from the subject relative to the reference level. Such an increase in the level of laminin gamma 2 monomer may indicate that the subject is suffering from or is at risk of suffering from the disease.

The method of diagnosing may also include determining a level of at least one additional biomarker, such as PIVKA-II, AFP, CEA, CA19-9, or combinations thereof, in the sample from the subject and comparing the level of the at least one additional biomarker in the sample to a reference level of the at least one additional biomarker. A change in the levels of laminin gamma 2 monomer and the at least one additional biomarker in the sample obtained from the subject relative to the reference levels may also indicate the subject is suffering from or is at risk of suffering from the disease. In some embodiments, the change in the level of laminin gamma 2 monomer and the at least one additional biomarker may be an increase in the levels of laminin gamma 2 monomer and the at least one additional biomarker in the sample obtained from the subject relative to the reference level. Such an increase in the levels of laminin gamma 2 monomer and the at least one additional biomarker may further indicate that the subject is suffering from or is at risk of suffering from the disease.

a. Laminin Gamma 2 Monomer

The method of diagnosing a disease, such as hepatocellular carcinoma (HCC) or pancreatic cancer, includes measuring the levels of laminin gamma 2 monomer in a sample from a subject. Laminin gamma 2 monomer (also referred to herein as "laminin gamma 2" or "Ln-γ2") is a member of the laminin family of proteins, which are extracellular matrix glycoproteins and constituents of basement membranes. Each heterotrimeric laminin is composed of three non-identical chains: laminin alpha, laminin beta, and laminin gamma. Different alpha, beta, and gamma chain isomers may be combined to give rise to different heterotrimeric laminin isoforms. Laminin gamma 2 is one gamma chain isomer and together with laminin alpha 3 and laminin beta 3 forms laminin 5. Laminin 5 is predominantly localized in basil lamina and basement membrane. In humans, laminin gamma 2 monomer is encoded by the LAMC2 gene, which is located on the long (q) arm of human chromosome 1 between positions 25 and 31 (1q25-1q31). Human laminin gamma 2 monomer may be a precursor protein, which includes the signal peptide, or the secreted protein, in which the signal peptide has been removed by cleavage.

b. Additional Biomarkers

The method of diagnosing a disease, such as hepatocellular carcinoma (HCC) or pancreatic cancer, may include measuring the levels of laminin gamma 2 monomer and the levels of at least one additional biomarker in the sample from the subject. The at least one additional biomarker may be protein induced vitamin K antagonist-II (PIVKA-II), alpha fetal protein (AFP), carcinoembryonic antigen (CEA), car antigen 19-9 (CA19-9), or any combination thereof.

(1) Protein Induced Vitamin K Antagonist-II (PIVKA-II)

The method of diagnosing a disease, such as hepatocellular carcinoma (HCC), may include measuring the levels of laminin gamma 2 monomer and the levels of protein induced vitamin K antagonist-II (PIVKA-II). PIVKA-II (also known as des-g-carboxy prothrombin (DCP)) is an abnormal form of the coagulation protein prothrombin. PIVKA-II is the least sensitive to risk factors for HCC (such as cirrhosis), and hence useful in predicting HCC. It differentiates HCC from non-malignant liver diseases; however, false increases of PIVKA-II concentrations are found in patients with severe obstructive jaundice due to intrahepatic cholestasis, or under conditions in which the action of vitamin K is impaired in individuals with long standing vitamin K deficiency, and in those who have ingested Warfarin or wide spectrum antibiotics.

(2) Alpha Fetal Protein (AFP)

The method of diagnosing a disease, such as hepatocellular carcinoma (HCC), may include measuring the levels of laminin gamma 2 monomer and the levels of alpha fetal protein (AFP). AFP (also known as α-fetoprotein, alpha-1-fetoprotein, alpha-fetoglobulin, and alpha-fetoprotein) is a major plasma protein produced by the yolk sac and the liver during fetal development and is thought to be the fetal form of serum albumin. In humans, AFP is encoded by the AFP gene, which is located on the long (q) arm of chromosome 4. AFP binds to copper, nickel, fatty acids, and bilirubin and is found in monomeric, dimeric, and trimeric forms. AFP is a glycoprotein of 591 amino acids and a carbohydrate moiety. AFP may be detected and quantified using Abbott ARCHITECT® AFP.

(3) Carcinoembryonic Antigen (CEA)

The method of diagnosing a disease, such as pancreatic cancer, may include measuring the levels of laminin gamma 2 monomer and the levels of carcinoembryonic antigen (CEA). CEA is involved in cell adhesion and is a glycosyl phosphatidyl inositol (GPI)-cell surface anchored glycoprotein whose specialized sialofucosylated glycoforms serve as functional colon carcinoma L-selectin and E-selectin ligands. CEA is a tumor associated antigen that is characterized by a glycoprotein that is approximately 200 kDa in size. CEA is FDA approved and intended to be used as an aid in the prognosis and management of cancer patients with changing concentrations of CEA.

Additionally, CEA is a marker related to colorectal cancer (CRC) and has been clinically approved for monitoring gastrointestinal (GI) cancers including CRC. Its performance to detect some CRC has been characterized. Clinical relevance has been shown in colorectal, gastric, lung, prostate, pancreatic, and ovarian cancers (Abbott ARCHITECT CEA Package Insert 34-4067/R4). CEA may be detected and quantified using Abbott ARCHITECT® CEA.

(4) Carbohydrate Antigen 19-9 (CA19-9)

The method of diagnosing a disease, such as pancreatic cancer, may include measuring the levels of laminin gamma 2 monomer and the levels of carbohydrate antigen 19-9 (CA19-9 or CA19-9). CA19-9 is a mucin-glycoprotein derived from a human colorectal carcinoma cell line and is related to the Lewis blood group protein. Specifically, CA19-9 belongs to the sialylated Lewis blood group antigen and may be undetectable in individuals that are Lewis antigen negative. Additionally, CA19-9 is present in the epithelial tissue of the stomach, gall bladder, pancreas, and prostate.

CA19-9 has been FDA approved for use as an aid in the management of pancreatic cancer and is intended to be used in conjunction with other diagnostic information such as computed tomography (CT) and magnetic resonance imaging (MRI) procedures. Serum CA19-9 may also be elevated in patients with nonmalignant conditions such as pancreatitis and other gastrointestinal disorders (Abbott ARCHITECT CA19-9 XR Package Insert 015-550 11/05). Elevated levels of CA19-9 may be informative for some colorectal (CRC) cancers. CA19-9 may be detected and quantified using Abbott ARCHITECT® CA19-9 XR.

c. Combinations of Laminin Gamma 2 Monomer and Additional Biomarkers

As described above, the method of a disease, such as hepatocellular carcinoma (HCC) or pancreatic cancer, may include measuring the levels of laminin gamma 2 monomer and the levels of at least one additional biomarker in the sample obtained from the subject. An increase in the levels of laminin gamma 2 monomer and the levels of the at least one additional biomarker relative to the reference level may indicate that the subject is suffering from or is at risk of suffering from the disease.

In some embodiments, the method of diagnosing may detect levels of laminin gamma 2 monomer, PIVKA-II, AFP, CEA, or CA19-9, or combinations thereof in the sample obtained from the subject. An increase in the levels of laminin gamma 2 monomer, PIVKA-II, AFP, CEA, or CA19-9, or combinations thereof, relative to the reference level may indicate that the subject is suffering from or is at risk of suffering from the disease.

In other embodiments, the method of diagnosing may detect levels of laminin gamma 2 monomer and PIVKA-II in the sample obtained from the subject. An increase in the levels of laminin gamma 2 monomer and PIVKA-II relative to the reference level may indicate that the subject is suffering from or is at risk of suffering from the disease (e.g., hepatocellular carcinoma (HCC)).

In still other embodiments, the method of diagnosing may detect levels of laminin gamma 2 monomer and AFP in the sample obtained from the subject. An increase in the levels of laminin gamma 2 monomer and AFP relative to the reference level may indicate that the subject is suffering from or is at risk of suffering from the disease (e.g., HCC).

In other embodiments, the method of diagnosing may detect levels of laminin gamma 2 monomer, PIVKA-II, and AFP in the sample obtained from the subject. An increase in the levels of laminin gamma 2 monomer, PIVKA-II, and AFP relative to the reference level may indicate that the subject is suffering from or is at risk of suffering from the disease (e.g., HCC).

In some embodiments, the method of diagnosing may detect levels of laminin gamma 2 monomer and CEA in the sample obtained from the subject. An increase in the levels of laminin gamma 2 monomer and CEA relative to the reference level may indicate that the subject is suffering from or is at risk of suffering from the disease (e.g., pancreatic cancer).

In other embodiments, the method of diagnosing may detect levels of laminin gamma 2 monomer and CA19-9 in the sample obtained from the subject. An increase in the levels of laminin gamma 2 monomer and CA19-9 relative to the reference level may indicate that the subject is suffering from or is at risk of suffering from the disease (e.g., pancreatic cancer).

In still other embodiments, the method of diagnosing may detect levels of laminin gamma 2 monomer, CEA, and CA19-9 in the sample obtained from the subject. An increase in the levels of laminin gamma 2 monomer, CEA, and CA19-9 relative to the reference level may indicate that the subject is suffering from or is at risk of suffering from the disease (e.g., pancreatic cancer).

d. Disease

The method described herein may be used to provide a diagnosis of a subject having a disease by determining the levels of laminin gamma 2 monomer and/or at least one additional biomarker in a sample obtained from the subject. A change in the level of laminin gamma 2 monomer and/or the at least one additional biomarker in the sample obtained from the subject relative to the reference level indicates the subject is suffering from or is at risk of suffering from the disease. The disease may be hepatocellular carcinoma (HCC) or pancreatic cancer.

(1) Hepatocellular Carcinoma (HCC)

The method described herein may be used to provide a diagnosis of a subject having hepatocellular carcinoma (HCC). HCC (also be known as malignant hepatoma) is the most common type of liver cancer and many cases of HCC are secondary to a viral hepatitis infection (hepatitis B or C) or liver cirrhosis. When the disease is hepatocellular carcinoma (HCC), the method of diagnosing may determine the level of laminin gamma 2 monomer and/or the level of at least one additional biomarker in the sample obtained from the subject. A change in the level of laminin gamma 2 monomer and/or the level of at least one additional biomarker relative to the reference level indicates that the subject is suffering from or is at risk of suffering from HCC. Such a change may be an increase in the level of laminin gamma 2 monomer and/or the level of at least one additional biomarker relative to the reference level. In some embodiments, the at least one additional biomarker may be AFP, PIVKA-II, or a combination thereof.

In some embodiments, the method of diagnosing may measure the level of laminin gamma 2 monomer in the sample obtained from the subject. A change in the level of laminin gamma 2 monomer relative to the reference level indicates that the subject is suffering from or is at risk of suffering from HCC. The change in the level of laminin gamma 2 monomer relative to the reference level may be such that the level of laminin gamma 2 monomer in the sample obtained from the subject is increased relative to the reference level.

In other embodiments, the method of diagnosing may measure the levels of laminin gamma 2 monomer and AFP in the sample obtained from the subject. A change in the levels of laminin gamma 2 monomer and AFP relative to the reference level indicates that the subject is suffering from or is at risk of suffering from HCC. The change in the levels of laminin gamma 2 monomer and AFP relative to the reference level may be such that the levels of laminin gamma 2 monomer and AFP in the sample obtained from the subject are increased relative to the reference level.

In still other embodiments, the method of diagnosing may measure the levels of laminin gamma 2 monomer and PIVKA-II in the sample obtained from the subject. A change in the levels of laminin gamma 2 monomer and PIVKA-II relative to the reference level indicates that the subject is suffering from or is at risk of suffering from HCC. The change in the levels of laminin gamma 2 monomer and PIVKA-II relative to the reference level may be such that the levels of laminin gamma 2 monomer and PIVKA-II in the sample obtained from the subject are increased relative to the reference level.

In other embodiments, the method of diagnosing may measure the levels of laminin gamma 2 monomer, AFP, and PIVKA-II in the sample obtained from the subject. A change in the levels of laminin gamma 2 monomer, AFP, and PIVKA-II relative to the reference level indicates that the subject is suffering from or is at risk of suffering from HCC. The change in the levels of laminin gamma 2 monomer, AFP, and PIVKA-II relative to the reference level may be such that the levels of laminin gamma 2 monomer, AFP, and PIVKA-II in the sample obtained from the subject are increased relative to the reference level.

(a) Stage of HCC

The method described herein may be used to provide a diagnosis of a subject having hepatocellular carcinoma (HCC) at a particular stage. The disease may be stage I HCC, stage II HCC, stage III HCC (including stage IIIA HCC, stage IIIB HCC, and stage IIIC HCC), or stage IV HCC (including stage IVA HCC and stage IVB HCC). The level of laminin gamma 2 monomer may increase with the stage of HCC. As such, the level of laminin gamma 2 monomer may be higher in stage II HCC, stage III HCC, or stage IV HCC than the level of laminin gamma 2 monomer in stage I HCC. The level of laminin gamma 2 monomer may be higher in stage III HCC or stage IV HCC than the level of laminin gamma 2 monomer in stage I HCC or stage II HCC. The level of laminin gamma 2 monomer may be higher in stage IV HCC than the level of laminin gamma 2 monomer in stage I HCC, stage II HCC, or stage III HCC. Accordingly, increasing levels of laminin gamma 2 monomer may indicate that the HCC is progressing from one stage to another stage in subject.

(2) Pancreatic Cancer

The method described herein may be used to provide a diagnosis of a subject having pancreatic cancer. Pancreatic cancer is cancer that originates in the pancreas. Pancreatic cancer may include, but is not limited to, exocrine pancreatic cancer, such as pancreatic adenocarcinoma, acinar cell carcinoma, adenocarcinoma, adenosquamous carcinoma, giant cell tumor, mucinous cystadenocarcinoma, pancreatoblastoma, serous cystadenocarcinoma, solid and pseudopapillary tumors, and papillar cystic neoplasms, endocrine pancreatic cancer, such as pancreatic neuroendocrine tumors (NET), islet cell tumors, islet cell carcinoma, pancreatic carcinoid, pancreatic endocrine tumor (PET), gastrinoma (Zollinger-Ellison Syndrome), glucagonoma, insulinoma, nonfunctional islet cell tumor, somatostatinoma, and vasoactive intestinal peptide-releasing tumor (VIPoma or Vemer-Morrison Syndrome), and lymphoma of the pancreas. Adenocarcinoma may develop from a benign intraductal papillary-mucinous neoplasm (IPMN).

When the disease is pancreatic cancer, the method of diagnosing may determine the level of laminin gamma 2 monomer and/or the level of at least one additional biomarker in the sample obtained from the subject. A change in the level of laminin gamma 2 monomer and/or the level of at least one additional biomarker relative to the reference level indicates that the subject is suffering from or is at risk of suffering from pancreatic cancer. Such a change may be an increase in the level of laminin gamma 2 monomer and/or the level of at least one additional biomarker relative to the reference level. In some embodiments, the at least one additional biomarker may be CEA, CA19-9, or a combination thereof.

In some embodiments, the method of diagnosing may measure the level of laminin gamma 2 monomer in the sample obtained from the subject. A change in the level of laminin gamma 2 monomer relative to the reference level indicates that the subject is suffering from or is at risk of suffering from pancreatic cancer. The change in the level of laminin gamma 2 monomer relative to the reference level may be such that the level of laminin gamma 2 monomer in the sample obtained from the subject is increased relative to the reference level.

In other embodiments, the method of diagnosing may measure the levels of laminin gamma 2 monomer and CEA in the sample obtained from the subject. A change in the levels of laminin gamma 2 monomer and CEA relative to the reference level indicates that the subject is suffering from or is at risk of suffering from pancreatic cancer. The change in the levels of laminin gamma 2 monomer and CEA relative to the reference level may be such that the levels of laminin gamma 2 monomer and CEA in the sample obtained from the subject are increased relative to the reference level.

In still other embodiments, the method of diagnosing may measure the levels of laminin gamma 2 monomer and CA19-9 in the sample obtained from the subject. A change in the levels of laminin gamma 2 monomer and CA19-9 relative to the reference level indicates that the subject is suffering from or is at risk of suffering from pancreatic cancer. The change in the levels of laminin gamma 2 monomer and CA19-9 relative to the reference level may be such that the levels of laminin gamma 2 monomer and CA19-9 in the sample obtained from the subject are increased relative to the reference level.

In other embodiments, the method of diagnosing may measure the levels of laminin gamma 2 monomer, CEA, and CA19-9 in the sample obtained from the subject. A change in the levels of laminin gamma 2 monomer, CEA, and CA19-9 relative to the reference level indicates that the subject is suffering from or is at risk of suffering from pancreatic cancer. The change in the levels of laminin gamma 2 monomer, CEA, and CA19-9 relative to the reference level may be such that the levels of laminin gamma 2 monomer, CEA, and CA19-9 in the sample obtained from the subject are increased relative to the reference level.

(a) Stage of Pancreatic Cancer

The method described herein may be used to provide a diagnosis of a subject having pancreatic cancer at a particular stage. The disease may be stage 0 pancreatic cancer, stage I pancreatic cancer, stage II pancreatic cancer, stage III pancreatic cancer, or stage IV pancreatic cancer. The level of the laminin gamma 2 monomer may increase with the stage of pancreatic cancer. For example, the level of laminin gamma 2 monomer may be higher in stage IV pancreatic cancer than the level of laminin gamma 2 monomer in stage III pancreatic cancer. Accordingly, increasing levels of laminin gamma 2 monomer may indicate that the pancreatic cancer is progressing from one stage to another stage in the subject.

e. Immunoassay to Determine Laminin Gamma 2 Monomer and/or the at Least One Additional Biomarker Levels The method of diagnosing may employ an immunoassay to determine the levels laminin gamma 2 monomer and/or the at least one additional biomarker in the sample obtained from the subject. The immunoassay may quantify levels of laminin gamma 2 monomer and/or the at least one additional biomarker.

The presence or amount of laminin gamma 2 monomer and/or the at least one additional biomarker can be determined using antibodies that specifically bind to each biomarker (e.g., laminin gamma 2 monomer, PIVKA-II, AFP, CEA, and/or CA19-9 as well as any additional analytes if such additional analytes are used). Examples of antibodies that can be used include a polyclonal antibody, a monoclonal antibody, a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multi-specific antibody, a Fab, a dual specific antibody, a DVD, a Fab', a bispecific antibody, a F(ab')2, a Fv, and combinations thereof.

For example, the immunological method may include (a) measuring the level of laminin gamma 2 monomer by: (i) contacting the test sample with at least one capture antibody, wherein the capture antibody binds to an epitope on laminin gamma 2 monomer or a fragment of laminin gamma 2 monomer to form a capture antibody-laminin gamma 2 monomer complex; (ii) contacting the capture antibody-laminin gamma 2 monomer complex with at least one detection antibody comprising a detectable label, wherein the detection antibody binds to an epitope on laminin gamma 2 monomer that is not bound by the capture antibody and forms a capture antibody-laminin gamma 2 monomer-detection antibody complex; and (iii) determining the level of laminin gamma 2 monomer in the test sample based on the signal generated by the detectable label in the capture antibody-laminin gamma 2 monomer-detection antibody complex formed in (a)(ii); (b) measuring the level of the at least one additional biomarker by: (i) contacting the test sample with at least one capture antibody, wherein the capture antibody binds to an epitope on the at least one additional biomarker or a fragment of the at least one additional biomarker to form a capture antibody—at least one additional biomarker complex; (ii) contacting the capture antibody—at least one additional biomarker complex with at least one detection antibody comprising a detectable label, wherein the detection antibody binds to an epitope on the s at least one additional biomarker that is not bound by the capture antibody and forms a capture antibody—at least one additional biomarker-detection antibody complex; and (iii) determining the level of the at least one additional biomarker in the test sample based on the signal generated by the detectable label in the capture antibody—at least one additional biomarker-detection antibody complex formed in (b)(ii); or a combination thereof.

Any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA. Specific immunological binding of the antibody to the marker can be detected via direct labels, such as fluorescent or luminescent tags, metals and radionuclides attached to the antibody or via indirect labels, such as alkaline phosphatase or horseradish peroxidase.

The use of immobilized antibodies or fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and then processed quickly through washes and detection steps to generate a measurable signal, such as a colored spot.

The sandwich ELISA measures the amount of antigen between two layers of antibodies (i.e. a capture antibody and a detection antibody (which may be labeled with a detectable label)). The laminin gamma 2 monomer and/or at least one additional biomarker, i.e., PIVKA-II, AFP, CEA, and/or CA19-9, to be measured may contain at least two antigenic sites capable of binding to antibody. Either monoclonal or polyclonal antibodies may be used as the capture and detection antibodies in the sandwich ELISA.

Generally, at least two antibodies are employed to separate and quantify laminin gamma 2 monomer or the at least one additional biomarker, i.e., PIVKA-II, AFP, CEA, and/or CA19-9 (as well as any additional analytes), in a test or biological sample. More specifically, the at least two antibodies bind to certain epitopes of laminin gamma 2 monomer or the at least one additional biomarker forming an immune complex which is referred to as a "sandwich". One or more antibodies can be used to capture the laminin gamma 2 monomer or the at least one additional biomarker in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, both antibodies binding to their epitope may not be diminished by the binding of any other antibody in the assay to its respective epitope. In other words, antibodies may be selected so that the one or more first antibodies brought into contact with a test sample suspected of containing laminin gamma 2 monomer or the at least one additional biomarker do not bind to all or part of an epitope recognized by the second or subsequent antibodies, thereby interfering with the ability of the one or more second detection antibodies to bind to laminin gamma 2 monomer or the at least one additional biomarker.

In a preferred embodiment, a test or biological sample suspected of containing laminin gamma 2 monomer and/or the at least one additional biomarker, i.e., PIVKA-II, AFP, CEA, and/or CA19-9, can be contacted with at least one first capture antibody (or antibodies) and at least one second detection antibodies either simultaneously or sequentially. In the sandwich assay format, a test sample suspected of containing laminin gamma 2 monomer and/or the at least one additional biomarker is first brought into contact with the at least one first capture antibody that specifically binds to a particular epitope under conditions which allow the formation of a first antibody-laminin gamma 2 monomer or—at least one additional biomarker complex. If more than one capture antibody is used, a first multiple capture antibody-laminin gamma 2 monomer or—at least one additional biomarker complex is formed. In a sandwich assay, the antibodies, preferably, the at least one capture antibody, are used in molar excess amounts of the maximum amount of laminin gamma 2 monomer or the at least one additional biomarker expected in the test sample.

Optionally, prior to contacting the test sample with the at least one first capture antibody, the at least one first capture antibody can be bound to a solid support which facilitates the separation the first antibody-laminin gamma 2 monomer or—at least one additional biomarker complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind the marker. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing laminin gamma 2 monomer and/or at least one additional biomarker is brought into contact with the at least one first capture antibody, the test sample is incubated in order to allow for the formation of a first capture antibody (or multiple antibody)-laminin gamma 2 monomer or—at least one additional biomarker complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the first/multiple capture antibody-laminin gamma 2 monomer or at least one additional biomarker complex, the complex is then contacted with at least one second detection antibody (under conditions which allow for the formation of a first/multiple antibody-laminin gamma 2 monomer or—at least one additional biomarker-second antibody complex). If the first antibody-laminin gamma 2 monomer or—at least one additional biomarker complex is contacted with more than one detection antibody, then a first/multiple capture antibody-laminin gamma 2 monomer or—at least one additional biomarker multiple antibody detection complex is formed. As with first antibody, when the at least second (and subsequent) antibody is brought into contact with the first antibody-laminin gamma 2 monomer or—at least one additional biomarker complex, a period of incubation under conditions similar to those described above is required for the formation of the first/multiple antibody-laminin gamma 2 monomer or—at least one additional biomarker/multiple antibody complex. Preferably, at least one second antibody contains a detectable label. The detectable label can be bound to the at least one second antibody prior to, simultaneously with or after the formation of the first/multiple antibody-laminin gamma 2 monomer or—at least one additional biomarker/multiple antibody complex. Any detectable label known in the art can be used.

f. Reference Level

The method of diagnosing described herein may use the reference levels of laminin gamma 2 monomer and/or the at least one additional biomarker to identify and determine whether or not a subject is suffering from or is at risk of suffering from the disease. Levels of laminin gamma 2 monomer and/or the at least one additional biomarker measured in the sample obtained from the subject and greater than the respective reference levels may identify the subject as suffering from or at risk of suffering from the disease. Levels of laminin gamma 2 monomer and/or the at least one additional biomarker less than or equal to the respective reference levels may identify the subject as not suffering from or at risk of suffering from the disease.

(1) Reference Levels for Laminin Gamma 2 Monomer, PIVKA-II, AFP, CEA, and/or CA19-9

Generally, predetermined or reference levels can be employed as a benchmark against which to assess results obtained upon assaying a test sample for laminin gamma 2 monomer, PIVKA-II, AFP, CEA, CA19-9, or combinations thereof. Generally, in making such a comparison, the predetermined levels are obtained by running a particular assay a sufficient number of times and under appropriate conditions such that a linkage or association of the analyte presence, amount or concentration with a particular stage or endpoint of the disease with particular indicia can be made. Typically, the predetermined levels are obtained with assays of reference subjects (or populations of subjects). The reference subject may be a control subject. The reference population or reference group may be a control group. The laminin gamma 2 monomer, PIVKA-II, AFP, CEA, and/or CA19-9 measured can include laminin gamma 2 monomer, PIVKA-II, AFP, CEA, and/or CA19-9 fragments thereof, degradation products thereof, and/or enzymatic cleavage products thereof.

In particular, with respect to predetermined levels as employed for monitoring disease progression and/or treatment, the amount or concentration of laminin gamma 2 monomer, PIVKA-II, AFP, CEA, and/or CA19-9 fragments may be "unchanged," "favorable" (or "favorably altered"), or "unfavorable" (or "unfavorably altered"). "Elevated" or "increased" refers to an amount or a concentration in a test sample that is higher or greater than a typical or normal level or range (e.g., predetermined level), such as a typical or normal level found in a control group or control sample, or is higher or greater than another reference level or range (e.g., earlier or baseline sample). The term "lowered" or "reduced" refers to an amount or a concentration in a test sample that is lower or less than a typical or normal level or range (e.g., predetermined level), such as a typical or normal level found in a control group or control sample, or is lower or less than another reference level or range (e.g., earlier or baseline sample). The term "altered" refers to an amount or a concentration in a sample that is altered (increased or decreased) over a typical or normal level or range (e.g., predetermined level), such as a typical or normal level found in a control group or control sample, or over another reference level or range (e.g., earlier or baseline sample).

The typical or normal levels or ranges for laminin gamma 2 monomer, PIVKA-II, AFP, CEA, and/or CA19-9 are defined in accordance with standard practice. A so-called altered level or alteration can be considered to have occurred when there is any net change as compared to the typical or normal level or range, or reference level or range that cannot be explained by experimental error or sample variation. In some embodiments, the level measured in a particular sample will be compared with the level or range of levels determined in similar samples from a so-called normal subject, i.e., control subject. In this context, a "normal" (sometimes termed "control" or "healthy") subject is an individual with no detectable HCC or pancreatic cancer, and a "normal" patient or population is/are one(s) that exhibit(s) no detectable HCC or pancreatic cancer, for example. An "apparently normal subject" is one in which laminin gamma 2 monomer, PIKVA-II, AFP, CEA, and/or CA19-9 has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level.

In one embodiment, the reference level for laminin gamma 2 monomer in serum may be about 81.3 pg/mL. In another embodiment, the reference level for laminin gamma 2 monomer in serum may be 81.3 pg/mL. In one embodiment, the reference level for laminin gamma 2 monomer in serum may be about 79.5 pg/mL. In another embodiment, the reference level for laminin gamma 2 monomer in serum may be 79.5 pg/mL. In other embodiments, the reference level for laminin gamma 2 monomer in serum may be about 70.0 pg/mL, 71.0 pg/mL, 72.0 pg/mL, 73.0 pg/mL, 74.0 pg/mL, 75.0 pg/mL, 76.0 pg/mL, 76.3 pg/mL, 76.4 pg/mL, 76.5 pg/mL, 76.6 pg/mL, 76.7 pg/mL, 76.8 pg/mL, 76.9 pg/mL, 77.0 pg/mL, 78.0 pg/mL, 79.0 pg/mL, 79.1 pg/mL, 79.2 pg/mL, 79.3 pg/mL, 79.4 pg/mL, 79.5 pg/mL, 79.6 pg/mL, 79.7 pg/mL, 79.8 pg/mL, 79.9 pg/mL, 80.0 pg/mL, 80.1 pg/mL, 80.2 pg/mL, 80.3 pg/mL, 80.4 pg/mL, 80.5 pg/mL, 80.6 pg/mL, 80.7 pg/mL, 80.8 pg/mL, 80.9 pg/mL. 81.0 pg/mL, 81.1 pg/mL, 81.2 pg/mL, 81.3 pg/mL, 81.4 pg/mL, 81.5 pg/mL, 81.6 pg/mL, 81.7 pg/mL, 81.8 pg/mL, 81.9 pg/mL, 82.0 pg/mL, 82.1 pg/mL, 82.3 pg/mL, 82.4 pg/mL, 82.5 pg/mL, 82.6 pg/mL, 82.7 pg/mL, 82.8 pg/mL, 82.9 pg/mL, 83.0 pg/mL, 84.0 pg/mL, 85.0 pg/mL, 86.0 pg/mL, 87.0 pg/mL, 88.0 pg/mL, 89.0 pg/mL, 90.0 pg/mL, 91.0 pg/mL, 92.0 pg/mL, 93.0 pg/mL, 94.0 pg/mL, 95.0 pg/mL, 96.0 pg/mL, 97.0 pg/mL, 98.0 pg/mL, 99.0 pg/mL, 100.0 pg/mL, 101.0 pg/mL, 102.0 pg/mL, 103.0 pg/mL, 104.0 pg/mL, 105.0 pg/mL, 106.0 pg/mL, 107.0 pg/mL, 108.0 pg/mL, 109.0 pg/mL, 110.0 pg/mL, 111.0 pg/mL, 112.0 pg/mL, 113.0 pg/mL, 114.0 pg/mL, 115.0 pg/mL, 115.05 pg/mL, 116.0 pg/mL, 116.4 pg/mL, 116.5 pg/mL, 116.6 pg/mL, 116.7 pg/mL, 116.8 pg/mL, 116.9 pg/mL, 117.0 pg/mL, 118.0 pg/mL, 119.0 pg/mL, 120.0 pg/mL.

In one embodiment, the reference level for PIVKA-II in serum may be about 40 mAU/mL. In another embodiment, the reference level for PIVKA-II in serum may be 40 mAU/mL. In other embodiments, the reference level for PIVKA-II in serum may be about 30 mAU/mL, 31 mAU/mL, 32 mAU/mL, 33 mAU/mL, 34 mAU/mL, 35 mAU/mL, 36 mAU/mL, 37 mAU/mL, 38 mAU/mL, 39 mAU/mL, 40 mAU/mL, 41 mAU/mL, 42 mAU/mL, 43 mAU/mL, 44 mAU/mL, 45 mAU/mL, 46 mAU/mL, 47 mAU/mL, 48 mAU/mL, 49 mAU/mL, or 50 mAU/mL.

In one embodiment, the reference level for AFP in serum may be about 20 ng/mL. In another embodiment, the reference level for AFP in serum may be 20 ng/mL. In other embodiments, the reference level for AFP in serum may be about 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, or 30 ng/mL.

In one embodiment, the reference level for CEA may be about 5.0 ng/mL. In another embodiment, the reference level for CEA in serum may be 5.0 ng/mL. In other embodiments, the reference level for CEA in serum may be about 1.0 ng/mL, 1.5 ng/mL, 2.0 ng/mL, 2.5 ng/mL, 3.0 ng/mL, 3.5 ng/mL, 4.0 ng/mL, 4.5 ng/mL, 5.0 ng/mL, 5.5 ng/mL, 6.0 ng/mL, 6.5 ng/mL, 7.0 ng/mL, 7.5 ng/mL, 8.0 ng/mL, 8.5 ng/mL, 9.0 ng/mL, 9.5 ng/mL, or 10.0 ng/mL.

In one embodiment, the reference level for CA19-9 in serum may be about 37.0 U/mL. In another embodiment, the reference level for CA19-9 in serum may be 37.0 U/mL. In other embodiments, the reference level for CA19-9 in serum may be about 27.0 U/mL, 27.5 U/mL, 28.0 U/mL, 28.5 U/mL, 29.0 U/mL, 29.5 U/mL, 30.0 U/mL, 30.5 U/mL, 31.0 U/mL, 31.5 U/mL, 32.0 U/mL, 32.5 U/mL, 33.0 U/mL, 33.5 U/mL, 34.0 U/mL, 34.5 U/mL, 35.0 U/mL, 35.5 U/mL, 36.0 U/mL, 36.5 U/mL, 37.0 U/mL, 37.5 U/mL, 38.0 U/mL, 38.5 U/mL, 39.0 U/mL, 39.5 U/mL, 40.0 U/mL, 40.5 U/mL, 41.0 U/mL, 41.5 U/mL, 42.0 U/mL, 42.5 U/mL, 43.0 U/mL, 43.5 U/mL, 44.0 U/mL, 44.5 U/mL, 45.0 U/mL, 45.5 U/mL, 46.0 U/mL, 46.5 U/mL, or 47.0 U/mL.

Cutoff values (or predetermined cutoff values) may be determined by Adaptive Index Model (AIM) methodology.

Cutoff values (or predetermined cutoff values) may be determined by a receiver operating curve (ROC) analysis from biological samples of the patient group. ROC analysis, as generally known in the biological arts, is a determination of the ability of a test to discriminate one condition from another, e.g., to determine the performance of each marker in identifying a patient having CRC. A description of ROC analysis as applied according to the present disclosure is provided in P. J. Heagerty et al., Time-dependent ROC curves for censored survival data and a diagnostic marker, Biometrics 56:337-44(2000), the disclosure of which is hereby incorporated by reference in its entirety.

Alternatively, cutoff values can be determined by a quartile analysis of biological samples of a patient group. For example, a cutoff value can be determined by selecting a value that corresponds to any value in the 25th-75th percentile range, preferably a value that corresponds to the 25th percentile, the 50th percentile or the 75th percentile, and more preferably the 75th percentile.

Such statistical analyses can be performed using any method known in the art and can be implemented through any number of commercially available software packages (e.g., from Analyse-it Software Ltd., Leeds, UK; StataCorp LP, College Station, Tex.; SAS Institute Inc., Cary, N.C.).

3. Method of Determining Risk of Developing the Disease

Also provided herein is a method of determining if a subject is at risk of developing the disease. The method of determining risk may apply the method of diagnosing described above to determine if the subject is at risk of developing the disease.

The method of determining risk may include obtaining a biological sample from the subject and measuring a level of laminin gamma 2 monomer in the biological sample. The method of determining risk may also include comparing the level of laminin gamma 2 monomer in the biological sample to the reference level of laminin gamma 2 monomer, and determining the subject is at risk of developing the disease when the level of laminin gamma 2 monomer in the biological sample is greater than the reference level of laminin gamma 2 monomer.

The method of determining risk may further include determining a level of at least one additional biomarker in the biological sample and comparing the level of the at least one additional biomarker in the biological sample to the reference level of the at least one additional biomarker. The subject may also be identified as being at risk of developing the disease when the level of laminin gamma 2 monomer and the at least one additional biomarker in the biological sample is greater than the reference level of laminin gamma 2 monomer and the reference level of the at least one additional biomarker, respectively.

4. Method of Monitoring Progression of the Disease

Also provided herein is a method of monitoring progression of the disease in a subject in need thereof. The method of monitoring may apply the method of diagnosing described above to determine if the disease has or has not progressed in the subject.

The method of monitoring may include obtaining a first biological sample from the subject and a second biological sample from the subject. The first biological sample may be obtained from the subject at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 1 year, 2 years, 3 years, 4 years, or 5 years before the second biological sample is obtained from the subject.

The method of monitoring may also include measuring a first level of laminin gamma 2 monomer in the first biological sample and a second level of laminin gamma 2 monomer in the second biological sample. The method of monitoring may further include comparing the first and second levels of laminin gamma 2 monomer and determining (i) the disease has progressed in the subject when the second level of laminin gamma 2 monomer is greater than the first level of laminin gamma 2 monomer, or (ii) the disease has not progressed in the subject when the second level of laminin gamma 2 monomer is equivalent to or less than the first level of laminin gamma 2 monomer.

The method of monitoring may further include measuring a first level of at least one additional biomarker in the first biological sample and a second level of the at least one additional biomarker in the second biological sample and comparing the first and second levels of the at least one additional biomarker. The method of monitoring may also determine that the disease has progressed in the subject when the second level of laminin gamma 2 monomer and the at least one additional biomarker is greater than the first level of laminin gamma 2 monomer and the at least one additional biomarker, respectively, or the disease has not progressed in the subject when the second level of laminin gamma 2 monomer and the at least one additional biomarker is equivalent to or less than the first level of laminin gamma 2 monomer and the at least one additional biomarker, respectively.

5. Kit

Also provided herein is a kit for use in performing the above-described methods. The kit may include instructions for detecting laminin gamma 2 monomer and/or at least one additional biomarker. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The kit may provide (1) reagents capable of specifically binding to each of laminin gamma 2 monomer and the at least one additional biomarker (i.e., PIVKA-II, AFP, CEA, and/or CA19-9) to quantify the levels of laminin gamma 2 monomer and/or the at least one additional biomarker in a biological sample isolated from a subject and (2) a reference standard indicating reference levels of each of laminin gamma 2 monomer and/or the at least one additional biomarker (i.e., PIVKA-II, AFP, CEA, and/or CA19-9), wherein at least one reagent comprises at least one antibody capable of specifically binding the appropriate biomarker.

In some embodiments, the kit may comprise a reagent that is capable of specifically binding to laminin gamma 2 monomer, a reagent that is capable of specifically binding to PIVKA-II, a reagent that is capable of specifically binding to AFP, a reagent that is capable of specifically binding to CEA, and/or a reagent that is capable of specifically binding to CA19-9 to quantify the concentration of each of laminin gamma 2 monomer, PIVKA-II, AFP, CEA, and/or CA19-9 in the biological sample and a reference standard indicating the reference level of each of laminin gamma 2 monomer, PIVKA-II, AFP, CEA, and/or CA19-9.

The kit may also comprise one or more containers, such as vials or bottles, with each container containing a separate reagent.

For example, the kit can comprise instructions for assaying the test sample for laminin gamma 2 monomer and/or the at least one additional biomarker by immunoassay, e.g., chemiluminescent microparticle immunoassay. The instructions can be in paper form or computer-readable form, such as a disk, CD, DVD, or the like. The antibody can be a laminin gamma 2 monomer and/or an at least one additional biomarker capture antibody and/or a laminin gamma 2 monomer and/or an at least one additional biomarker detection antibody (meaning an antibody labeled with a detectable label). For example, the kit can contain at least one capture antibody that specifically binds laminin gamma 2 monomer, at least one capture antibody that specifically binds PIVKA-II, at least one capture antibody that specifically binds AFP, at least one capture antibody that specifically binds CEA, and/or at least one capture antibody that specifically binds CA19-9. The kit can also contain a conjugate antibody (such as an antibody labeled with a detectable label) for each capture antibody (namely, a conjugate antibody for each of the capture antibodies that specifically bind to laminin gamma 2 monomer, PIVKA-II, AFP, CEA, and/or CA19-9, respectively). Alternatively or additionally, the kit can comprise a calibrator or control, e.g., purified, and optionally lyophilized, (e.g., laminin gamma 2 monomer, PIVKA-II, AFP, CEA, and/or CA19-9), and/or at least one container (e.g., tube, microtiter plates or strips, which can be already coated with an anti-laminin gamma 2 monomer, PIVKA-II, AFP, CEA, and/or CA19-9 monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying laminin gamma 2 monomer and/or the at least one additional biomarker (e.g., PIVKA-II, AFP, CEA, and/or CA19-9).

As alluded to above, any antibodies, which are provided in the kit, such as recombinant antibodies specific for laminin gamma 2 monomer and/or the at least one additional biomarker (e.g., PIVKA-II, AFP, CEA, and/or CA19-9) can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a blood sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution.

If desired, the kit can contain a solid phase, such as a magnetic particle, bead, test tube, microtiter plate, cuvette, membrane, scaffolding molecule, film, filter paper, a quartz crystal, disc or chip. The kit may also include a detectable label that can be or is conjugated to an antibody, such as an antibody functioning as a detection antibody. The detectable label can for example be a direct label, which may be an enzyme, oligonucleotide, nanoparticle, chemiluminophore, fluorophore, fluorescence quencher, chemiluminescence quencher, or biotin. Kits may optionally include any additional reagents needed for detecting the label.

If desired, the kit can further comprise one or more components, alone or in further combination with instructions, for assaying the test sample for another analyte, which can be a biomarker, such as a biomarker of cancer. Examples of analytes include, but are not limited to laminin gamma 2 monomer, PIVKA-II, AFP, CEA, and/or CA19-9, and fragments of laminin gamma 2 monomer, PIVKA-II, AFP, CEA, and/or CA19-9 as well other analytes and biomarkers discussed herein, or otherwise known in the art. In some embodiments one or more components for assaying a test sample for laminin gamma 2 monomer and/or at least one additional biomarker (e.g., PIVKA-II, AFP, CEA, and/or CA19-9) enable the determination of the presence, amount or concentration of the laminin gamma 2 monomer and/or the at least one additional biomarker (e.g., PIVKA-II, AFP, CEA, and/or CA19-9). A sample, such as a serum sample, can also be assayed for laminin gamma 2 monomer and/or the at least one additional biomarker (e.g., PIVKA-II, AFP, CEA, and/or CA19-9) using TOF-MS and an internal standard.

The kit (or components thereof), as well as the above-described methods, which detect the concentration of laminin gamma 2 monomer and/or the at least one additional biomarker (e.g., PIVKA-II, AFP, CEA, and/or CA19-9) in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing laminin gamma 2 monomer and/or the at least one additional biomarker is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of laminin gamma 2 monomer and/or at least one additional biomarker (e.g., PIVKA-II, AFP, CEA, and/or CA19-9) in the sample by means of an embedded algorithm and factory-determined calibration curve.

The present invention has multiple aspects, illustrated by the following non-limiting examples.

6. Examples

Example 1

Methods and Materials

Antibodies and Antigens.

Recombinant monomeric Ln-γ2 protein was purified from the culture medium of Madin-Darby canine kidney cell transfectants. Recombinant heterotrimeric Ln-332 was purchased from Oriental Yeast Co., Ltd. (Tokyo, Japan). For CLIA and western blotting, a monoclonal anti-Ln-γ2 antibody (2H2) and a polyclonal anti-Ln-γ2 domain III antibody were prepared, as described in Example 2. A mouse monoclonal anti-Ln-α3 antibody was purchased from Oriental Yeast Co., Ltd.

Analysis of Tumor Markers for HCC.

The serum AFP level was measured by using the ARCHITECT system and the PIVKA-II level was measured by using LUMIPULSE (Fujirebio, Inc., Tokyo, Japan) in SRL Tokyo Laboratories, Inc. (Tokyo, Japan).

Statistical Analysis.

The serum Ln-γ2 levels were reported as mean±standard deviation (SD) and median: range. The serum AFP and PIVKA-II levels were reported as median:range. Log transformation was used on the AFP and PIVKA-II values to account for the large range of values for both markers among the patients with HCC. The Mann-Whitney test was used for continuous data. p-values less than 0.05 were considered significant. Graph Pad Prism 6 Software (San Diego, Calif., USA) and Analyse-it Software (FIGS. 2-6 and 9-14) were used to generate the scatter plots, receiver operating characteristic (ROC) curves, and the calculation of the area under the ROC (AUC) curves. The optimal cutoff point included the point on the ROC curve closest to the (0, 1).

Example 2

Laminin Gamma 2 Monomer Immunoassay

An immunoassay was established that specifically detected laminin gamma 2 monomer.

Fully Automated Chemiluminescent Immunoassay (CLIA).

Human Ln-γ2 protein concentration was measured by a two-step sandwich assay using paramagnetic microparticles coated with 2H2 antibody (Nakagawa M et al., manuscript in preparation) and rabbit polyclonal antibody labeled with acridinium. The assay method was adjusted for application to a fully automated detection machine (ARCHITECT of Abbott Laboratories, Chicago, Ill., USA).

Generation of Polyclonal Antibody Directed Against Laminin Gamma 2 Monomer.

A polyclonal antibody directed against laminin gamma 2 monomer was generated by immunizing a rabbit with purified domain III (amino acids 383-608) of human laminin gamma 2 monomer. This recombinant domain III was expressed in and purified from *E. coli*. Specifically, domain III was expressed as a GST fusion protein using Gateway technology (Invitrogen). The rabbit sera were purified using a protein A column. Further purification of the polyclonal antibody was performed with an anti-His-tag monoclonal antibody magnetic agarose (MBL) conjugated with domain III by dimethyl pimelimidate dihydrochloride (DMP). The purified polyclonal antibody was also concentrated.

2H2 Monoclonal Antibody.

2H2 mAb was a mouse monoclonal antibody described in N. Koshikawa et al., Cancer Research (2008) 68(2):530-536. The 2H2 mAb was purified from the supernatant of the cultured hybridoma by a Protein G column.

Generation of Recombinant Laminin Gamma 2 Monomer.

The gene encoding full-length laminin gamma 2 monomer was introduced into MDCK cells to generate transfected MDCK cells expressing laminin gamma 2 monomer. MDCK cells expressing high levels of laminin gamma 2 monomer were selected by limiting dilution and cultured in serum-free DMEM (Invitrogen). Laminin gamma 2 monomer was purified using a 2H2 monoclonal antibody (2H2 mAb) column and concentrated by ammonium sulfate precipitation.

Immunoassay. The 2H2 mAb was immobilized on paramagnetic microparticles. Specifically, the microparticles were washed with MES buffer (pH 5.5) and N-(3-dimethylaminopropyl)-N'-ethyl-carbodiimidehydrochloride (Sigma-Aldrich) and N-hydroxysuccinimide (Sigma-Aldrich) were added to the washed microparticles. After a 30 minute incubation at room temperature, the microparticles were washed and 2H2 mAb diluted in MES buffer was added to the washed microparticles. After a 2 hour incubation at room temperature, the microparticles were washed with TBS, 1% Tween and then stored.

The microparticle dilution buffer was TBS buffer containing 20 mM EDTA, 1% BSA, 0.2% skim milk, 0.1% Tween-20, 0.2 mg/mL HBR, 0.2 mg/mL mouse IgG, 0.1% ProClin300, and 100 ppm Foamaway, pH 7.4. The microparticles were diluted in the microparticle dilution buffer at a final solid concentration of 0.05%.

The above-described rabbit polyclonal antibody directed against domain III of human laminin gamma 2 monomer was utilized as a detection antibody. Specifically, this polyclonal antibody was conjugated to acridinium in PBS buffer containing 0.5% CHAPS. Excess acridinium was removed by Zeba Micro Desalt Spin Column (Thermo). The resulting acridinium-labeled antibody was dissolved in MES buffer containing 0.15 M NaCl, 1.09% TritonX405, 2.0 mg/mL bovine gamma globulin, 5% BSA, 2% Tween-20, 0.1% ProClin300, and 100 ppm Foamaway, pH 6.3.

The immunoassay dilution solution was TBS buffer containing 1% BSA, 16.1% sucrose, 0.075% sodium azide, 0.1% ProClin950, and 100 ppm Foamaway, pH 8.0. The sample diluent was PBS buffer with 1% BSA and 0.1% Tween-20. The calibrator for the immunoassay was recombinant laminin gamma 2 monomer diluted in the sample diluent. Specifically, the calibrator for laminin gamma 2 monomer ranged over 0 ng/mL to 20 ng/mL. The specific amounts were 0.00, 0.01, 0.02, 0.05, 0.10, 1.00, 10.00, and 20.00 ng/mL.

The immunoassay was performed on an immunoassay instrument, namely the i2000 ARCHITECT analyzer. A calibration curve for laminin gamma 2 monomer was generated using the calibrator. Exemplary calibration curves are shown in FIG. 1.

Example 3

Detection of Laminin Gamma 2 Monomer in Specimens

The immunoassay described above in Example 2 was used to detect serum concentrations of laminin gamma 2 monomer in various specimens. Serum samples were collected from the specimens and diluted in the above-described sample diluent.

Specimens.

The specimens were hepatocellular carcinoma (HCC) specimens, pancreatic cancer specimens, colorectal cancer (CRC) specimens, stomach cancer specimens, liver cirrhosis (LC) specimens, hepatitis specimens, pancreatitis/cholangitis specimens, multi-cancer/metastasis specimens, liver failure specimens, benign specimens, healthy donor specimens, and other cancer specimens. Specimens were collected at St. Marianna University School of Medicine. For normal controls, healthy donor specimens were collected from healthy volunteers with no history of liver disease, alcohol consumption of less than 40 g/week, and no risk factors for viral hepatitis. To establish the cutoff value for Ln-γ2, control sera from 52 healthy Japanese volunteers were analyzed. Demographic and clinical characteristics of healthy volunteers and patients with chronic liver disease or HCC are shown in Table 1. The mean and median serum Ln-γ2 levels of healthy volunteers were 44.3±17.6 pg/mL (mean±SD) and 41.1 pg/mL (range: 10.9-79.0 pg/mL), respectively.

TABLE 1

Demographic information and etiology of liver diseases.
All data are expressed as median: range.

|  | Healthy control (n = 52) | Chronic liver disease (n = 24) | HCC (n = 57) |
|---|---|---|---|
| Gender | | | |
| M:F | 32/20 | 11/13 | 38/19 |
| Age (y) | 33 (25-58) | 59 (35-74) | 71 (49-80) |

TABLE 1-continued

Demographic information and etiology of liver diseases.
All data are expressed as median: range.

|  | Healthy control (n = 52) | Chronic liver disease (n = 24) | HCC (n = 57) |
| --- | --- | --- | --- |
| Etiology (%) |  |  |  |
| HCV |  | 20 (83%) | 30 (52%) |
| HBV |  | 3 (13%) | 8 (14%) |
| HBV + HCV |  |  | 1 (2%) |
| Alcohol |  |  | 12 (21%) |
| NBNCNAL |  | 1 (4%) | 5 (9%) |
| Autoimmune |  |  | 1 (2%) |
|  |  |  | median (range) |

Results.

Figure 2A:
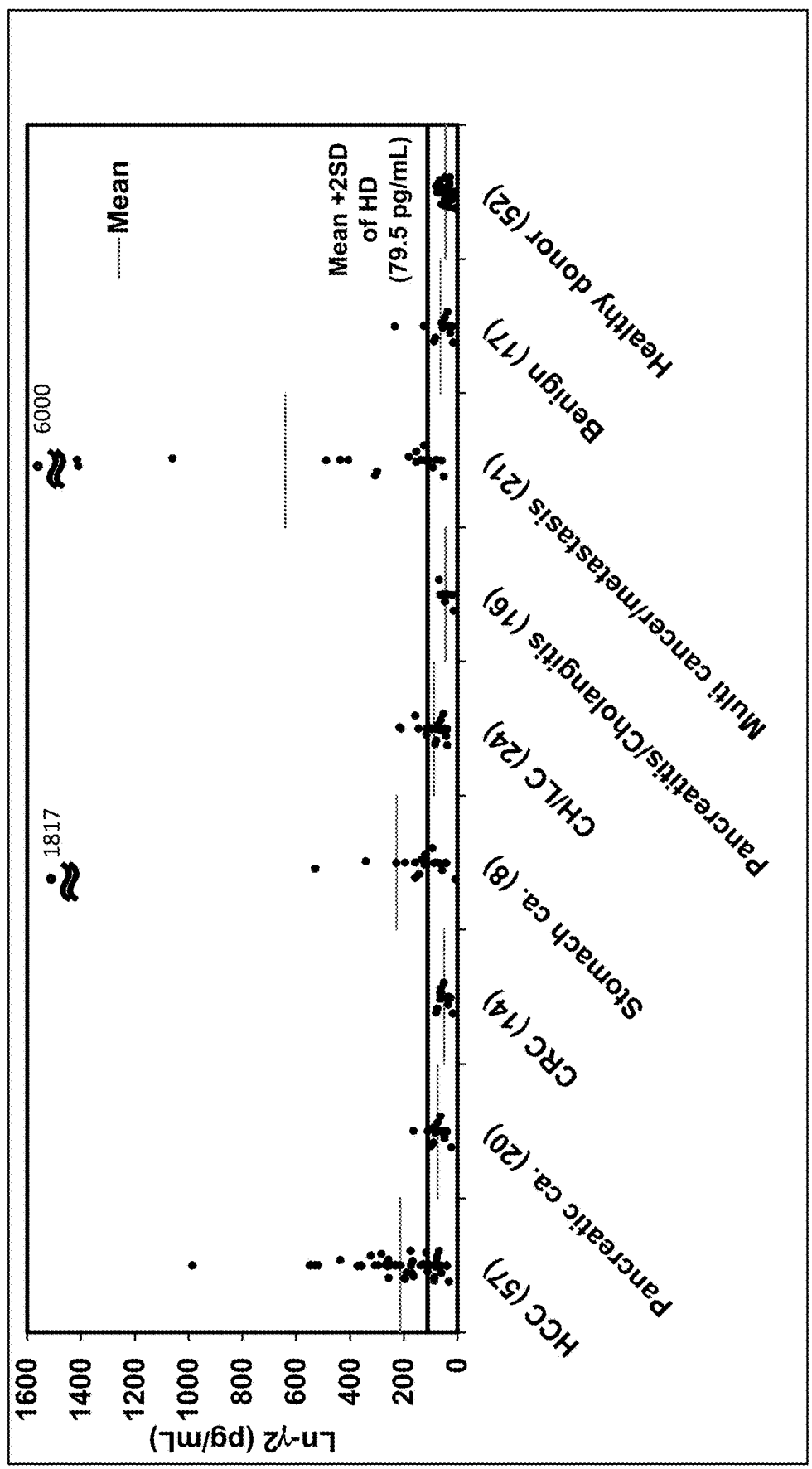
FIG. 2A shows a graph plotting subject group against serum concentration (pg/mL) of laminin gamma 2 monomer. For each subject group, the number in parenthesis represented the number of subjects in the group and the solid line represented the mean serum concentration (pg/mL) of laminin gamma 2 monomer for the group. The solid line extending the length of the x-axis represented the mean plus 2 standard deviations (Mean+2SD) for the healthy donor subject group, which was 81.3 pg/mL.
Figure 2B:
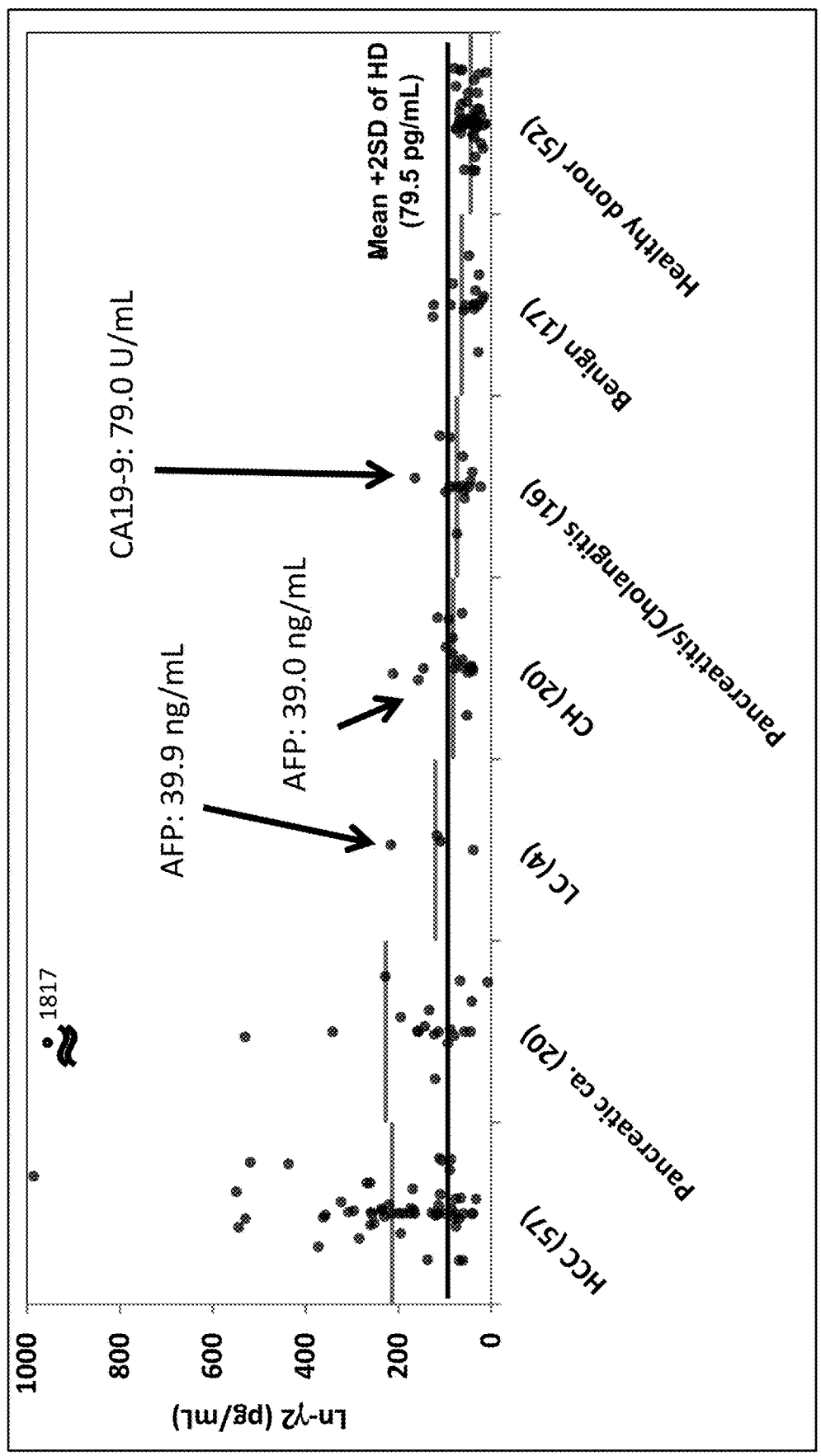
FIG. 2B shows a graph plotting subject group against serum concentration (pg/mL) of laminin gamma 2 monomer. For each subject group, the number in parenthesis represented the number of subjects in the group and the solid line represented the mean serum concentration (pg/mL) of laminin gamma 2 monomer for the group. The solid line extending the length of the x-axis represented the mean plus 2 standard deviations (Mean+2SD) for the healthy donor subject group, which was 79.5 pg/mL. Arrows identified the subjects for the specified AFP and CA19-9 concentrations.
Figure 2C:
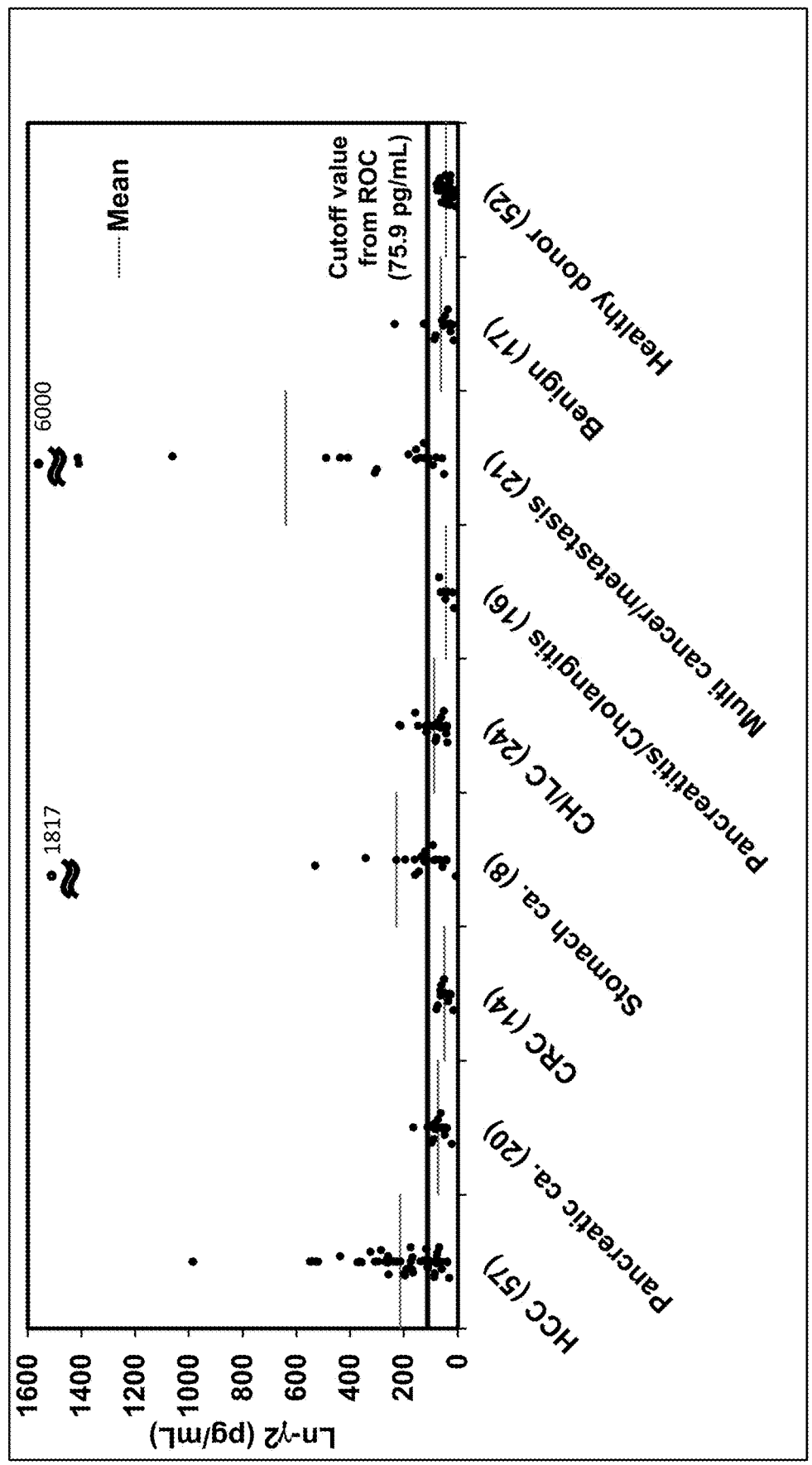
FIG. 2C shows a graph plotting subject group against serum concentration (pg/mL) of laminin gamma 2 monomer. For each subject group, the number in parenthesis represented the number of subjects in the group and the solid line represented the mean serum concentration (pg/mL) of laminin gamma 2 monomer for the group. The solid line extending the length of the x-axis represented the cutoff value derived from ROC analysis, which was 75.9 pg/mL.
Figure 2D:
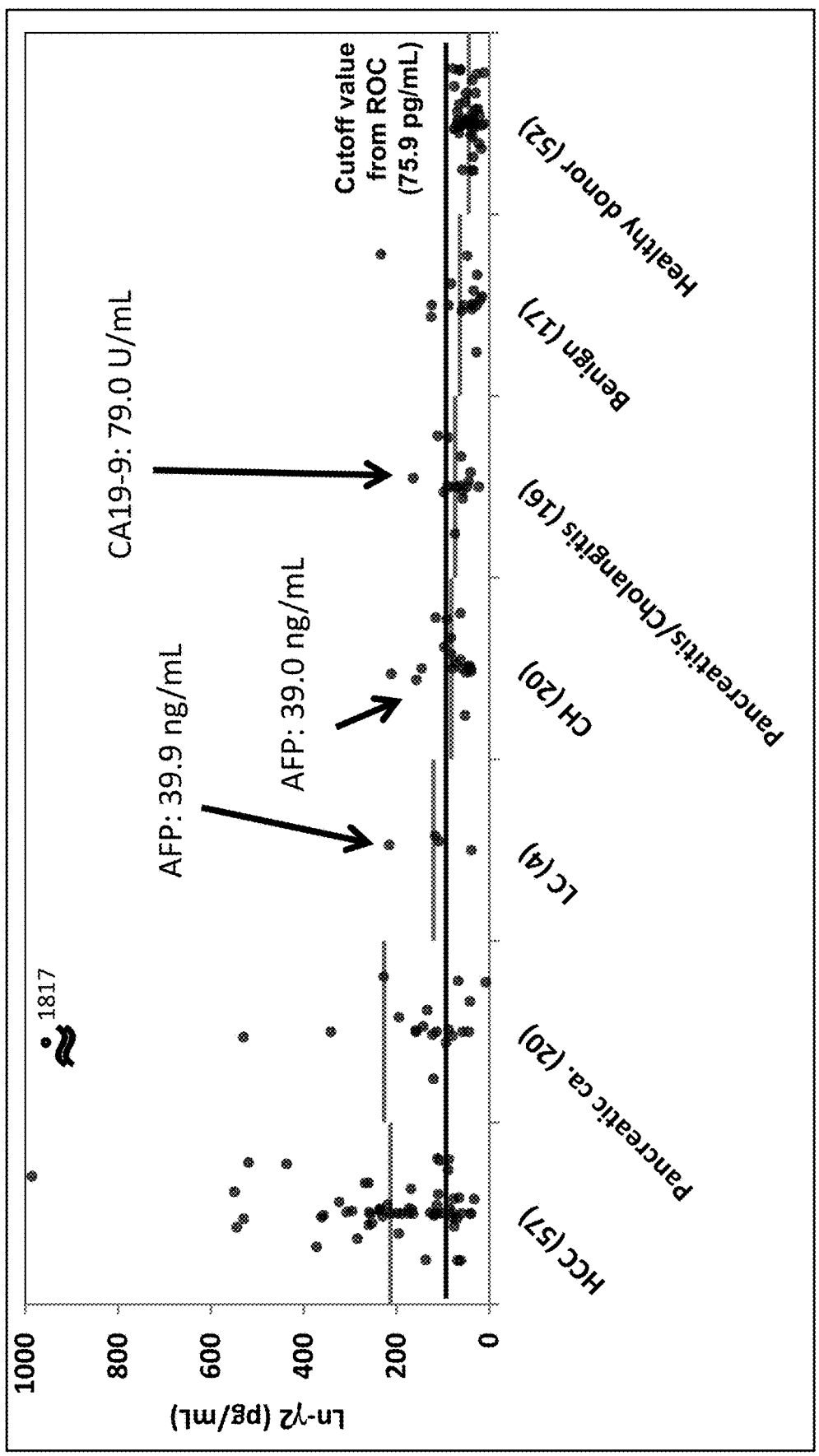
FIG. 2D shows a graph plotting subject group against serum concentration (pg/mL) of laminin gamma 2 monomer. For each subject group, the number in parenthesis represented the number of subjects in the group and the solid line represented the mean serum concentration (pg/mL) of laminin gamma 2 monomer for the group. The solid line extending the length of the x-axis represented the cut off value derived from ROC analysis, which was 75.9 pg/mL. Arrows identified the subjects for the specified AFP and CA19-9 concentrations.

FIGS. 2A and 2B show dot plots of the serum concentration (pg/mL) of laminin gamma 2 monomer for the indicated specimens. Each specimen was depicted by a solid circle. The mean serum concentration for each group of specimens was depicted by a solid line. The mean plus 2 standard deviations (Mean+2SD) of healthy donors (HD) was also shown with a solid line extending the length of the x-axis and was 79.5 pg/mL. FIGS. 2C and 2D show dot plots of the serum concentration (pg/mL) of laminin gamma 2 monomer for the indicated specimens. Each specimen was depicted by a solid circle (FIGS. 2C and 2D). The mean serum concentration for each group of specimens was depicted by a solid line. The cutoff value derived from ROC analysis of HCC compared against healthy donors (HD) was also shown with a solid line extending the length of the x-axis and was 75.9 pg/mL. The serum concentration of laminin gamma 2 monomer was higher in HCC and pancreatic cancer specimens as compared to the healthy donor specimens and specimens with other digestive carcinomas (i.e., colorectal cancer and stomach cancer).

Additionally, the serum concentration of laminin gamma 2 monomer was higher in HCC and pancreatic cancer specimens as compared to liver cirrhosis specimens, CH specimens, and pancreatitis/cholangitis specimens. However, one liver cirrhosis specimen with a higher serum concentration of laminin gamma 2 monomer had a level of alpha fetal protein (AFP) of 39.9 ng/mL (FIGS. 2B and 2D). One CH specimen with a higher serum concentration of laminin gamma 2 monomer had a level of alpha fetal protein (AFP) of 39.0 ng/mL (FIGS. 2B and 2D). One pancreatitis/cholangitis specimen with a higher serum concentration of laminin gamma 2 monomer had a level of carbohydrate antigen 19-9 (CA19-9) of 79.0 U/mL. Accordingly, specimens other than HCC and pancreatic cancer that had higher serum concentrations of laminin gamma 2 monomer had abnormal levels of other cancer markers such as AFP and CA19-9.

Example 4

Serum Concentration of Laminin Gamma 2 Monomer in Stages I-IV of HCC

As described in Example 3, the serum concentration of laminin gamma 2 monomer was higher in HCC specimens. The HCC specimens were further examined with regards to the serum concentration of laminin gamma 2 monomer in different stages of HCC. Specifically, the immunoassay described above in Example 2 was used to detect serum concentrations of laminin gamma 2 monomer from HCC stage I, HCC stage II, HCC stage III, and HCC stage IV specimens as well as from liver cirrhosis (LC), hepatitis (CH), and healthy donor specimens. Serum samples were collected from the specimens and diluted in the above-described sample diluent.

Results.

Figure 3A:
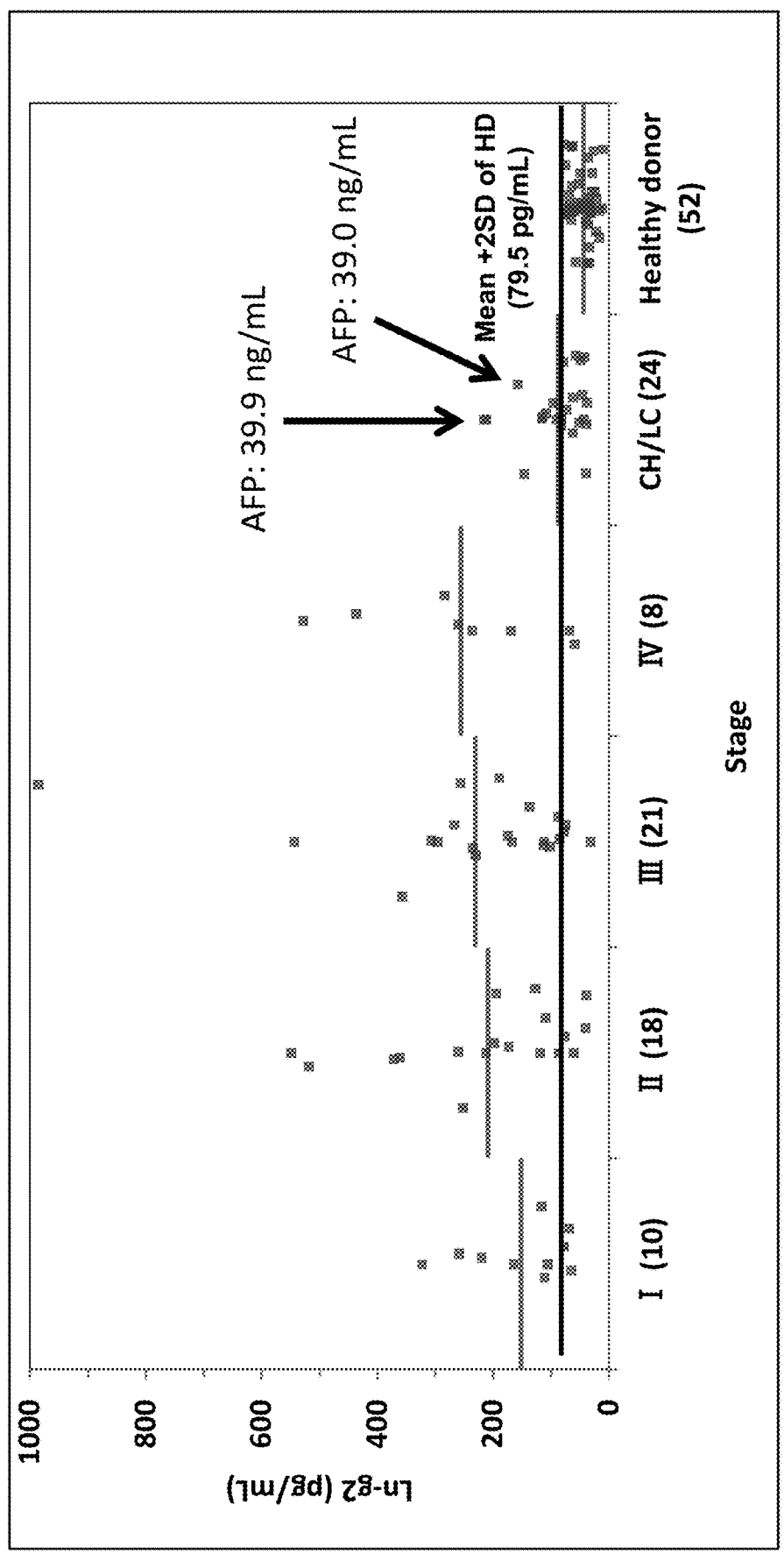
FIG. 3A shows a graph plotting subject group against serum concentration (pg/mL) of laminin gamma 2 monomer. The designations "I," "II," "III," and "IV" represented the subject groups having stage I HCC, stage II HCC, stage III HCC, and stage IV HCC, respectively. "LC" represented liver cirrhosis and "CH" represented hepatitis. For each subject group, the number in parenthesis represented the number of subjects in the group and the solid line represented the mean serum concentration (pg/mL) of laminin gamma 2 monomer for the group. The solid line extending the length of the x-axis represented the mean plus 2 standard deviations (Mean+2SD) for the healthy donor subject group, which was 79.5 pg/mL. Arrows identified the subjects for the specified AFP concentrations.
Figure 3B:
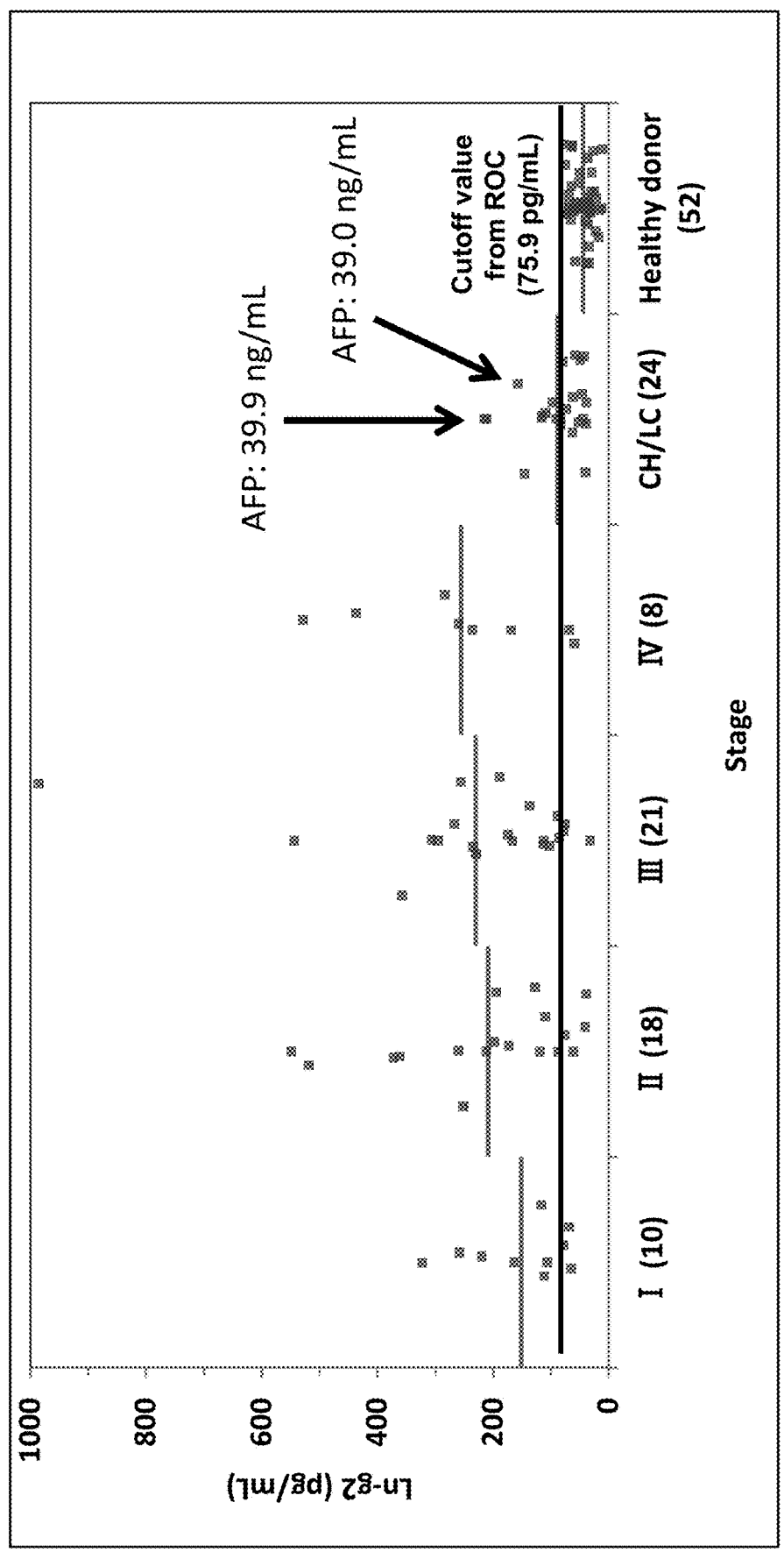
FIG. 3B shows a graph plotting subject group against serum concentration (pg/mL) of laminin gamma 2 monomer. The designations "I," "II," "III," and "IV" represented the subject groups having stage I HCC, stage II HCC, stage III HCC, and stage IV HCC, respectively. "LC" represented liver cirrhosis and "CH" represented hepatitis. For each subject group, the number in parenthesis represented the number of subjects in the group and the solid line represented the mean serum concentration (pg/mL) of laminin gamma 2 monomer for the group. The solid line extending the length of the x-axis represented the cutoff value derived from ROC analysis, which was 75.9 pg/mL. Arrows identified the subjects for the specified AFP concentrations.

The results of these studies are shown in FIGS. 3A-3B, which show the serum concentration (pg/mL) of laminin gamma 2 monomer for each group of indicated specimens. Each specimen was depicted with a solid circle. The mean serum concentration of laminin gamma 2 monomer for each specimen group was indicated with a solid line. The solid line extending the length of the x-axis indicated the mean plus 2 standard deviations (Mean+2SD) for the healthy donor specimens, which was 79.5 pg/mL in FIG. 3A. The solid line extending the length of the x-axis indicated the cutoff value derived from ROC analysis of HCC compared against healthy donors (HD) was also shown with a solid line extending the length of the x-axis and was 75.9 pg/mL in FIG. 3B.

As shown in FIGS. 3A-3B, elevated serum concentrations of laminin gamma 2 monomer were observed in HCC stage I, HCC stage II, HCC stage III, and HCC stage IV specimens as compared to LC, CH, and healthy donor specimens. LC and CH specimens with higher serum concentrations of laminin gamma 2 monomer had abnormal levels of cancer marker alpha fetal protein (AFP), namely 39.9 ng/mL and 39.0 ng/mL. Accordingly, these results indicated that laminin gamma 2 monomer was detected in serum from early stage HCC specimens and that laminin gamma 2 monomer levels in serum increased with HCC stage (i.e., increased in a stage-dependent manner for HCC).

Figure 12:
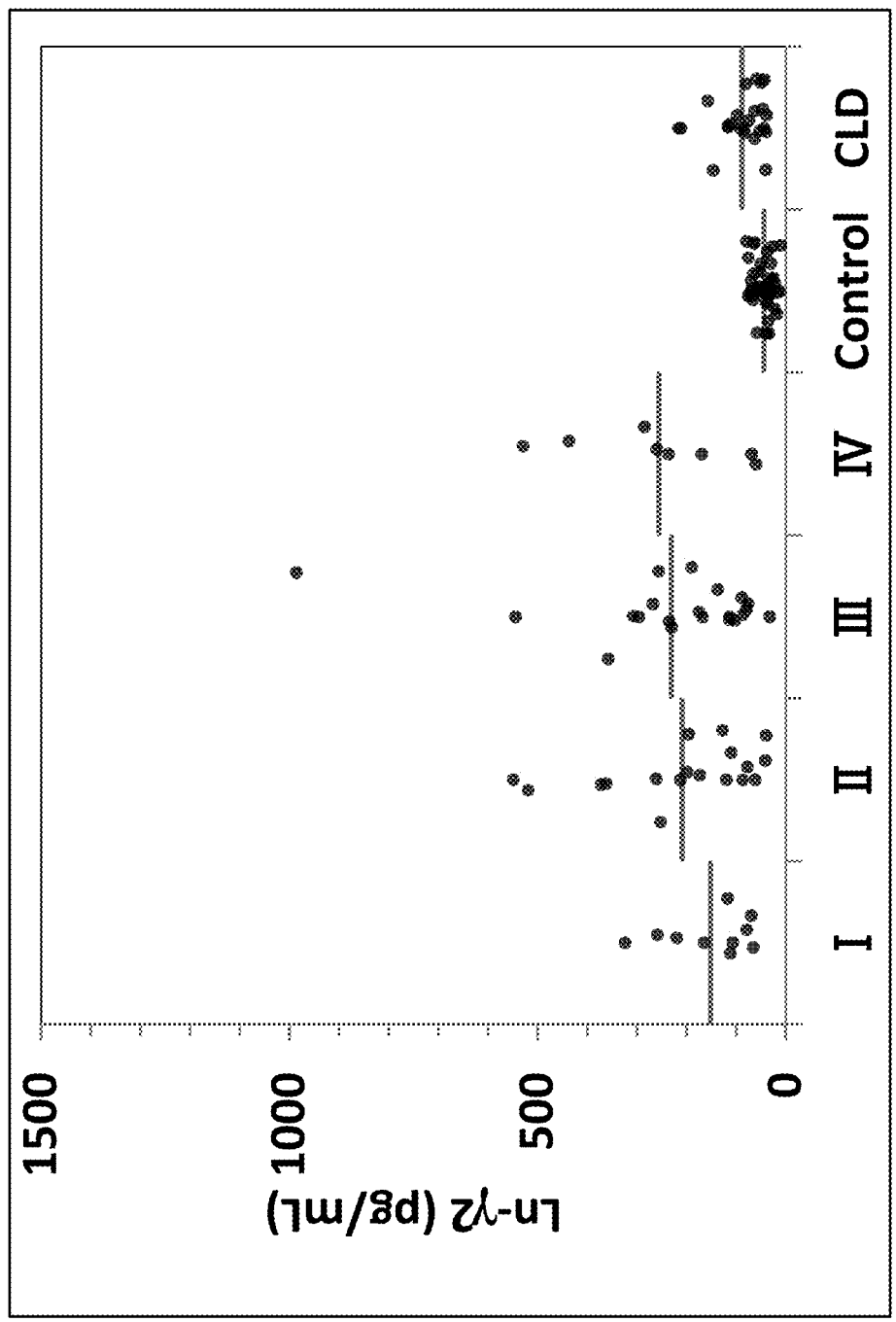
FIG. 12 shows Ln-γ2 values according to tumor staging based on the TNM classification. The horizontal lines represent median concentrations. Abbreviations: CLD, chronic liver disease.
Figure 13:
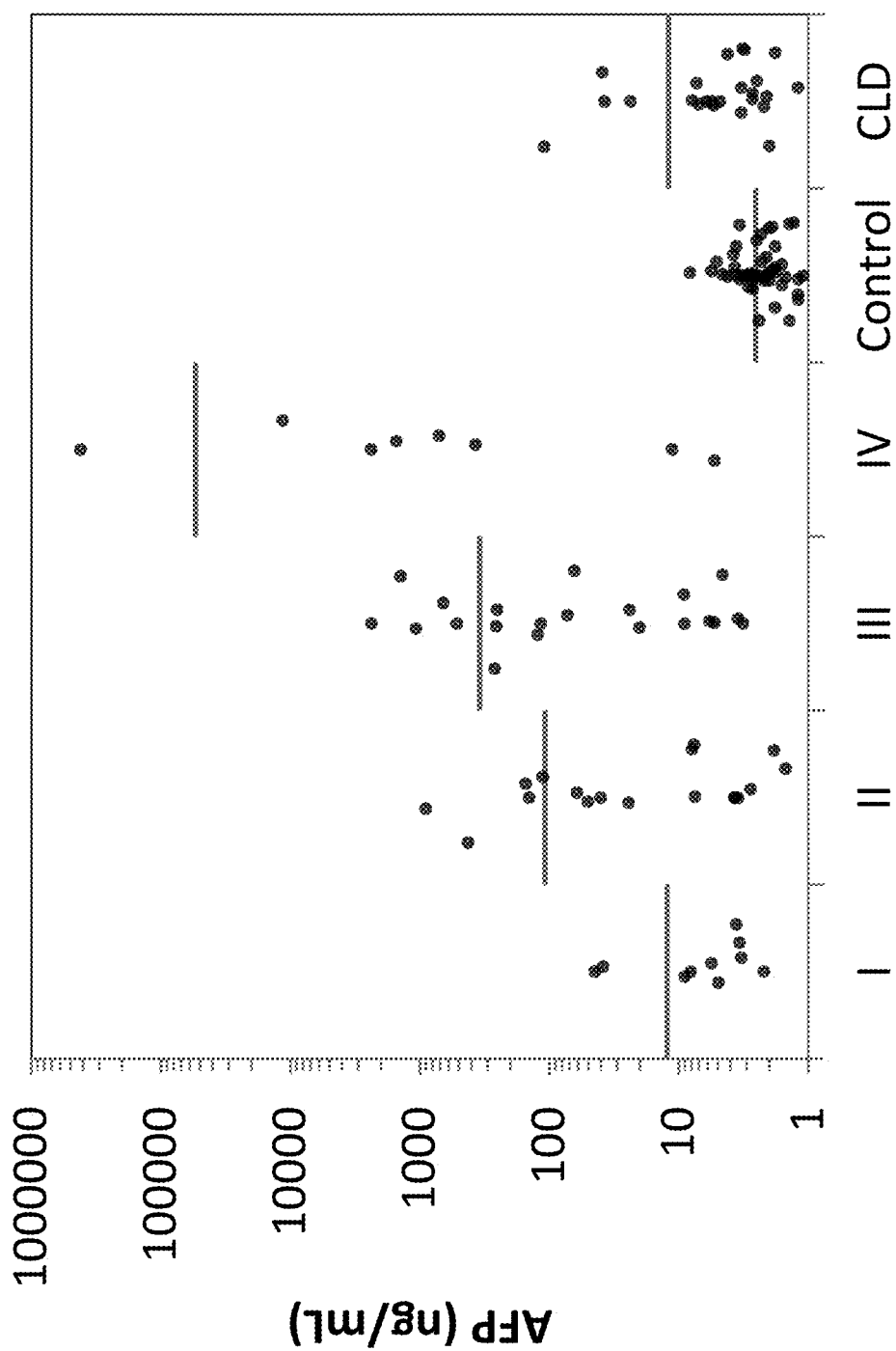
FIG. 13 shows AFP values according to tumor staging based on the TNM classification. The horizontal lines represent median concentrations. Abbreviations: CLD, chronic liver disease.
Figure 14:
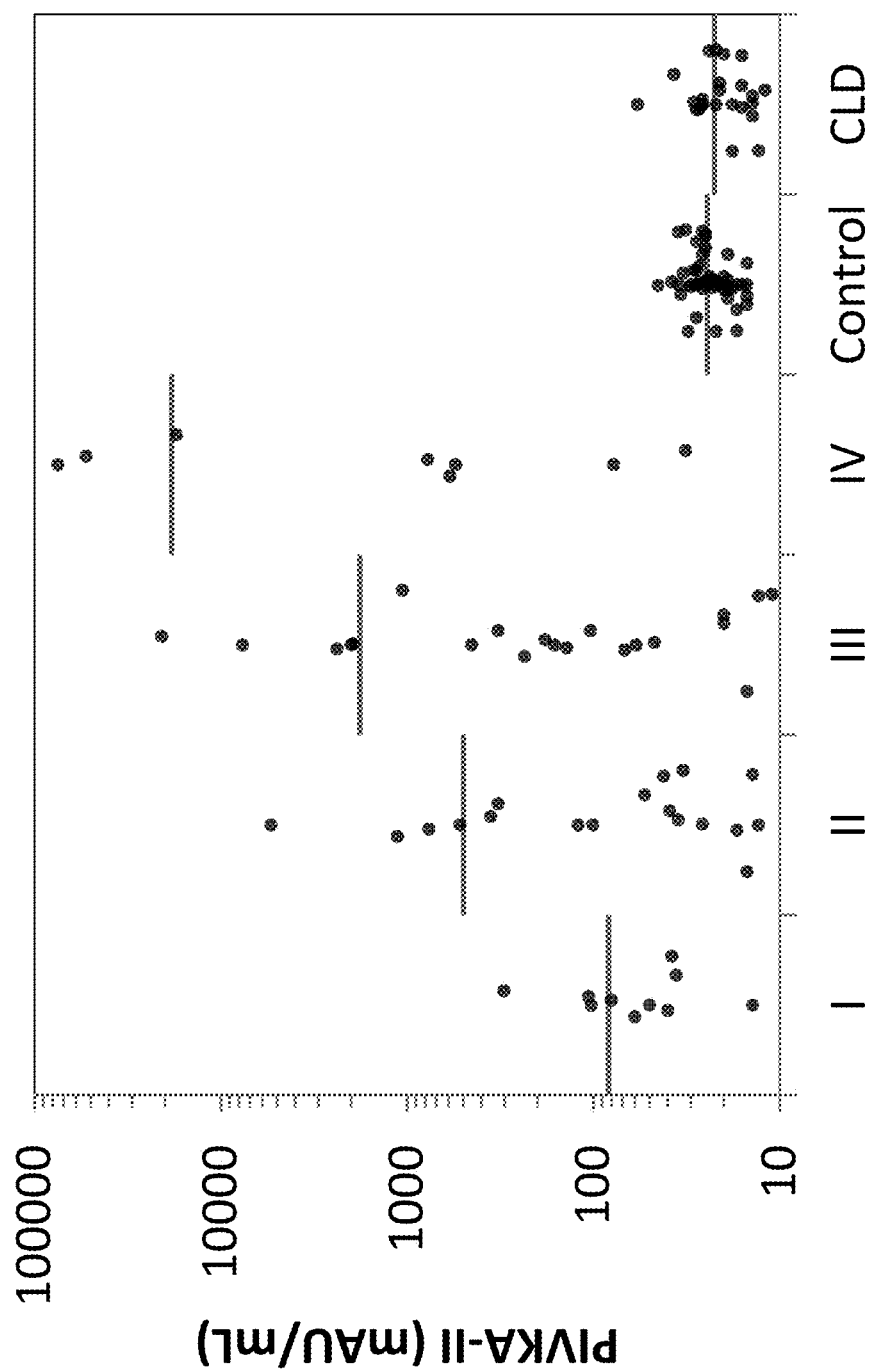
FIG. 14 shows PIVKA-II values according to tumor staging based on the TNM classification. The horizontal lines represent median concentrations. Abbreviations: CLD, chronic liver disease.

According to the TNM classification, 10 patients were diagnosed with stage I, 18 with stage II, 21 with stage III, and 8 with stage IV tumors. Ln-γ2 levels increased from stage I to stage IV with median levels (range) of 114.3 pg/mL (range: 65.3-323.6 pg/mL), 184.3 pg/mL (range: 39.5-549.1 pg/mL), 174.6 pg/mL (range: 32.4-985.8 pg/mL), and 248.1 pg/mL (range: 59.8-529.4 pg/mL), respectively (FIG. 12). The corresponding AFP values were 5.3 ng/mL (range: 2.2-44.6 ng/mL), 16.2 ng/mL (range: 1.5-899 ng/mL), 72.5 ng/mL (range: 3.2-2364 ng/mL), and 1116 ng/mL (range: 5.3-417198 ng/mL) ng/mL for stage I, II, III, and IV HCC, respectively (FIG. 13). The corresponding PIVKA-II values were 55.0 mAU/mL (range: 14.0-302 mAU/mL), 47.5 mAU/mL (range: 13.0-5380) mAU/mL, 162 mAU/mL (range: 11.0-20779), and 683 mAU/mL (range: 32.0-75000 mAU/mL) for stage I, II, III, and IV HCC, respectively (FIG. 14). Among patients with early stage HCC (T1 or T2), the positivity rates for Ln-γ2, AFP, and PIVKA-II were 17/28 (61%), 11/28 (39%), and 16/28 (57%), respectively.

Example 5

Specificity and Sensitivity of Laminin Gamma 2 Monomer as a Marker for HCC

The specificity and sensitivity of laminin gamma 2 monomer, alpha fetal protein (AFP), and protein induced vitamin K antagonist-II (PIVKA-II) as markers for HCC were examined. Specifically, the level of each marker was examined in 57 HCC specimens and 76 healthy donor, liver cirrhosis (LC), or hepatitis (CH) specimens, for a total of 133 specimens.

Figure 4A:
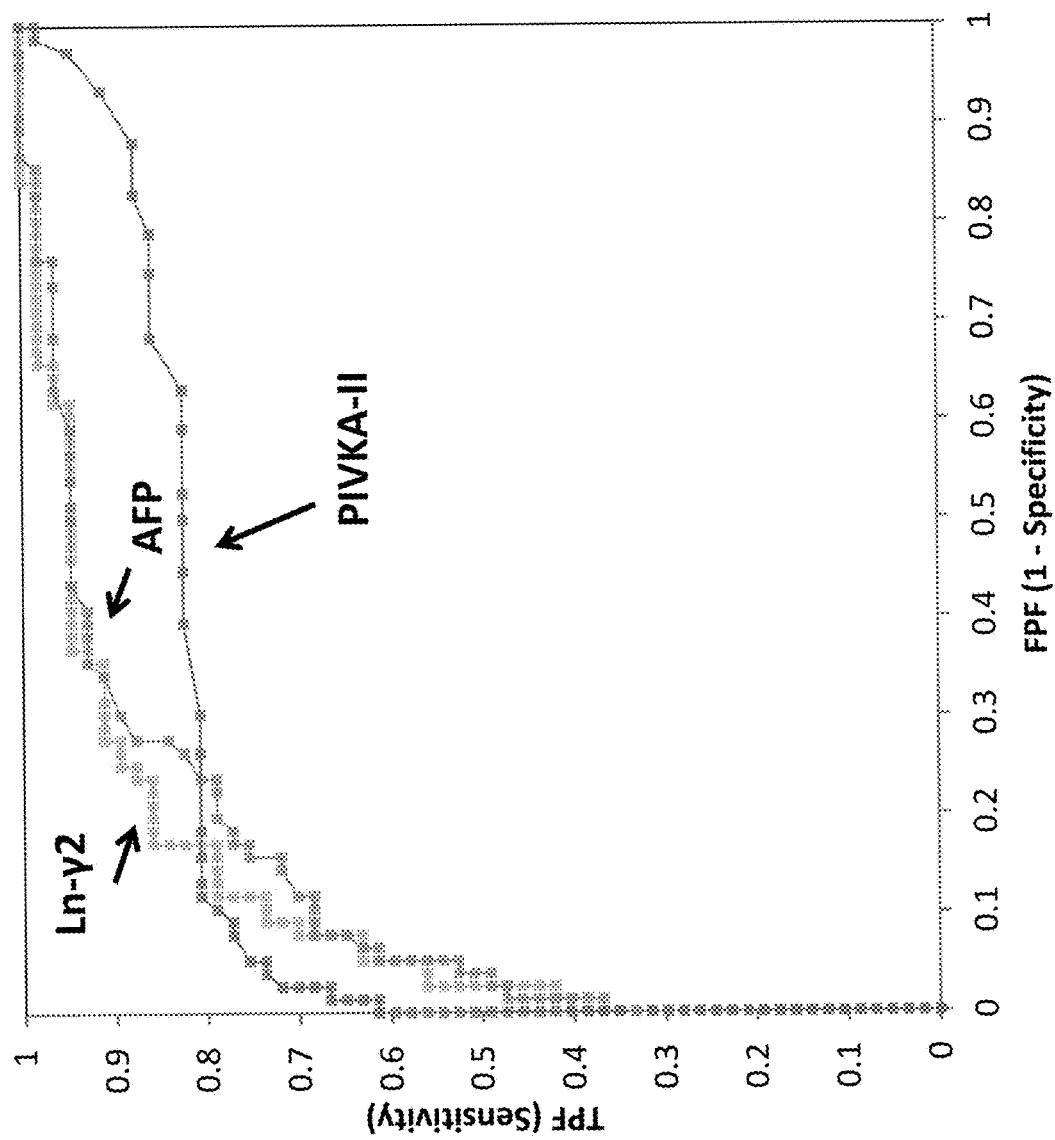
FIG. 4A shows a Receiver Operator Characteristic (ROC) graph for the markers laminin gamma 2 monomer (Ln-γ2), PIVKA-II, and AFP, in which subjects having HCC were compared against liver cirrhosis (LC), hepatitis (CH), and healthy donor subjects.

A receiver operator characteristic (ROC) graph was generated by plotting the observed true positive rate of laminin gamma 2 monomer, AFP, and PIVKA-II in the HCC specimens against the observed false positive rate of laminin gamma 2 monomer, AFP, and PIVKA-II in healthy donor, LC, and CH specimens. Accordingly, the ROC graph was a plot of sensitivity (true positive frequency (TPF)) against specificity (false positive frequency (FPF)). A value of 1.000 represented 100% sensitivity and 100% specificity. This ROC graph is shown in FIG. 4A and the area under the curve (AUC) for each of laminin gamma 2 monomer, AFP, and PIVKA-II is shown in Table 2.

TABLE 2

| Marker | AUC |
| --- | --- |
| Laminin gamma 2 monomer | 0.902 |
| AFP | 0.884 |
| PIVKA-II | 0.831 |

Figure 9:
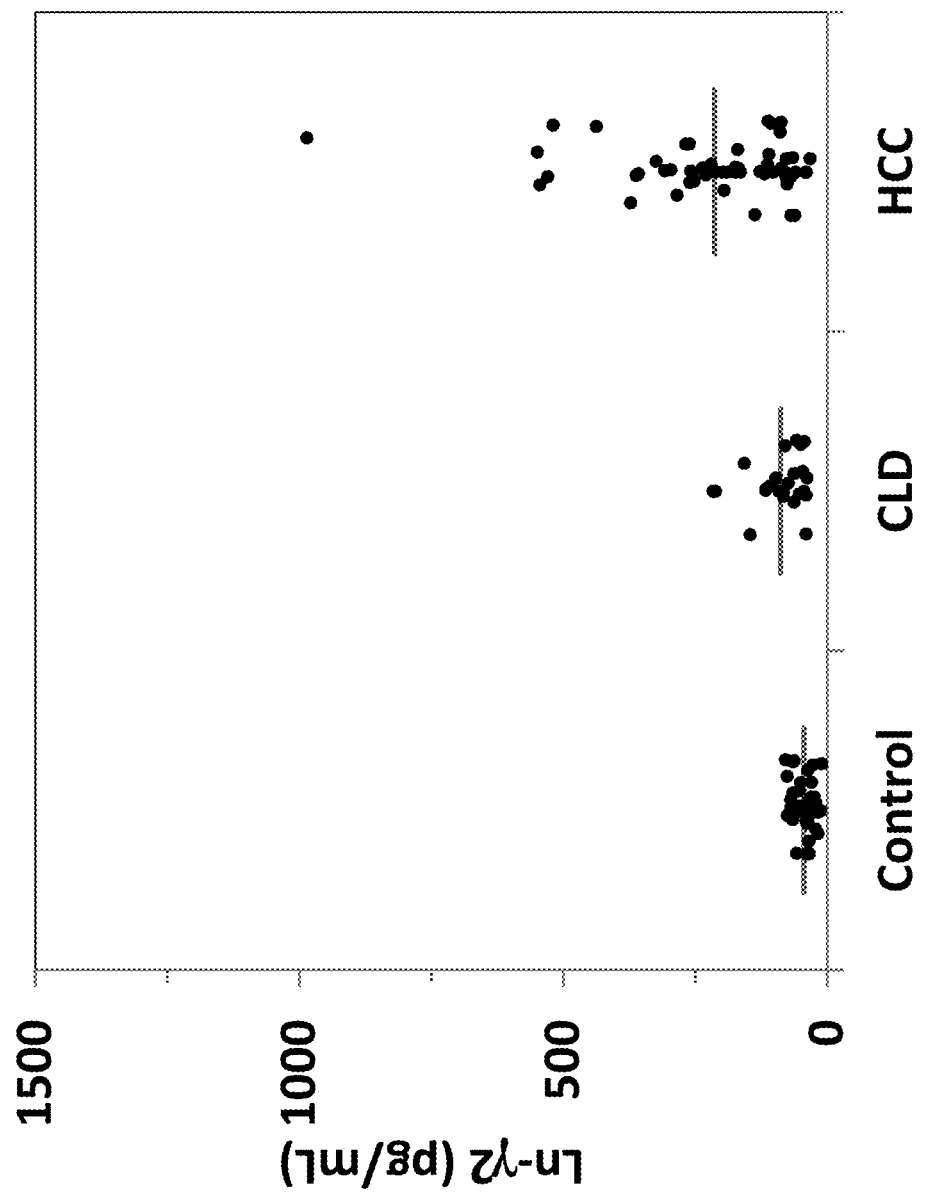
FIG. 9 shows a scatter plot of serum Ln-γ2 concentrations determined in serum samples from normal subjects (Control) (n=52), patients with chronic liver disease (CLD) (n=24), and patients with HCC (n=57). The horizontal lines represent median concentrations. Abbreviations: Ln-γ2, laminin γ2.

The specificity and sensitivity of laminin gamma 2 monomer, alpha fetal protein (AFP), and protein induced vitamin K antagonist-II (PIVKA-II) as markers for HCC were examined. Specifically, the level of each marker was examined in 57 HCC specimens and 52 healthy donor, for a total of 109 specimens. Serum Ln-γ2 levels were measured in 24 patients with chronic liver disease and 57 patients with HCC (FIG. 9). Infection with HCV was the most common etiologic factor between the two groups of subjects with liver disease. The median Ln-γ2 concentrations were 76.7 pg/mL, with a range between 38.7 and 215.9 pg/mL (patients with chronic liver disease) and 173.2 pg/mL, with a range between 32.4 and 986 pg/mL (patients with HCC). A significant increase in Ln-γ2 levels was observed in patients with HCC when compared to patients with chronic liver disease and healthy volunteers ($p<0.01$).

Figure 4B:
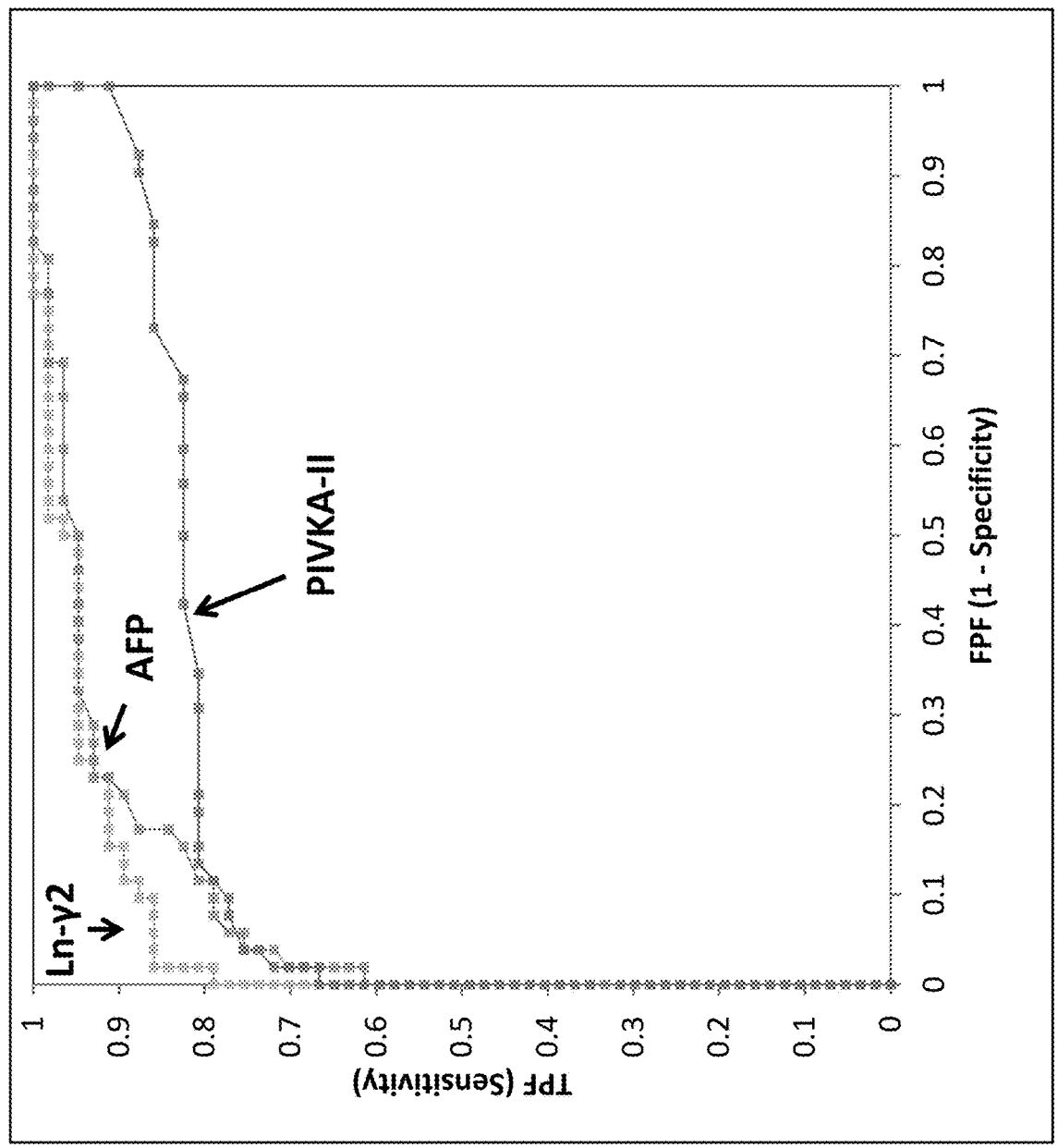
FIG. 4B shows a Receiver Operator Characteristic (ROC) graph for the markers laminin gamma 2 monomer (Ln-γ2), PIVKA-II, and AFP, in which subjects having HCC were compared against healthy donor subjects.

A receiver operator characteristic (ROC) graph was generated by plotting the observed true positive rate of laminin gamma 2 monomer, AFP, and PIVKA-II in the HCC specimens against the observed false positive rate of laminin gamma 2 monomer, AFP, and PIVKA-II in healthy donor specimens. Accordingly, the ROC graph was a plot of sensitivity (true positive frequency (TPF)) against specificity (false positive frequency (FPF)). A value of 1.000 represented 100% sensitivity and 100% specificity. This ROC graph is shown in FIG. 4B and the area under the curve (AUC) for each of laminin gamma 2 monomer, AFP, and PIVKA-II is shown in Table 3.

TABLE 3

| Marker | AUC |
| --- | --- |
| Laminin gamma 2 monomer | 0.952 |
| AFP | 0.929 |
| PIVKA-II | 0.825 |

When the cutoff value was set at 75.9 pg/mL, the sensitivity and specificity were 86% (95% confidence interval [CI], 74-94%) and 98% (95% CI, 90-99%), respectively. The discriminative ability of Ln-γ2 (ROC curve AUC=0.952; 95% CI, 91-99%) significantly surpassed that of PIVKA-II (ROC curve AUC=0.825; 95% CI, 73-92%, $p<0.05$) and it was as effective as AFP (ROC curve AUC=0.929; 95% CI, 88-98%) when comparing healthy volunteers and patients with HCC. When healthy volunteers were compared to patients with non-malignant chronic liver disease, this cutoff value yielded a discriminative ability for Ln-γ2 (ROC curve AUC=0.819; 95% CI, 72-92%) with a sensitivity and specificity of 50% (95% CI, 29-71%) and 96% (95% CI, 87-99%), respectively. With this cutoff value, Ln-γ2 positivity was found in 1 (2%), 12 (50%), and 50 (86%) subjects among healthy volunteers, patients with chronic liver disease, and patients with HCC, respectively. These results indicate that this cutoff value (>75.9 pg/mL) is useful to distinguish patients with chronic liver disease, with or without HCC, from healthy subjects.

The specificity and sensitivity of laminin gamma 2 monomer, alpha fetal protein (AFP), and protein induced vitamin K antagonist-II (PIVKA-II) as markers for HCC were examined. Specifically, the level of each marker was examined in 57 HCC specimens and 24 hepatitis (CH) specimens, for a total of 81 specimens.

Figure 4C:
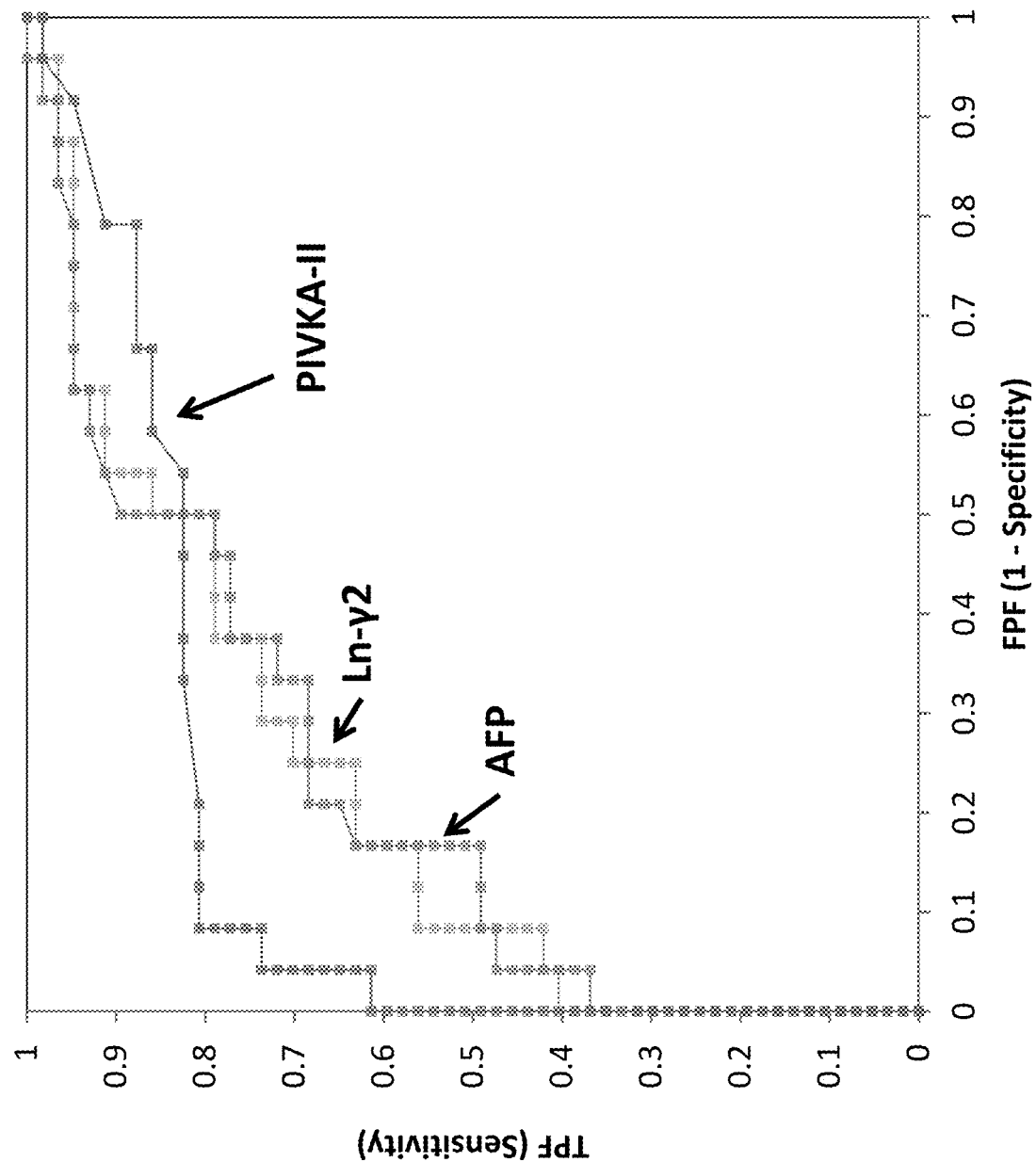
FIG. 4C shows a Receiver Operator Characteristic (ROC) graph for the markers laminin gamma 2 monomer (Ln-γ2), PIVKA-II, and AFP, in which subjects having HCC were compared against liver hepatitis (CH).

A receiver operator characteristic (ROC) graph was generated by plotting the observed true positive rate of laminin gamma 2 monomer, AFP, and PIVKA-II in the HCC specimens against the observed false positive rate of laminin gamma 2 monomer, AFP, and PIVKA-II in CH specimens. Accordingly, the ROC graph was a plot of sensitivity (true positive frequency (TPF)) against specificity (false positive frequency (FPF)). A value of 1.000 represented 100% sensitivity and 100% specificity. This ROC graph is shown in FIG. 4C and the area under the curve (AUC) for each of laminin gamma 2 monomer, AFP, and PIVKA-II is shown in Table 4.

TABLE 4

| Marker | AUC |
| --- | --- |
| Laminin gamma 2 monomer | 0.793 |
| AFP | 0.788 |
| PIVKA-II | 0.845 |

Figure 10:
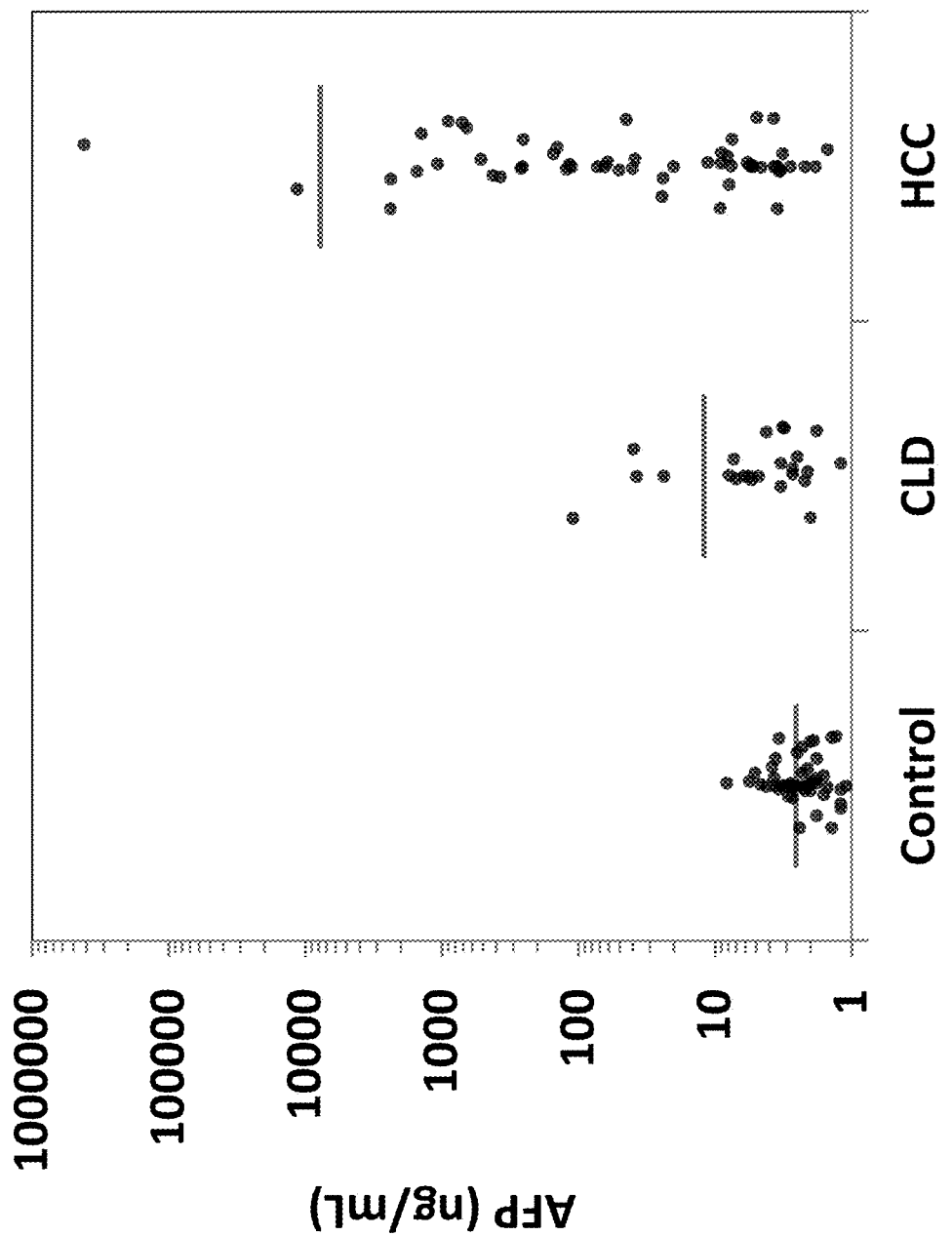
FIG. 10 shows a scatter plot of serum AFP concentrations determined in serum samples from normal subjects (Control) (n=52), patients with chronic liver disease (n=24), and patients with HCC (n=57). Abbreviations: CLD, chronic liver disease; HCC, hepatocellular carcinoma; AFP, alpha-fetoprotein; PIVKA-II, prothrombin induced by vitamin K absence-II; SE, standard error.
Figure 11:
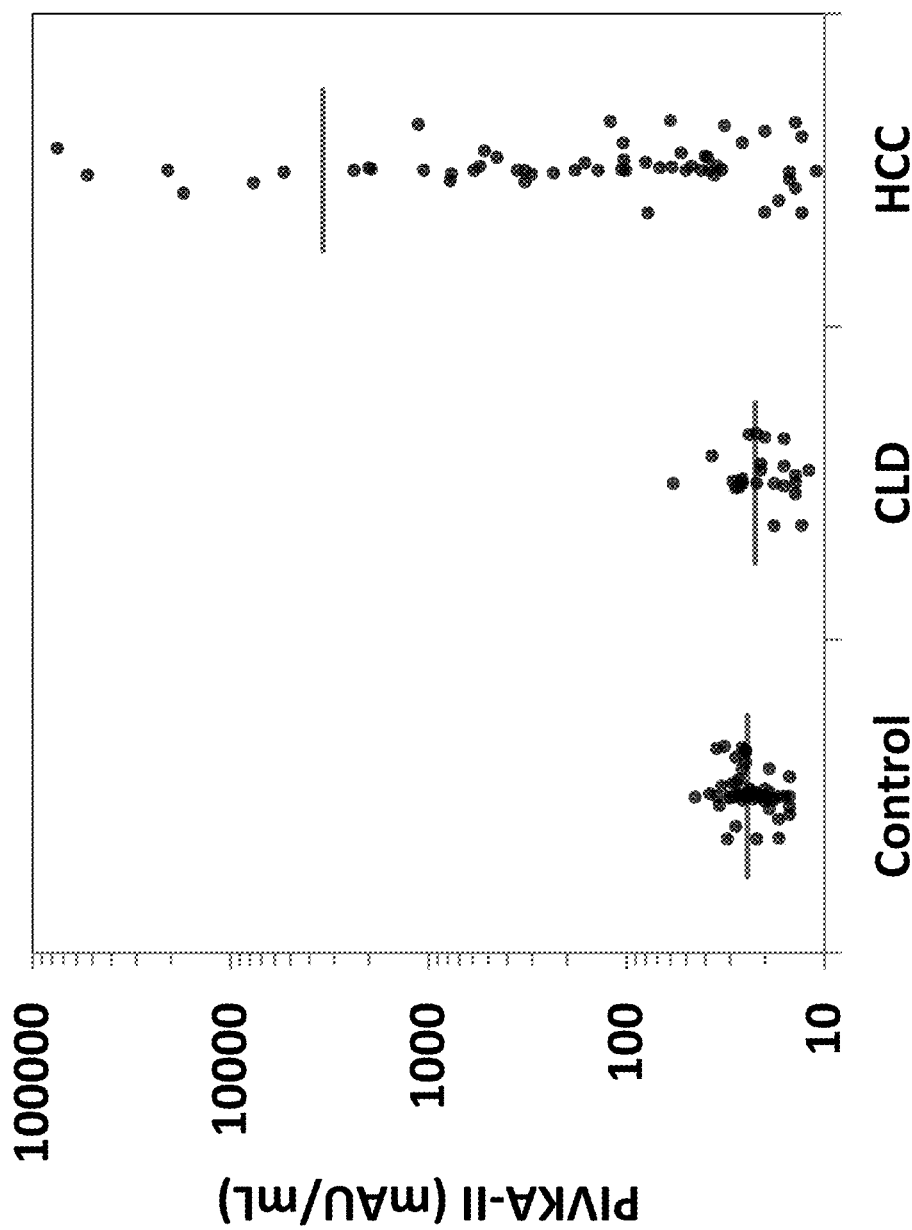
FIG. 11 shows a scatter plot of serum PIVKA-II concentrations determined in serum samples from normal subjects (Control) (n=52), patients with chronic liver disease (n=24), and patients with HCC (n=57). The horizontal lines represent median concentrations. Abbreviations: CLD, chronic liver disease; HCC, hepatocellular carcinoma; AFP, alpha-fetoprotein; PIVKA-II, prothrombin induced by vitamin K absence-II; SE, standard error.

The optimal cutoff value to distinguish HCC from non-malignant chronic liver disease was 116.6 pg/mL (FIG. 4C), with a sensitivity and specificity of 63% (95% CI, 49-76%) and 83% (95% CI, 63-95%), respectively. When distinguishing patients with chronic liver disease from those with HCC, PIVKA-II (ROC curve AUC=0.845; 95% CI, 76-93%) outperformed Ln-γ2 (ROC curve AUC=0.793; 95% CI, 69-89%; differences were not statistically significant) and AFP (ROC curve AUC=0.788; 95% CI, 69-89%). Ln-γ2 positivity (>116.6 pg/mL) was observed in 0/52 (0%), 4/24 (17%), and 36/57 (63%) subjects among healthy volunteers, patients with chronic liver disease, and patients with HCC, respectively. AFP positivity (>20 ng/mL; the upper normal limit reported in Japanese subjects) (6) was observed in 0/52 (0%), 4/24 (17%), and 30/57 (53%) subjects among healthy volunteers, patients with chronic liver disease, and patients with HCC, respectively. The median concentrations (range) of AFP were 2.3 ng/mL (healthy controls, range: 0.9-8.2 ng/mL), 3.8 ng/mL (chronic liver disease patients, range: 1.2-109.7 ng/mL), and 24.4 ng/mL (HCC patients, range: 1.5-417199 ng/mL) (FIG. 10). PIVKA-II positivity (>40 mAU/mL, the upper normal limit reported in Japanese subjects) (6) was observed in 1/52 (1.9%), 1/24 (40.2%), and 39/57 (68%) subjects among healthy volunteers, patients with chronic liver disease, and patients with HCC, respectively. The median concentrations (range) of PIVKA-II were 24.5 mAU/mL (healthy controls, range: 15.0-45.0 mAU/mL), 21.0 mAU/mL (patients with chronic liver disease, range: 12.0-58.0 mAU/mL), and 103 mAU/mL (patients with HCC, range: 11.0-75000 mAU/mL) (FIG. 11). Ln-γ2, AFP, and PIVKA-II levels were found to be significantly elevated ($p<0.001$) in sera from patients with HCC compared with sera from both healthy volunteers and patients with chronic liver disease. Ln-γ2 and AFP levels were found to be significantly elevated (p<0.01) in sera from patients with chronic liver disease compared with sera from healthy volunteers.

These results indicated that laminin gamma 2 monomer exhibited higher sensitivity and specificity as a marker for HCC than AFP and PIVKA-II, and thus, was a more accurate marker for HCC than AFP and PIVKA-II.

Figure 5A:
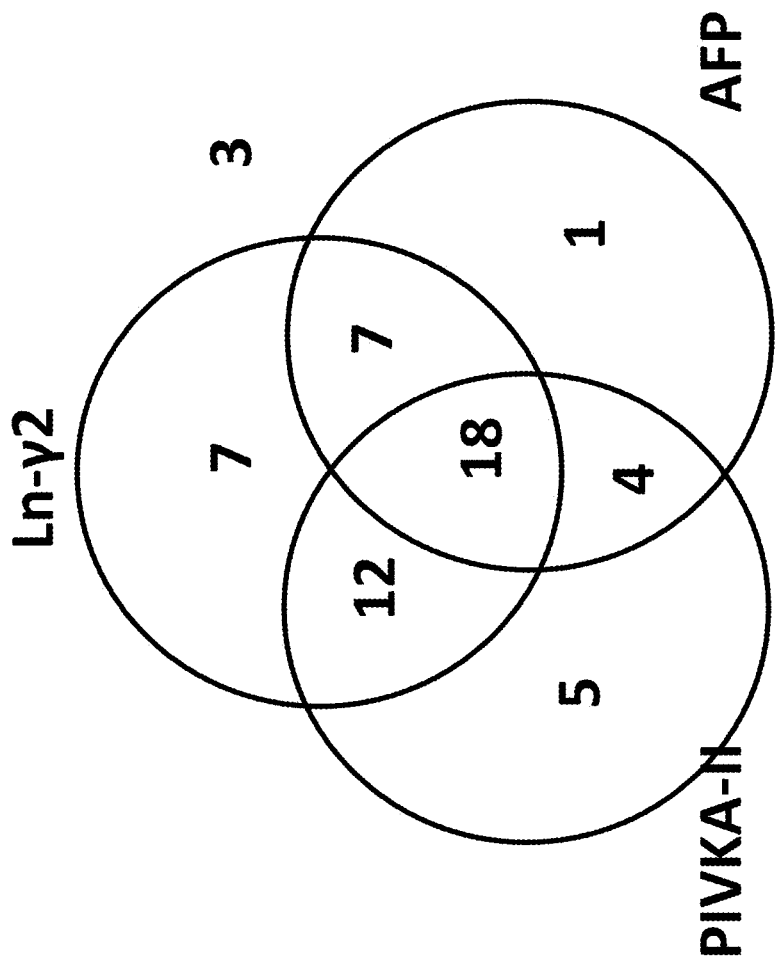
FIG. 5A shows a Venn diagram of subjects having HCC and elevated levels of laminin gamma 2 monomer (Ln-γ2), AFP, and/or PIVKA-II as compared to cutoff value (79.5 pg/mL, mean of healthy donor group+2SD). Each percentage value represented the percentage of HCC subjects that had an elevated level of the indicated marker as compared to each cutoff value.

Additionally, FIG. 5A and Table 5 show the positive rate of detecting HCC for laminin gamma 2 monomer, PIVKA-II, AFP, and combinations thereof. The cutoff of laminin gamma 2 monomer was the mean plus 2 standard deviations (Mean+2SD) for the healthy donor specimens, which was 79.5 pg/mL. Three HCC specimens were negative for all three of laminin gamma 2 monomer, PIVKA-II, and AFP.

TABLE 5

| Marker | Positive Rate of Detecting HCC |
| --- | --- |
| Laminin gamma 2 monomer | 77.2% |
| PIVKA-II | 68.4% |
| AFP | 52.6% |
| Laminin gamma 2 monomer and PIVKA-II | 93.0% |
| Laminin gamma 2 monomer and AFP | 86.0% |
| PIVKA-II and AFP | 82.5% |
| Laminin gamma 2 monomer, PIVKA-II, and AFP | 94.7% |

These results indicated that laminin gamma 2 monomer had a higher positive rate of detecting HCC than PIVKA-II or AFP. The positive rate of detecting HCC was the same for laminin gamma 2 monomer and the combination of AFP and PIVKA-II, i.e., 80%.

The positive rate of detecting HCC was increased when combining laminin gamma 2 monomer with PIVKA-II or AFP as compared to laminin gamma 2 monomer alone, i.e., 93.0% or 86.0% vs. 77.2%. However, the combination of all three markers provided a positive rate of detecting HCC (94.7%) that was equivalent to the positive rate of detecting HCC provided by the combination of laminin gamma 2 monomer and PIVKA-II (93.0%). Accordingly, the addition of AFP to the combination of laminin gamma 2 monomer and PIVKA-II did not further increase the positive rate of detecting HCC.

Figure 5B:
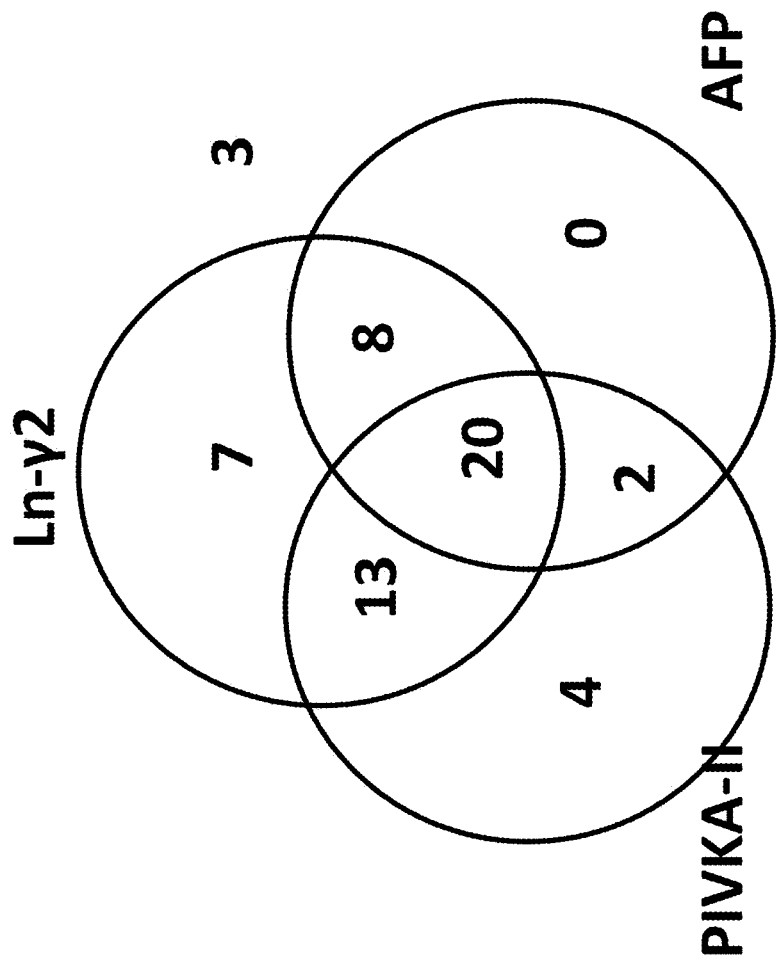
FIG. 5B shows a Venn diagram of subjects having HCC and elevated levels of laminin gamma 2 monomer (Ln-γ2), AFP, and/or PIVKA-II as compared to cutoff value (75.9 pg/mL, derived from ROC analysis). Each percentage value represented the percentage of HCC subjects that had an elevated level of the indicated marker as compared to each cutoff value.

FIG. 5B and Table 6 show the positive rate of detecting HCC for laminin gamma 2 monomer, PIVKA-II, AFP, and combinations thereof. the laminin gamma 2 monomer cutoff value was calculated from ROC analysis of HCC compared against healthy donors (HD), which was 75.9 pg/mL. Three HCC specimens were negative for all three of laminin gamma 2 monomer, PIVKA-II, and AFP.

TABLE 6

| Marker | Positive Rate of Detecting HCC |
| --- | --- |
| Laminin gamma 2 monomer | 84.2% |
| PIVKA-II | 68.4% |
| AFP | 52.6% |
| Laminin gamma 2 monomer and PIVKA-II | 94.7% |
| Laminin gamma 2 monomer and AFP | 87.7% |
| PIVKA-II and AFP | 82.5% |
| Laminin gamma 2 monomer, PIVKA-II, and AFP | 94.7% |

These results indicated that laminin gamma 2 monomer had a higher positive rate of detecting HCC than PIVKA-II or AFP. The positive rate of detecting HCC was the same for laminin gamma 2 monomer and the combination of AFP and PIVKA-II, i.e., 80%.

The positive rate of detecting HCC was increased when combining laminin gamma 2 monomer with PIVKA-II or AFP as compared to laminin gamma 2 monomer alone, i.e., 84.2% or 94.7% vs. 87.7%. However, the combination of all three markers provided a positive rate of detecting HCC (94.7%) that was equivalent to the positive rate of detecting HCC provided by the combination of laminin gamma 2 monomer and PIVKA-II (94.7%). Accordingly, the addition of AFP to the combination of laminin gamma 2 monomer and PIVKA-II did not further increase the positive rate of detecting HCC.

Figure 5C:
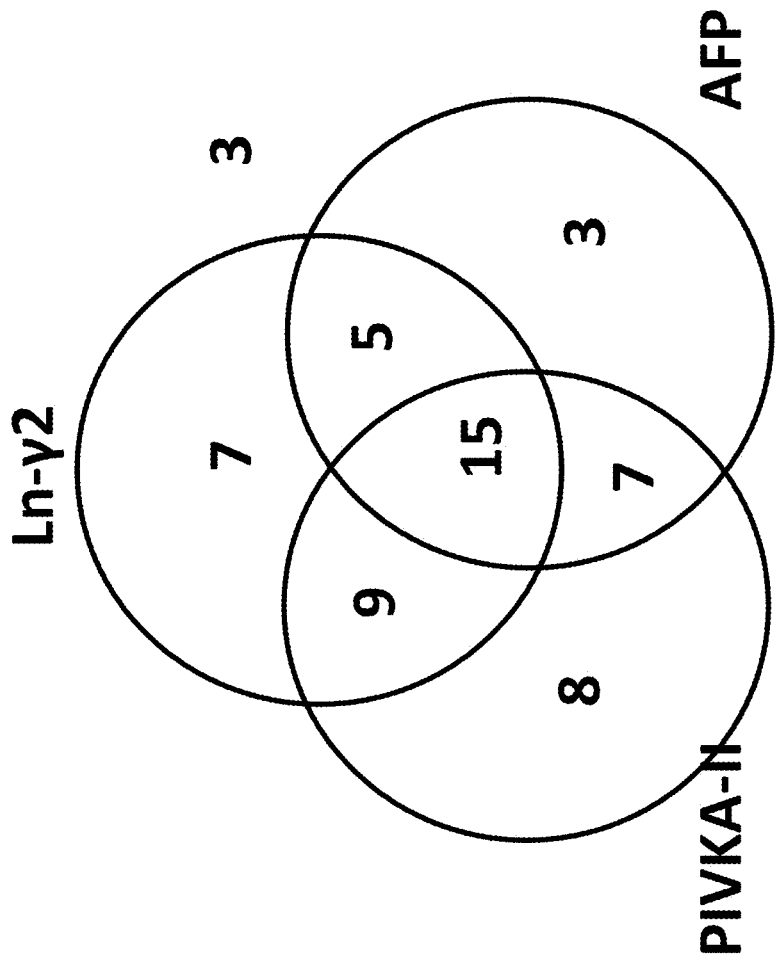
FIG. 5C shows a Venn diagram of subjects having HCC and elevated levels of laminin gamma 2 monomer (Ln-γ2), AFP, and/or PIVKA-II as compared to cutoff value (116.6 pg/mL, the optimal cutoff value to distinguish HCC from non-malignant chronic liver disease). Each percentage value represented the percentage of HCC subjects that had an elevated level of the indicated marker as compared to each cutoff value.

FIG. 5C and Table 7 show the positive rate of detecting HCC for laminin gamma 2 monomer (>116.6 pg/mL), PIVKA-II (>40 mAU/mL), AFP (>20 ng/mL), and combinations thereof. The laminin gamma 2 monomer cutoff value was calculated from ROC analysis of HCC compared against hepatitis (CH) specimens, which was 116.6 pg/mL. While the combination of Ln-γ2 and PIVKA-II was detected in 51/57 patients (89.5%), the combination of Ln-γ2 and AFP was detected in 46/57 (80.7%) and the combination of PIVKA-II and AFP in 47/57 (82.5%). The combination of all 3 markers was detected in 54/57 patients (94.7%). Interestingly, 67% (12/18) of patients who were negative for PIVKA-II exhibited positivity for Ln-γ2. Three HCC specimens were negative for all three of laminin gamma 2 monomer, PIVKA-II, and AFP.

TABLE 7

| Marker | Positive Rate of Detecting HCC |
| --- | --- |
| Laminin gamma 2 monomer | 63.2% |
| PIVKA-II | 68.4% |
| AFP | 52.6% |
| Laminin gamma 2 monomer and PIVKA-II | 89.5% |
| Laminin gamma 2 monomer and AFP | 80.7% |
| PIVKA-II and AFP | 82.5% |
| Laminin gamma 2 monomer, PIVKA-II, and AFP | 94.7% |

These results indicated that laminin gamma 2 monomer had a higher positive rate of detecting HCC than PIVKA-II or AFP. The positive rate of detecting HCC was the same for laminin gamma 2 monomer and the combination of AFP and PIVKA-II, i.e., 80%.

The positive rate of detecting HCC was increased when combining laminin gamma 2 monomer with PIVKA-II or AFP as compared to laminin gamma 2 monomer alone, i.e., 63.2% or 89.5% vs. 80.7%. However, the combination of all three markers provided a positive rate of detecting HCC (94.7%) that was equivalent to the positive rate of detecting HCC provided by the combination of laminin gamma 2 monomer and PIVKA-II (89.5%). Accordingly, the addition of AFP to the combination of laminin gamma 2 monomer and PIVKA-II did not further increase the positive rate of detecting HCC.

Example 6

Serum Concentration of Laminin Gamma 2 Monomer in Stages III and IV of Pancreatic Cancer As described in Example 3, the serum concentration of laminin gamma 2 monomer was higher in pancreatic cancer specimens. The pancreatic cancer specimens were further examined with regards to the serum concentration of laminin gamma 2 monomer in different stages of pancreatic cancer. Specifically, the immunoassay described in Example 2 was used to detect serum concentrations of laminin gamma 2 monomer from stage III pancreatic cancer and stage IV pancreatic cancer specimens as well as pancreatitis and healthy donor specimens. Serum samples were collected from the specimens and diluted in the above-described sample diluent.

Results.

Figure 6A:
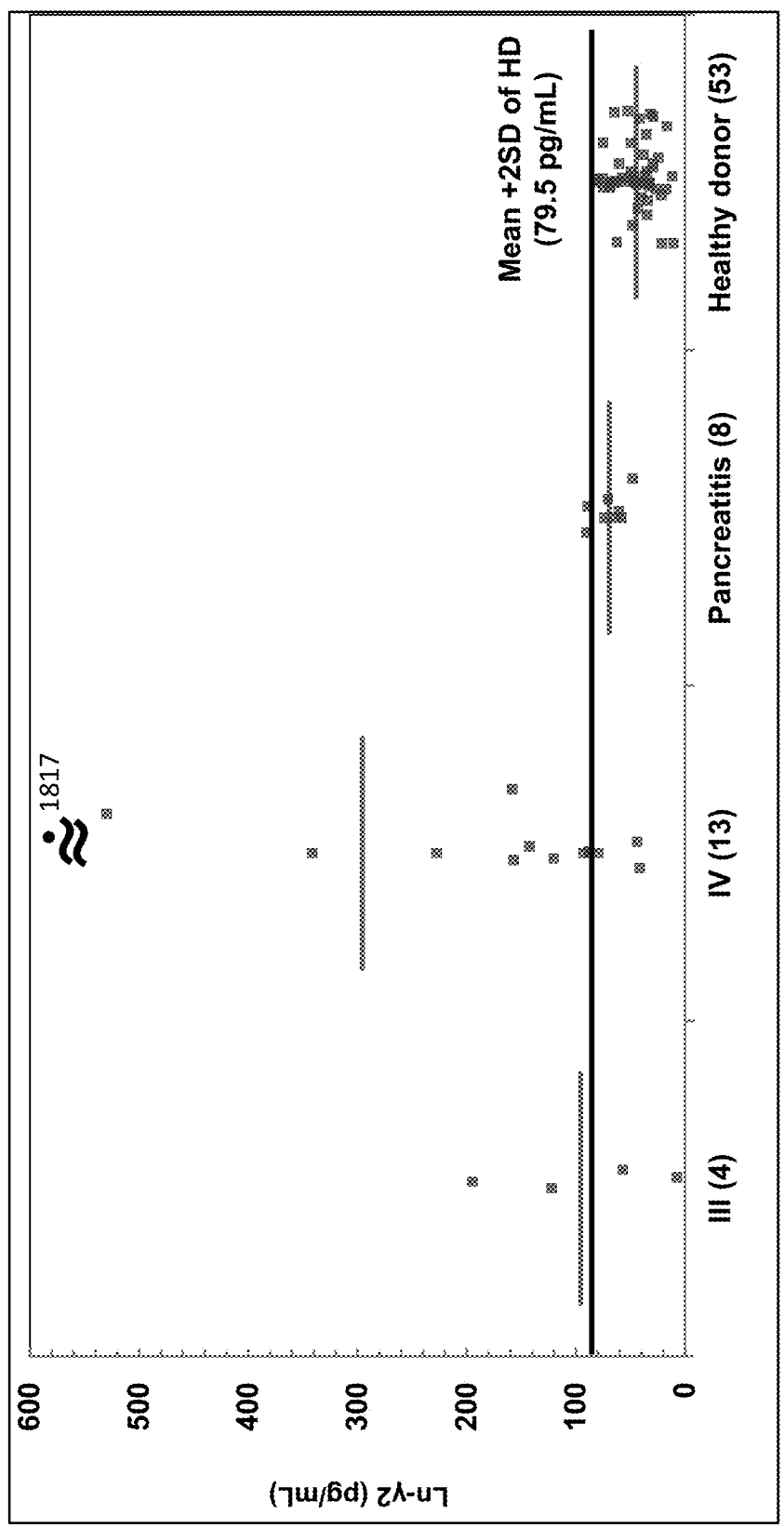
FIG. 6A shows a graph plotting subject group against serum concentration (pg/mL) of laminin gamma 2 monomer. The designations "III" and "IV" represented the subject groups having stage III pancreatic cancer and stage IV pancreatic cancer, respectively. For each subject group, the number in parenthesis represented the number of subjects in the group and the solid line represented the mean serum concentration (pg/mL) of laminin gamma 2 monomer for the group. The solid line extending the length of the x-axis represented the mean plus 2 standard deviations (Mean+2SD) for the healthy donor subject group, which was 79.5 pg/mL.
Figure 6B:
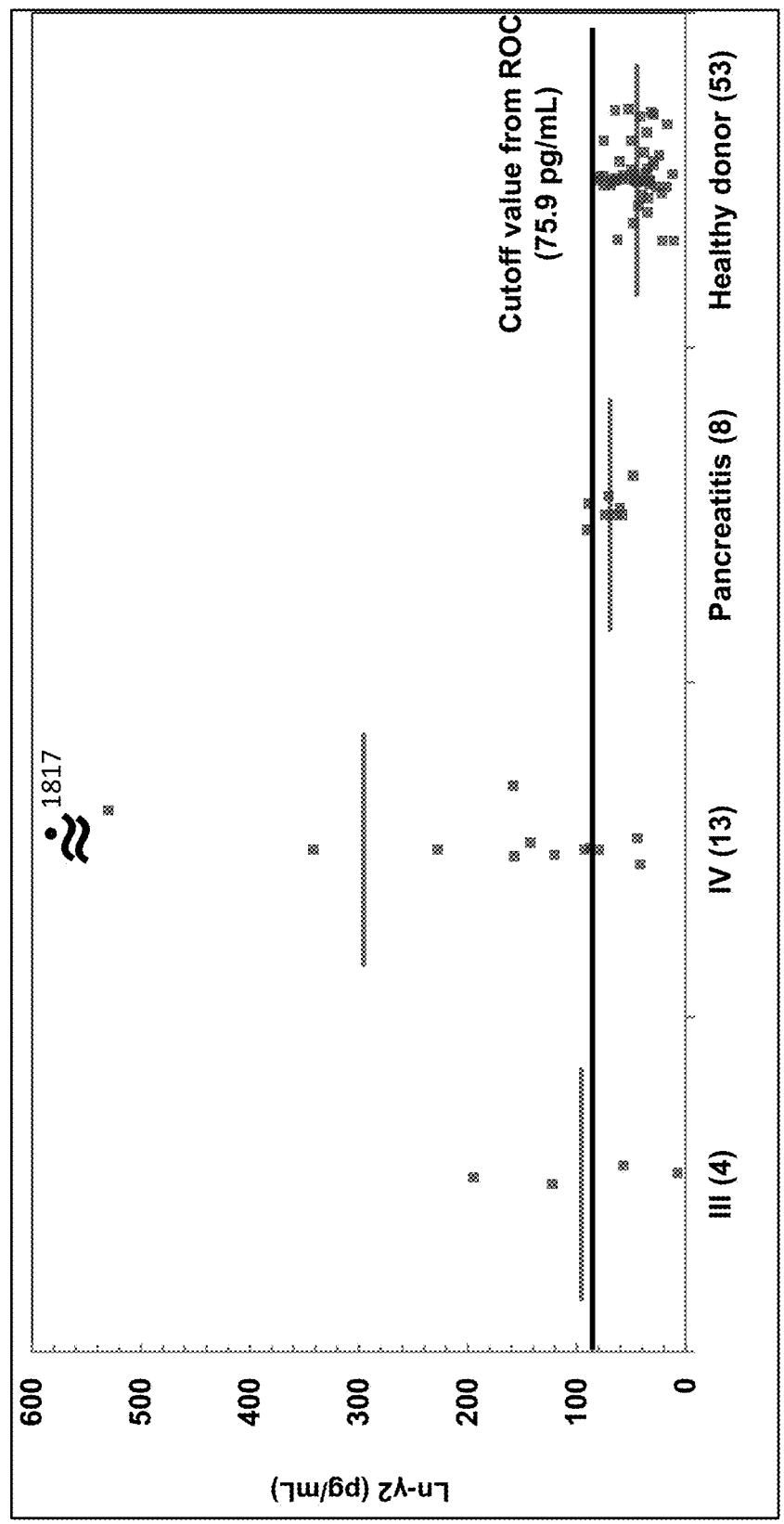
FIG. 6B shows a graph plotting subject group against serum concentration (pg/mL) of laminin gamma 2 monomer. The designations "III" and "IV" represented the subject groups having stage III pancreatic cancer and stage IV pancreatic cancer, respectively. For each subject group, the number in parenthesis represented the number of subjects in the group and the solid line represented the mean serum concentration (pg/mL) of laminin gamma 2 monomer for the group. The solid line extending the length of the x-axis represented the cutoff value derived from ROC analysis, which was 75.9 pg/mL.

The results of these studies are shown in FIGS. 6A and 6B, which show the serum concentration (pg/mL) of laminin gamma 2 monomer for each group of indicated specimens. Each specimen was depicted with a solid square. The mean serum concentration of laminin gamma 2 monomer for each specimen group was indicated with a solid line. The solid line extending the length of the x-axis indicated the mean plus 2 standard deviations (Mean+2SD) for the healthy donor specimens, which was 79.5 pg/mL in FIG. 6A. The solid line extending the length of the x-axis represented the cutoff value derived from ROC analysis, which was 75.9 pg/mL in FIG. 6B.

As shown in FIGS. 6A and 6B, elevate serum concentrations of laminin gamma 2 monomer were observed in stage III pancreatic cancer and stage IV pancreatic cancer as compared to pancreatitis and healthy donor specimens. Accordingly, these results indicated that laminin gamma 2 monomer levels in serum increased with stage of pancreatic cancer (i.e., increased in a stage-dependent manner).

Example 7

Figure 7:
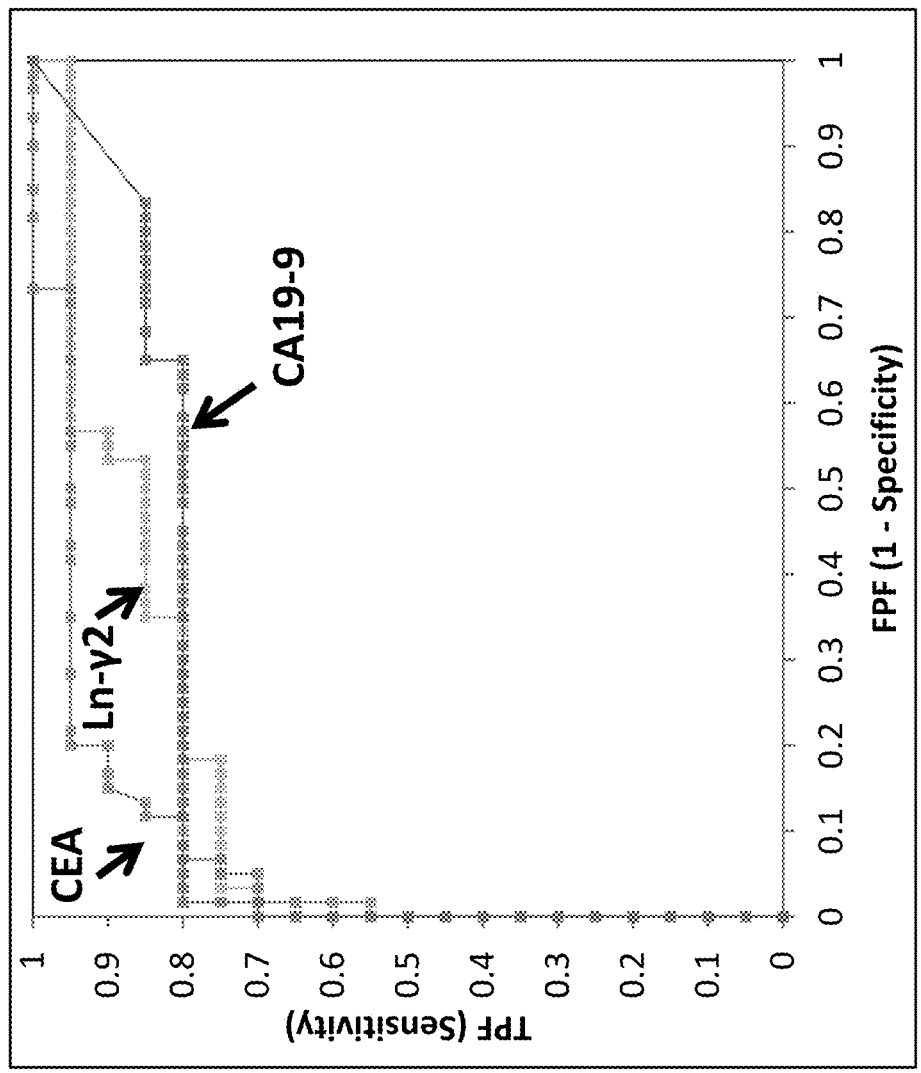
FIG. 7 shows a Receiver Operator Characteristic (ROC) graph for the markers laminin gamma 2 monomer (Ln-γ2), CEA, and CA19-9, in which subjects having pancreatic cancer were compared against subjects having pancreatitis and healthy donor subjects.

Specificity and Sensitivity of Laminin Gamma 2 Monomer as a Marker for Pancreatic Cancer The specificity and sensitivity of laminin gamma 2 monomer, carcinoembryonic (CEA), and carbohydrate antigen 19-9 (CA19-9) as markers for pancreatic cancer were examined. Specifically, the level of each marker was examined in 20 pancreatic cancer specimens and 60 pancreatitis or healthy donor specimens, for a total of 80 specimens. A receiver operator characteristic (ROC) graph was generated by plotting the observed true positive rate of laminin gamma 2 monomer, CEA, and CA19-9 in the pancreatic cancer specimens against the observed false positive rate of laminin gamma 2 monomer, CEA, and CA19-9 in the healthy donor and pancreatitis specimens. Accordingly, the ROC graph was a plot of sensitivity (true positive frequency (TPF)) against specificity (false positive frequency (FPF)). A value of 1.000 represented 100% sensitivity and 100% specificity. This ROC graph is shown in FIG. 7 and the area under the curve (AUC) for each of laminin gamma 2 monomer, CEA, and CA19-9 is shown in Table 8.

TABLE 8

| Marker | AUC |
|---|---|
| Laminin gamma 2 monomer | 0.866 |
| CEA | 0.932 |
| CA19-9 | 0.828 |

These results indicated that laminin gamma 2 monomer exhibited higher sensitivity and specificity as a marker for pancreatic cancer than CA19-9, and thus, was a more accurate marker for pancreatic cancer than CA19-9.

Figure 8:
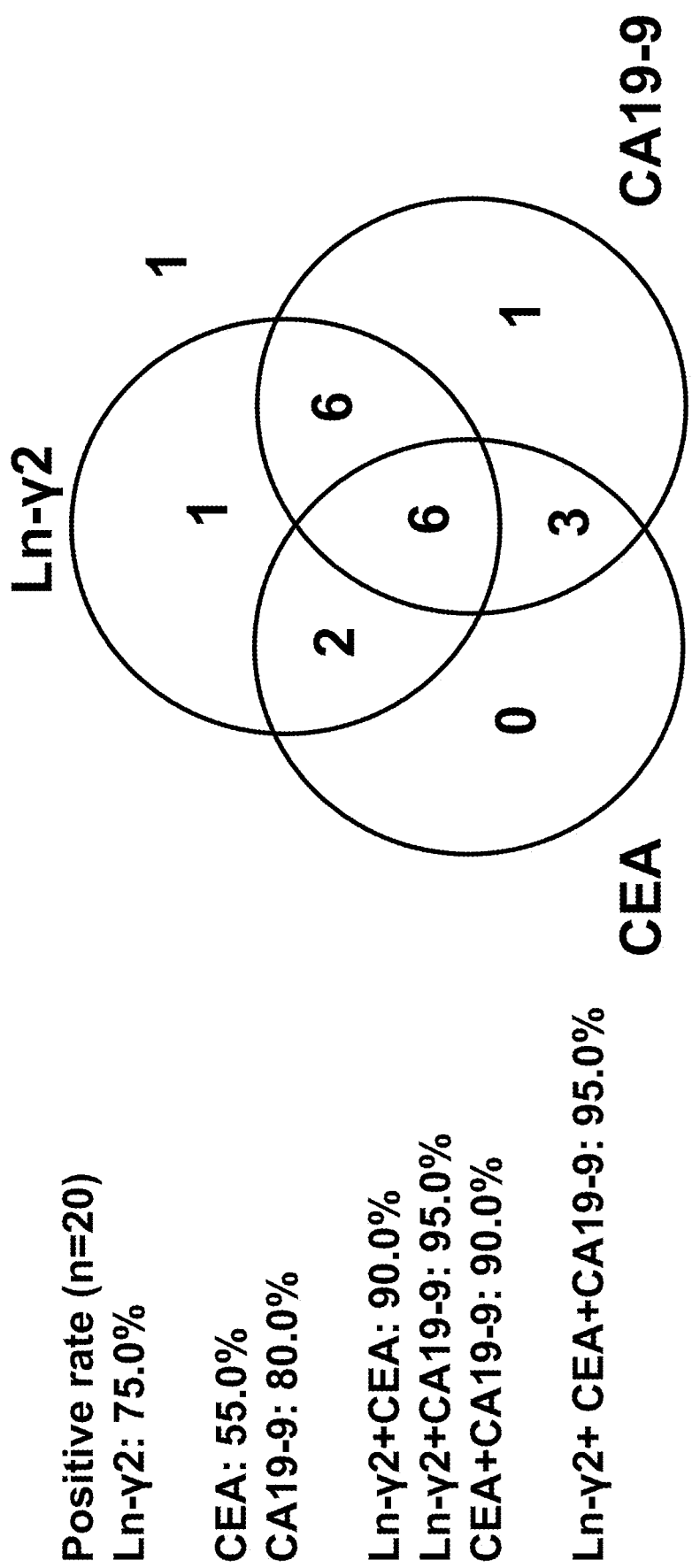
FIG. 8 shows a Venn diagram of subjects having pancreatic cancer and elevated levels of laminin gamma 2 monomer (Ln-γ2), CEA, and/or CA19-9 as compared to cutoff value. Each percentage value represented the percentage of pancreatic cancer subjects that had an elevated level of the indicated marker as compared to each cutoff value.

Additionally, FIG. 8 and Table 9 show the positive rate of detecting pancreatic cancer for laminin gamma 2 monomer, CEA, and CA19-9, and combinations thereof. One pancreatic cancer specimen was negative for all three of laminin gamma 2 monomer, CEA, and CA19-9.

TABLE 9

| Marker | Positive Rate of Detecting Pancreatic Cancer |
|---|---|
| Laminin gamma 2 monomer | 75.0% |
| CEA | 55.0% |
| CA19-9 | 80.0% |
| Laminin gamma 2 monomer and CEA | 90.0% |
| Laminin gamma 2 monomer and CA19-9 | 95.0% |
| CEA and CA19-9 | 90.0% |
| Laminin gamma 2 monomer, CEA, and CA19-9 | 95.0% |

These results indicated that laminin gamma 2 monomer was a marker for diagnosis of pancreatic cancer. Additionally, the positive rate of detecting pancreatic cancer was higher for the combinations of laminin gamma 2 monomer, CEA, and CA19-9 as compared to the positive rate of detecting pancreatic cancer for each of laminin gamma 2 monomer, CEA, and CA19-9.

7. Clauses

For reasons of completeness, various aspects of the invention are set out in the following numbered clauses:

Clause 1. A method of diagnosing hepatocellular carcinoma (HCC) in a subject in need thereof, the method comprising: (a) obtaining a biological sample from the subject; (b) determining a level of laminin gamma 2 monomer in the biological sample; (c) comparing the level of laminin gamma 2 monomer to a reference level of laminin gamma 2 monomer; and (d) identifying the subject as having HCC when the level of laminin gamma 2 monomer is greater than the reference level of laminin gamma 2 monomer.

Clause 2. The method of clause 1, further comprising determining a level of at least one additional biomarker in the biological sample, wherein the at least one additional biomarker is selected from the group consisting of: protein induced vitamin K antagonist-II (PIVKA-II), alpha fetal protein (AFP), and the combination thereof.

Clause 3. The method of clause 2, further comprising comparing the level of the at least one additional biomarker to a reference level of the at least one additional biomarker; and identifying the subject as having HCC when the level of the at least one additional biomarker is greater than the reference level of the at least on additional biomarker.

Clause 4. The method of any one of clauses 1-3, wherein the levels of: (a) laminin gamma 2 monomer and PIVKA-II are determined in the biological sample; (b) laminin gamma 2 monomer and AFP are determined in the biological sample; or (c) laminin gamma 2 monomer, PIVKA-II, and AFP are determined in the biological sample.

Clause 5. The method of clause 4, wherein the subject is identified as having HCC when: (a) the levels of laminin gamma 2 monomer and PIVKA-II in the biological sample are greater than the reference levels of laminin gamma 2 monomer and PIVKA-II; (b) the levels of laminin gamma 2 monomer and AFP in the biological sample are greater than the reference levels of laminin gamma 2 monomer and AFP; or (c) the levels of laminin gamma 2 monomer, PIVKA-II, and AFP in the biological sample are greater than the reference levels of laminin gamma 2 monomer, PIVKA-II, and AFP.

Clause 6. The method of any one of clauses 1-5, wherein the biological sample is selected from the group consisting of: a whole blood sample, a plasma sample, and a serum sample.

Clause 7. The method of clause 6, wherein the biological sample is a serum sample.

Clause 8. The method of any one of clauses 1-7, wherein determining the level of laminin gamma 2 monomer in the biological sample includes detecting laminin gamma 2 monomer with an immunoassay.

Clause 9. The method of any one of clauses 2-8, wherein determining the level of PIVKA-II and AFP in the biological sample includes detecting PIVKA-II and AFP with an immunoassay.

Clause 10. The method of clause 8 or 9, wherein the immunoassay is a sandwich immunoassay.

Clause 11. The method of any one of clauses 2-10, wherein the reference level of PIVKA-II and AFP is a level of PIVKA-II and AFP in a control sample.

Clause 12. The method of any one of clauses 1-11, wherein the reference level of laminin gamma 2 monomer is a level of laminin gamma 2 monomer in a control sample.

Clause 13. The method of any one of clauses 1-12, wherein the reference level of laminin gamma 2 monomer is a cutoff level.

Clause 14. The method of clause 13, wherein the cutoff level is determined by a mean plus 2 standard deviation analysis of multiple control samples.

Clause 15. The method of any one of clauses 1-14, wherein the reference level of laminin gamma 2 monomer is a level of laminin gamma 2 monomer in a calibrator.

Clause 16. A method of determining if a subject has or is at risk of developing hepatocellular carcinoma (HCC), the method comprising: (a) obtaining a biological sample from the subject; (b) measuring a level of laminin gamma 2 monomer in the biological sample; (c) comparing the level of laminin gamma 2 monomer to a reference level of laminin gamma 2 monomer; and (d) determining the subject has or is at risk of developing HCC when the level of laminin gamma 2 monomer is greater than the reference level of laminin gamma 2 monomer.

Clause 17. The method of clause 16, further comprising measuring a level of at least one additional biomarker in the biological sample, wherein the at least one additional biomarker is selected from the group consisting of: protein induced vitamin K antagonist-II (PIVKA-II), alpha fetal protein (AFP), and the combination thereof.

Clause 18. The method of clause 17, further comprising comparing the level of the at least one additional biomarker to a reference level of the at least one additional biomarker; and determining the subject has or is at risk of developing HCC when the level of the at least one additional biomarker is greater than the reference level of the at least one additional biomarker.

Clause 19. The method of any one of clauses 16-18, wherein the level of (a) laminin gamma 2 monomer and PIVKA-II are determined in the biological sample; (b) laminin gamma 2 monomer and AFP are determined in the biological sample; or (c) laminin gamma 2 monomer, PIVKA-II, and AFP are determined in the biological sample.

Clause 20. The method of clause 19, wherein the subject is identified as having HCC when: (a) the levels of laminin gamma 2 monomer and PIVKA-II in the biological sample are greater than the reference levels of laminin gamma 2 monomer and PIVKA-II; (b) the levels of laminin gamma 2 monomer and AFP in the biological sample are greater than the reference levels of laminin gamma 2 monomer and AFP; or (c) the levels of laminin gamma 2 monomer, PIVKA-II, and AFP in the biological sample are greater than the reference levels of laminin gamma 2 monomer, PIVKA-II, and AFP.

Clause 21. The method of any one of clauses 16-20, wherein the biological sample is selected from the group consisting of: a whole blood sample, a plasma sample, and a serum sample.

Clause 22. The method of clause 21, wherein the biological sample is a serum sample.

Clause 23. The method of any one of clauses 16-22, wherein determining the level of laminin gamma 2 monomer in the biological sample includes detecting laminin gamma 2 monomer with an immunoassay.

Clause 24. The method of any one of clauses 17-23, wherein determining the level of PIVKA-II and AFP in the biological sample includes detecting PIVKA-II and AFP with an immunoassay.

Clause 25. The method of clause 23 or 24, wherein the immunoassay is a sandwich immunoassay.

Clause 26. The method of any one of clauses 17-25, wherein the reference level of PIVKA-II and AFP is a level of PIVKA-II and AFP in a control sample.

Clause 27. The method of any one of clauses 16-26, wherein the reference level of laminin gamma 2 monomer is a level of laminin gamma 2 monomer in a control sample.

Clause 28. The method of any one of clauses 16-27, wherein the reference level of laminin gamma 2 monomer is a cutoff level.

Clause 29. The method of clause 28, wherein the cutoff level is determined by a mean plus 2 standard deviation analysis of multiple control samples.

Clause 30. The method of any one of clauses 16-29, wherein the reference level of laminin gamma 2 monomer is a level of laminin gamma 2 monomer in a calibrator.

Clause 31. A method of monitoring progression of hepatocellular carcinoma (HCC) in a subject in need thereof, the method comprising: (a) obtaining first and second biological samples from the subject; (b) measuring a first level of laminin gamma 2 monomer in the first biological sample and a second level of laminin gamma 2 monomer in the second biological sample; (c) comparing the first and second levels of laminin gamma 2 monomer; and (d) determining (i) HCC has progressed in the subject when the second level of laminin gamma 2 monomer is greater than the first level of laminin gamma 2 monomer or (ii) HCC has not progress in the subject when the second level of laminin gamma 2 monomer is equivalent to or less than the first level of laminin gamma 2 monomer.

Clause 32. The method of clause 31, further comprising measuring a first level of at least one additional biomarker in the first biological sample and a second level of the at least one additional biomarker in the second biological sample, wherein the at least one additional biomarker is selected from the group consisting of: protein induced vitamin K antagonist-II (PIVKA-II), alpha fetal protein (AFP), and the combination thereof.

Clause 33. The method of clause 32, further comprising comparing the first and second levels of the at least one additional biomarker; and determining HCC has progressed in the subject when the second level of the at least one additional biomarker is greater than the first level of the at least one additional biomarker, or HCC has not progressed in the subject when the second level of the at least one additional biomarker is equivalent to or less than the first level of the at least one additional biomarker.

Clause 34. The method of any one of clauses 31-33, wherein the first and second levels of (a) laminin gamma 2 monomer and PIVKA-II are measured in the first and second biological samples; (b) laminin gamma 2 monomer and AFP are measured in the first and second biological samples; or (c) laminin gamma 2 monomer, PIVKA-II, and AFP are measured in the first and second biological samples.

Clause 35. The method of clause 34, wherein the subject is identified as having HCC when: (a) the levels of laminin gamma 2 monomer and PIVKA-II in the biological sample are greater than the reference levels of laminin gamma 2 monomer and PIVKA-II; (b) the levels of laminin gamma 2 monomer and AFP in the biological sample are greater than the reference levels of laminin gamma 2 monomer and AFP; or (c) the levels of laminin gamma 2 monomer, PIVKA-II, and AFP in the biological sample are greater than the reference levels of laminin gamma 2 monomer, PIVKA-II, and AFP.

Clause 36. The method of any one of clauses 31-35, wherein the first and second biological samples are whole blood samples, plasma samples or serum samples.

Clause 37. The method of clause 36, wherein the first and second biological samples are serum samples.

Clause 38. The method of any one of clauses 31-37, wherein determining the level of laminin gamma 2 monomer in the biological sample includes detecting laminin gamma 2 monomer with an immunoassay.

Clause 39. The method of any one of clauses 32-38, wherein determining the level of PIVKA-II and AFP in the biological sample includes detecting PIVKA-II and AFP with an immunoassay.

Clause 40. The method of clause 38 or 39, wherein the immunoassay is a sandwich immunoassay.

Clause 41. The method of any one of clauses 32-40, wherein the reference level of PIVKA-II and AFP is a level of PIVKA-II and AFP in a control sample.

Clause 42. The method of any one of clauses 31-41, wherein the reference level of laminin gamma 2 monomer is a level of laminin gamma 2 monomer in a control sample.

Clause 43. The method of any one of clauses 31-42, wherein the reference level of laminin gamma 2 monomer is a cutoff level.

Clause 44. The method of clause 43, wherein the cutoff level is determined by a mean plus 2 standard deviation analysis of multiple control samples.

Clause 45. The method of any one of clauses 31-44, wherein the reference level of laminin gamma 2 monomer is a level of laminin gamma 2 monomer in a calibrator.

Clause 46. A kit for detecting HCC in a subject in need thereof, the kit comprising one or more reagents for detecting laminin gamma 2 monomer.

Clause 47. The kit of clause 46, further comprising (a) one or more reagents for detecting protein induced vitamin K antagonist-II (PIVKA-II); and (b) one or more reagents for detecting alpha fetal protein (AFP).

Clause 48. A method for diagnosing pancreatic cancer in a subject in need thereof, the method comprising: (a) obtaining a biological sample from the subject; (b) determining a level of laminin gamma 2 monomer in the biological sample; (c) determining a level of at least one additional biomarker in the biological sample, wherein the at least one additional biomarker is selected from the group consisting of: carcinoembryonic antigen (CEA) and carbohydrate antigen 19-9 (CA19-9); (d) comparing the level of laminin gamma 2 monomer to a reference level of laminin gamma 2 monomer and the level of the at least one additional biomarker to a reference level of the at least one additional biomarker; and (e) identifying the subject has having pancreatic cancer when the levels of laminin gamma 2 monomer and the at least one additional biomarker are greater than the reference levels of laminin gamma 2 monomer and the at least one additional biomarker.

Clause 49. The method of clause 48, wherein the levels of: (a) laminin gamma 2 monomer and CEA are determined in the biological sample; (b) laminin gamma 2 monomer and CA19-9 are determined in the biological sample; or (c) laminin gamma 2 monomer, CEA, and CA19-9 are determined in the biological sample.

Clause 50. The method of clause 48 or 49, wherein the biological sample is selected from the group consisting of: a whole blood sample, a plasma sample, and a serum sample.

Clause 51. The method of clause 50, wherein the biological sample is a serum sample.

Clause 52. The method of any one of clauses 48-51, wherein determining the level of laminin gamma 2 monomer in the biological sample includes detecting laminin gamma 2 monomer with an immunoassay.

Clause 53. The method of any one of clauses 49-52, wherein determining the level of CEA and CA19-9 in the biological sample includes detecting CEA and CA19-9 with an immunoassay.

Clause 54. The method of clause 52 or 53, wherein the immunoassay is a sandwich immunoassay.

Clause 55. The method of any one of clauses 49-54, wherein the reference level of CEA and CA19-9 is a level of CEA and CA19-9 in a control sample.

Clause 56. The method of any one of clauses 48-55, wherein the reference level of laminin gamma 2 monomer is a level of laminin gamma 2 monomer in a control sample.

Clause 57. The method of any one of clauses 48-56, wherein the reference level of laminin gamma 2 monomer is a cutoff level.

Clause 58. The method of clause 57, wherein the cutoff value is determined by a mean plus 2 standard deviation analysis of multiple control samples.

Clause 59. The method of any one of clauses 48-58, wherein the reference level of laminin gamma 2 monomer is a level of laminin gamma 2 monomer in a calibrator.

Clause 60. A method of determining if a subject has or is at risk of developing pancreatic cancer, the method comprising: (a) obtaining a biological sample from the subject; (b) measuring a level of laminin gamma 2 monomer in the biological sample; (c) measuring a level of at least one additional biomarker in the biological sample, wherein the at least one additional biomarker is selected from the group consisting of: carcinoembryonic antigen (CEA) and carbohydrate antigen 19-9 (CA19-9); (d) comparing the level of laminin gamma 2 monomer to a reference level of laminin gamma 2 monomer and the level of the at least one additional biomarker to a reference level of the at least one additional biomarker; and (e) determining the subject has or is at risk of developing pancreatic cancer when the levels of laminin gamma 2 monomer and the at least one additional biomarker are greater than the reference levels of laminin gamma 2 monomer and the at least one additional biomarker.

Clause 61. The method of clause 60, wherein the levels of: (a) laminin gamma 2 monomer and CEA in the biological sample are measured; (b) laminin gamma 2 monomer and CA19-9 in the biological sample are measured; or (c)

laminin gamma 2 monomer, CEA, and CA19-9 in the biological sample are measured.

Clause 62. The method of clause 60 or 61, wherein the biological sample is selected from the group consisting of: a whole blood sample, a plasma sample, and a serum sample.

Clause 63. The method of clause 62, wherein the biological sample is a serum sample.

Clause 64. The method of any one of clauses 60-63, wherein determining the level of laminin gamma 2 monomer in the biological sample includes detecting laminin gamma 2 monomer with an immunoassay.

Clause 65. The method of any one of clauses 61-64, wherein determining the level of CEA and CA19-9 in the biological sample includes detecting CEA and CA19-9 with an immunoassay.

Clause 66. The method of clause 64 or 65, wherein the immunoassay is a sandwich immunoassay.

Clause 67. The method of any one of clauses 61-66, wherein the reference level of CEA and CA19-9 is a level of CEA and CA19-9 in a control sample.

Clause 68. The method of any one of clauses 60-67, wherein the reference level of laminin gamma 2 monomer is a level of laminin gamma 2 monomer in a control sample.

Clause 69. The method of any one of clauses 60-68, wherein the reference level of laminin gamma 2 monomer is a cutoff level.

Clause 70. The method of clause 69, wherein the cutoff value is determined by a mean plus 2 standard deviation analysis of multiple control samples.

Clause 71. The method of any one of clauses 60-70, wherein the reference level of laminin gamma 2 monomer is a level of laminin gamma 2 monomer in a calibrator.

Clause 72. A method of monitoring progression of pancreatic cancer in a subject in need thereof, the method comprising: (a) obtaining first and second biological samples from the subject; (b) measuring a first level of laminin gamma 2 monomer in the first biological sample and a second level of laminin gamma 2 monomer in the second biological sample; (c) measuring a first level of at least one additional biomarker in the first biological sample and a second level of the at least one additional biomarker in the second biological sample, wherein the at least one additional biomarker is selected from the group consisting of: carcinoembryonic antigen (CEA) and carbohydrate antigen 19-9 (CA19-9); (d) comparing the first and second levels of laminin gamma 2 monomer; (e) comparing the first and second levels of the at least one additional biomarker; and (f) determining (i) the pancreatic cancer has progressed in the subject when the second levels of laminin gamma 2 monomer and the at least one additional biomarker are greater than the first levels of laminin gamma 2 monomer and the at least one additional biomarker or (ii) the pancreatic cancer has not progressed in the subject when the second levels of laminin gamma 2 monomer and the at least one additional biomarker are equivalent to or less than the first levels of laminin gamma 2 monomer and the at least one additional biomarker.

Clause 73. The method of clause 72, wherein: (i) the first and second levels of laminin gamma 2 monomer and CEA in the first and second biological samples are measured; (ii) the first and second levels of laminin gamma 2 monomer and CA19-9 in the first and second biological samples are measured; or (iii) the first and second levels of laminin gamma 2 monomer, CEA, and CA19-9 in the first and second biological samples are measured.

Clause 74. The method of clause 72 or 73, wherein the first and second biological samples are whole blood samples, plasma samples, and serum samples.

Clause 75. The method of clause 74 wherein the first and second biological samples are serum samples.

Clause 76. The method of any one of clauses 72-75, wherein determining the level of laminin gamma 2 monomer in the biological sample includes detecting laminin gamma 2 monomer with an immunoassay.

Clause 77. The method of any one of clauses 73-76, wherein determining the level of CEA and CA19-9 in the biological sample includes detecting CEA and CA19-9 with an immunoassay.

Clause 78. The method of clause 76 or 77, wherein the immunoassay is a sandwich immunoassay.

Clause 79. The method of any one of clauses 73-78, wherein the reference level of CEA and CA19-9 is a level of CEA and CA19-9 in a control sample.

Clause 80. The method of any one of clauses 72-79, wherein the reference level of laminin gamma 2 monomer is a level of laminin gamma 2 monomer in a control sample.

Clause 81. The method of any one of clauses 72-80, wherein the reference level of laminin gamma 2 monomer is a cutoff level.

Clause 82. The method of clause 81, wherein the cutoff value is determined by a mean plus 2 standard deviation analysis of multiple control samples.

Clause 83. The method of any one of clauses 72-82, wherein the reference level of laminin gamma 2 monomer is a level of laminin gamma 2 monomer in a calibrator.

Clause 84. A kit for detecting pancreatic cancer in a subject in need thereof, the kit comprising: (a) one or more reagents for detecting laminin gamma 2 monomer; and (b) one or more reagents for detecting at least one additional biomarker, wherein the at least one additional biomarker is selected from the group consisting of: carcinoembryonic antigen (CEA) and carbohydrate antigen 19-9 (CA19-9).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method of diagnosing hepatocellular carcinoma (HCC) in a subject in need thereof, the method comprising:
   (a) determining a level of laminin gamma 2 monomer and a level of one or both of protein induced vitamin K antagonist-II (PIVKA-II) and/or alpha fetoprotein (AFP) in a biological sample obtained from the subject using a kit comprising:
      (i) a 2H2 antibody, which specifically binds to laminin gamma 2 monomer, and one or both of:
      (ii) one or more antibodies that each specifically bind to protein induced vitamin K antagonist-II (PIVKA-II), and/or
      (iii) one or more antibodies that each specifically bind to alpha fetoprotein (AFP), wherein each of (i) and one or both of (ii) and/or (iii) are provided in separate containers;

(b) comparing the level of laminin gamma 2 monomer to a reference level of laminin gamma 2 monomer and the level of one or both of PIVKA-II and/or AFP to a reference level of one or both of PIVKA-II and/or AFP; and (c) identifying the subject as having HCC when the level of laminin gamma 2 monomer is greater than the reference level of laminin gamma 2 monomer and the level of one or both of PIVKA-II and/or AFP is greater than the reference level of PIVKA-II and/or AFP, wherein the reference level for laminin gamma 2 monomer is about 79.5 pg/mL, the reference level for PIVKA-II is about 40 mAU/mL, and the reference level for AFP is about 20 ng/mL.

2. The method of claim 1, wherein the levels of:

(a) laminin gamma 2 monomer and PIVKA-II are determined in the biological sample;

(b) laminin gamma 2 monomer and AFP are determined in the biological sample; or (c) laminin gamma 2 monomer, PIVKA-II, and AFP are determined in the biological sample.

3. The method of claim 2, wherein the subject is identified as having HCC when:

(a) the levels of laminin gamma 2 monomer and PIVKA-II in the biological sample are greater than the reference levels of laminin gamma 2 monomer and PIVKA-II;

(b) the levels of laminin gamma 2 monomer and AFP in the biological sample are greater than the reference levels of laminin gamma 2 monomer and AFP; or (c) the levels of laminin gamma 2 monomer, PIVKA-II, and AFP in the biological sample are greater than the reference levels of laminin gamma 2 monomer, PIVKA-II, and AFP.

4. The method of claim 1, wherein the biological sample is selected from a whole blood sample, a plasma sample, and a serum sample.

5. The method of claim 4, wherein the biological sample is a serum sample.

6. The method of claim 1, wherein the level of laminin gamma 2 monomer and the level of one or both of PIVKA-II and/or AFP in the biological sample is determined using an immunoassay.

7. The method of claim 6, wherein the immunoassay is a sandwich immunoassay.

8. The method of claim 1, wherein the reference level of laminin gamma 2 monomer is a cutoff level.

* * * * *